United States Patent
Schmidt et al.

(10) Patent No.: US 11,851,671 B2
(45) Date of Patent: Dec. 26, 2023

(54) PROGRAMMABLE ASSEMBLY OF VIRUS COMPOSITES FOR RECEPTOR-TARGETED GENE DELIVERY

(71) Applicant: Regents of the University of Minnesota, Minneapolis, MN (US)

(72) Inventors: Daniel Schmidt, Minneapolis, MN (US); Wendy Gordon, St. Paul, MN (US); Alina Catherine Zdechlik, Minnetonka, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 327 days.

(21) Appl. No.: 16/758,602

(22) PCT Filed: Oct. 23, 2018

(86) PCT No.: PCT/US2018/057119
§ 371 (c)(1),
(2) Date: Apr. 23, 2020

(87) PCT Pub. No.: WO2019/084015
PCT Pub. Date: May 2, 2019

(65) Prior Publication Data
US 2021/0180082 A1    Jun. 17, 2021

Related U.S. Application Data

(60) Provisional application No. 62/575,722, filed on Oct. 23, 2017.

(51) Int. Cl.
*C12N 15/86*    (2006.01)
*C07K 14/47*    (2006.01)
(Continued)

(52) U.S. Cl.
CPC .......... *C12N 15/86* (2013.01); *A61K 48/0008* (2013.01); *C07K 14/47* (2013.01); *C07K 16/28* (2013.01); *C12N 15/8645* (2013.01)

(58) Field of Classification Search
CPC ............... A61K 48/00; A61K 35/768; A61K 2039/525; C12N 15/86; C12N 7/00;
(Continued)

(56) References Cited

U.S. PATENT DOCUMENTS

| | | | |
|---|---|---|---|
| 10,584,321 B2 * | 3/2020 | Gao | C12N 7/00 |
| 2005/0106558 A1 * | 5/2005 | Perabo | C12N 15/86 |
| | | | 435/456 |

(Continued)

FOREIGN PATENT DOCUMENTS

WO    WO-2019084015 A1    5/2019

OTHER PUBLICATIONS

VanDenBerghe et al., Naturally occurring singleton residues in AAV capsid impact vector performance and illustrate structural constraints (Gene Therapy, 2009, 16:1416-1428) (Year: 2009).*

(Continued)

*Primary Examiner* — Arthur S Leonard
(74) *Attorney, Agent, or Firm* — Schwegman Lundberg & Woessner, P.A.

(57) ABSTRACT

Compositions providing, and methods for providing and using, targeted rAAV are disclosed.

18 Claims, 33 Drawing Sheets
Specification includes a Sequence Listing.

(51) Int. Cl.
   *C07K 16/28* (2006.01)
   *A61K 48/00* (2006.01)
   *C12N 15/864* (2006.01)
(58) Field of Classification Search
   CPC ........... C12N 2710/24132; C12N 2710/24143;
       C12N 2710/24134; C12N 2710/24161;
       C12N 2750/00043; C12N 2750/00022;
       C12N 2750/00023; C12N 2710/16222;
       C12N 2710/24121; C12N 2730/10122;
       C12N 2740/15022; C12N 2740/16222;
       C12N 2760/16122; C12N 2760/18022;
       C12N 2760/18122; C12N 2760/18422;
       C12N 2760/18522; C12N 2740/16122;
       C12N 2740/17022; C12N 2760/18622;
       C12N 2760/18722; C12N 2740/13022;
       C12N 2740/14022; C12N 2710/24122;
       C12N 2750/00042; C12N 15/90; C12N
       2320/32; C12N 2750/00021; C12N
       2750/00052; C12N 2750/00071; C12N
       15/63; C12N 15/8645; C12N 2750/14122;
       C12N 2750/14145
   See application file for complete search history.

(56) References Cited

U.S. PATENT DOCUMENTS

| | | | |
|---|---|---|---|
| 2005/0158281 | A1 | 7/2005 | Chamberlain et al. |
| 2009/0215879 | A1* | 8/2009 | Diprimio ........... A61K 31/7088 435/320.1 |
| 2012/0009268 | A1 | 1/2012 | Asokan et al. |
| 2014/0294771 | A1 | 10/2014 | Schaffer et al. |
| 2016/0340395 | A1 | 11/2016 | Gordon et al. |

OTHER PUBLICATIONS

Gonzalez-Prieto et al., HUH site-specific recombinases for targeted modification of the human genome (Trends in Biotech, 2013, 31:305-312). (Year: 2013).*
Lovendahl et al. Sequence-Directed Covalent Protein-DNA Linkages in a Single Step Using HUH-Tags (JACS, 2017, 139:7030-7035) (Year: 2017).*
Tong et al. Viral Capsid DNA Aptamer Conjugates as Multivalent Cell Targeting Vehicles (JACS, 2009, 131:11174-11178) (Year: 2009).*
"International Application Serial No. PCT/US2018/057119, International Search Report dated Jan. 25, 2019", 4 pgs.
"International Application Serial No. PCT/US2018/057119, Written Opinion dated Jan. 25, 2019", 8 pgs.
Hagen, Sven, et al., "Modular adeno-associated virus (rAAV) vectors used for cellular virus-directed enzyme prodrug therapy", Sc. Rep., 4, 3759, (2014), 1-11.
Liu, Y, et al., "Site-Specific Modification of Adeno-Associated Viruses via a Genetically Engineered Aldehyde Tag", (Oct. 5, 2012), 421-429.
Munch, Robert C., et al., "Displaying High-affinity Ligands on Adeno-associated Viral Vectors Enables Tumor Cell-specific and Safe Gene Transfer", Mol. Ther. 21, (2013), 109-118.
"International Application Serial No. PCT/US2018/057119, International Preliminary Report on Patentability dated May 7, 2020", 10 pgs.
Chandler, Michael, et al., "Breaking and joining single-stranded DNA: the HUH endonuclease superfamily", Nat. Rev. Microbiol., 11(8), (2013), 525-538.
Hedley, S. J., et al., "An adenovirus vector with a chimeric fiber incorporating stabilized single chain antibody achieves targeted gene delivery", Gene Therapy, 13, (2006), 88-94.
Lovendahl, Klaus N., et al., "Sequence-Directed Covalent Protein-DNA Linkages in a Single Step Using HUH-Tags", J. Am. Chem. Soc., 139(20), (2017), 7030-7035.
Yang, Oicheng, et al., "Development of Novel Cell Surface CD34-Targeted Recombinant Adenoassociated Virus Vectors for Gene Therapy", Human Gene Therapy, 9(13), (1998), 1929-1937.

* cited by examiner

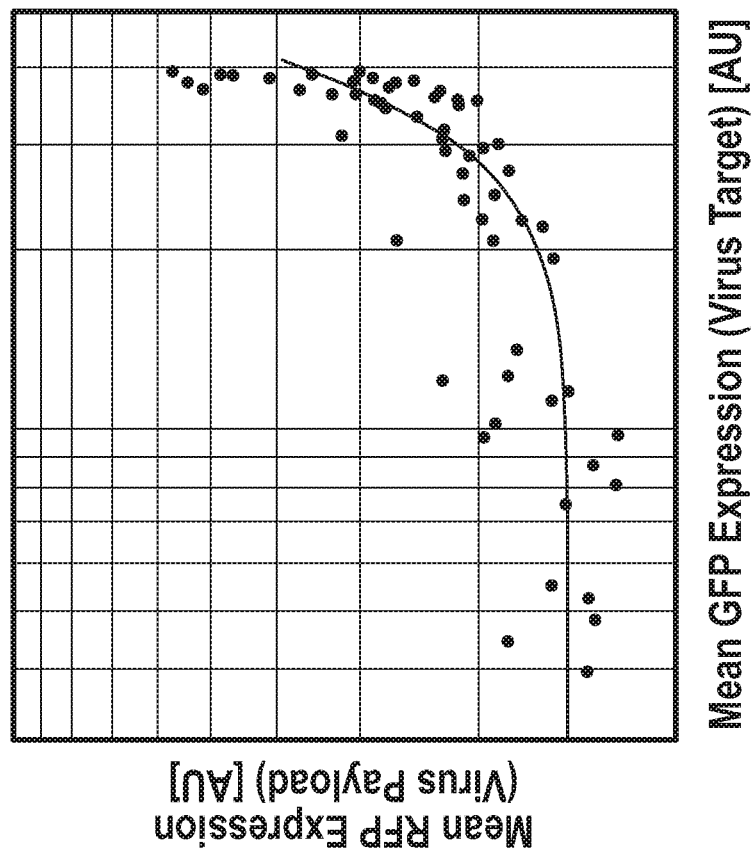
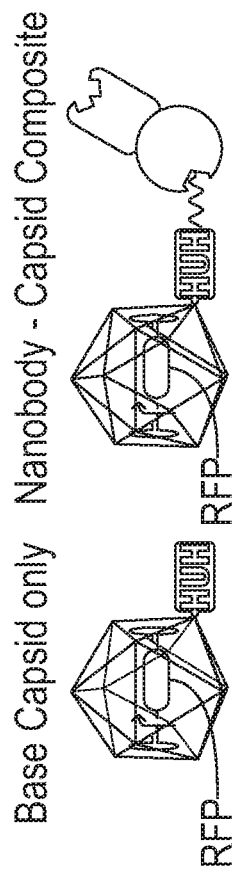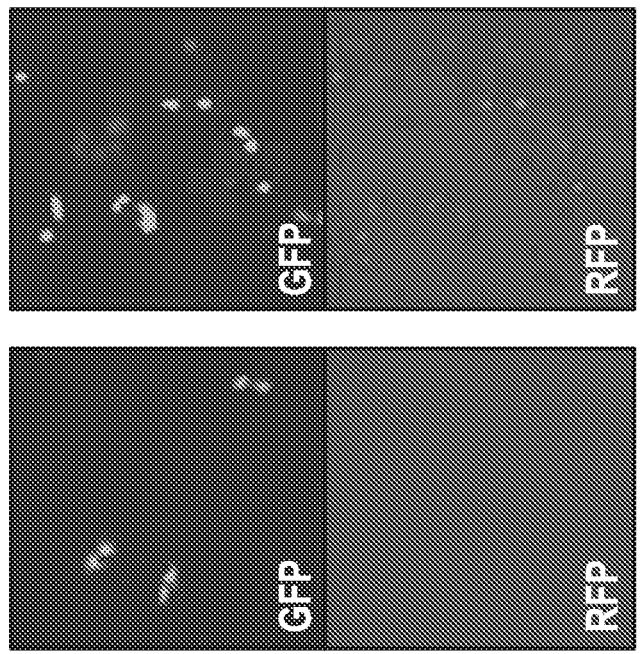
FIG. 6A
FIG. 6B

AAV2 VP1

```
  1 maadgylpdw ledtlsegir qwwklkpgpp ppkpaerhkd dsrglvlpgy kylgpfngld
 61 kgepvneada aalehdkayd rqldsqdnpy lkynhadaef qerlkedtsf ggnlgravfq
121 akkrvleplg lveepvktap gkkrpvehsp vepdsssgtg kagqqparkr lnfgqtgdad
181 svpdpqplgq ppaapsglgt ntmatgsgap madnnegadg vgnssgnwhc dstwmgdrvi
241 ttstrtwalp tynnhlykqi ssqsgasndn hyfgystpwg yfdfnrfhch fsprdwqrli
301 nnnwgfrpkr lnfklfniqv kevtqndgtt tiannltstv qvftdseyql pyvlgsahqg
361 clppfpadvf mvpqygyltl nngsqavgrs sfycleyfps qmlrtgnnft fsytfedvpf
421 hssyahsqsl drlmnplidq ylyylsrtnt psgtttqsrl qfsqagasdi rdqsrnwlpg
481 pcyrqqrvsk tsadnnnsey swtgatkyhl ngrdslvnpg pamashkdde ekffpqsgvl
541 ifgkqgsekt nvdiekvmit deeeirttnp vateqygsvs tnlqrgnrqa atadvntqgv
601 lpgmvwqdrd vylqgpiwak iphtdghfhp splmggfglk hpppqilikn tpvpanpstt
661 fsaakfasfi tqystgqvsv eiewelqken skrwnpeiqy tsnynksvnv dftvdtngvy
721 seprpigtry ltrnl    (SEQ ID NO:53)
```

AAV2 VP2

```
  1 mapgkkrpve hspvepdsss gtgkagqqpa rkrlnfgqtg dadsvpdpqp lgqppaapsg
 61 lgtntmatgs gapmadnneg adgvgnssgn whcdstwmgd rvittstrtw alptynnhly
121 kqissqsgas ndnhyfgyst pwgyfdfnrf hchfsprdwq rlinnnwgfr pkrlnfklfn
181 iqvkevtqnd gtttiannlt stvqvftdse yqlpyvlgsa hqgclppfpa dvfmvpqygy
241 ltlnngsqav grssfycley fpsqmlrtgn nftfsytfed vpfhssyahs qsldrlmnpl
301 idqylyylsr tntpsgtttq srlqfsqaga sdirdqsrnw lpgpcyrqqr vsktsadnnn
361 seyswtgatk yhlngrdslv npgpamashk ddeekffpqs gvlifgkqgs ektnvdiekv
421 mitdeeeirt tnpvateqyg svstnlqrgn rqaatadvnt qgvlpgmvwq drdvylqgpi
481 wakiphtdgh fhpsplmggf glkhpppqil ikntpvpanp sttfsaakfa sfitqystgq
541 vsveiewelq kenskrwnpe iqytsnynks vnvdftvdtn gvyseprpig tryltrnl(SEQ
   ID NO:54)
```

AAV2 VP3

```
  1 matgsgapma dnnegadgvg nssgnwhcds twmgdrvitt strtwalpty nnhlykqiss
 61 qsgasndnhy fgystpwgyf dfnrfhchfs prdwqrlinn nwgfrpkrln fklfniqvke
121 vtqndgttti annltstvqv ftdseyqlpy vlgsahqgcl ppfpadvfmv pqygyltlnn
181 gsqavgrssf ycleyfpsqm lrtgnnftfs ytfedvpfhs syahsqsldr lmnplidqyl
241 yylsrtntps gtttqsrlqf sqagasdird qsrnwlpgpc yrqqrvskts adnnnseysw
301 tgatkyhlng rdslvnpgpa mashkddeek ffpqsgvlif gkqgsektnv diekvmitde
361 eeirttnpva teqygsvstn lqrgnrqaat advntqgvlp gmvwqdrdvy lqgpiwakip
421 htdghfhpsp lmggfglkhp ppqilikntp vpanpsttfs aakfasfitq ystgqvsvei
481 ewelqkensk rwnpeiqyts nynksvnvdf tvdtngvyse prpigtrylt rnl
```

(SEQ ID NO:55)

FIG. 8

AAV8 VP1

```
  1 maadgylpdw lednlsegir ewwalkpgap kpkanqqkqd dgrglvlpgy kylgpfngld
 61 kgepvnaada aalehdkayd qqlqagdnpy lrynhadaef qerlqedtsf ggnlgravfq
121 akkrvleplg lveegaktap gkkrpvepsp qrspdsstgi gkkgqqpark rlnfgqtgds
181 esvpdpqplg eppaapsgvg pntmaaggga pmadnnegad gvgsssgnwh cdstwlgdrv
241 ittstrtwal ptynnhlykq isngtsggat ndntyfgyst pwgyfdfnrf hchfsprdwq
301 rlinnnwgfr pkrlsfklfn iqvkevtqne gtktiannlt stiqvftdse yqlpyvlgsa
361 hqgclppfpa dvfmipqygy ltlnngsqav grssfycley fpsqmlrtgn nfqftytfed
421 vpfhssyahs qsldrlmnpl idqylyylsr tqttggtant qtlgfsqggp ntmanqaknw
481 lpgpcyrqqr vstttgqnnn snfawtagtk yhlngrnsla npgiamathk ddeerffpsn
541 gilifgkqna ardnadysdv mltseeeikt tnpvateeyg ivadnlqqqn tapqigtvns
601 qgalpgmvwq nrdvylqgpi wakiphtdgn fhpsplmggf glkhpppqil ikntpvpadp
661 pttfnqskln sfitqystgq vsveiewelq kenskrwnpe iqytsnyyks tsvdfavnte
721 gvyseprpig tryltrnl  (SEQ ID NO:56)
```

AAV7 VP1

```
  1 maadgylpdw lednlsegir ewwdlkpgap kpkanqqkqd ngrglvlpgy kylgpfngld
 61 kgepvnaada aalehdkayd qqlkagdnpy lrynhadaef qerlqedtsf ggnlgravfq
121 akkrvleplg lveegaktap akkrpvepsp qrspdsstgi gkkgqqpark rlnfgqtgds
181 esvpdpqplg eppaapssvg sgtvaaggga pmadnnegad gvgnasgnwh cdstwlgdrv
241 ittstrtwal ptynnhlykq issetagstn dntyfgystp wgyfdfnrfh chfsprdwqr
301 linnnwgfrp kklrfklfni qvkevttndg vttiannlts tiqvfsdsey qlpyvlgsah
361 qgclppfpad vfmipqygyl tlnngsqsvg rssfycleyf psqmlrtgnn fefsysfedv
421 pfhssyahsq sldrlmnpli dqylyylart qsnpggtagn relqfyqggp stmaeqaknw
481 lpgpcfrqqr vsktldqnnn snfawtgatk yhlngrnslv npgvamathk ddedrffpss
541 gvlifgktga tnkttlenvl mtneeeirpt npvateeygi vssnlqaant aaqtqvvnnq
601 galpgmvwqn rdvylqgpiw akiphtdgnf hpsplmggfg lkhpppqili kntpvpanpp
661 evftpakfas fitqystgqv sveiewelqk enskrwnpei qytsnfekqt gvdfavdsqg
721 vyseprpigt ryltrnl (SEQ ID NO:57)
```

FIG. 8 (Continued)

FIG. 10A
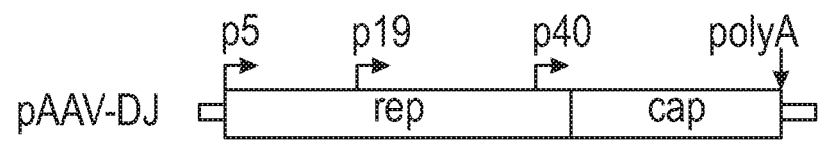
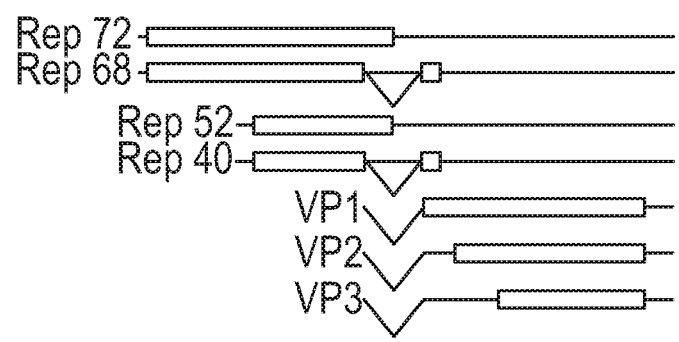
FIG. 10B

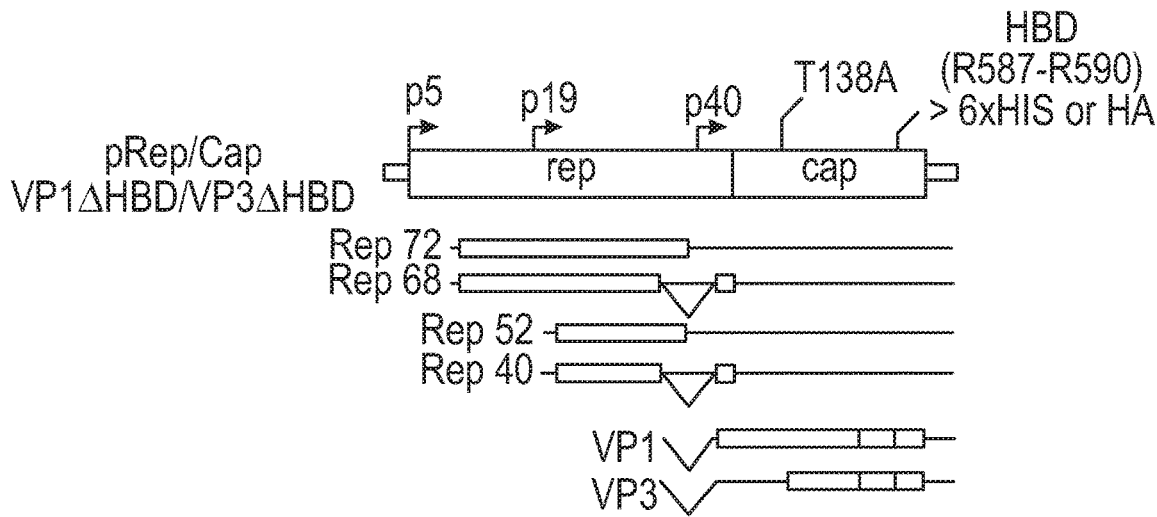
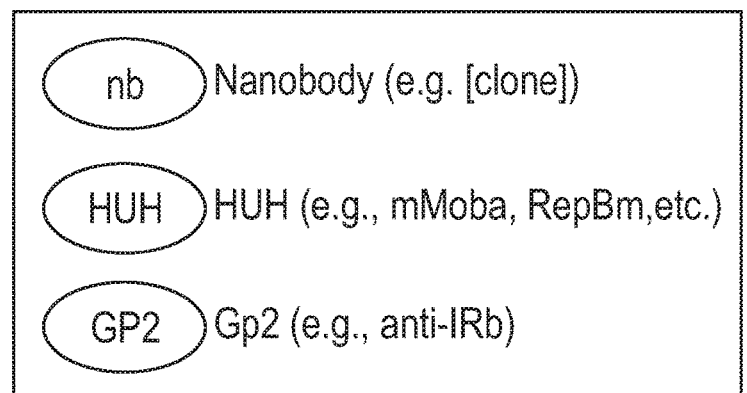
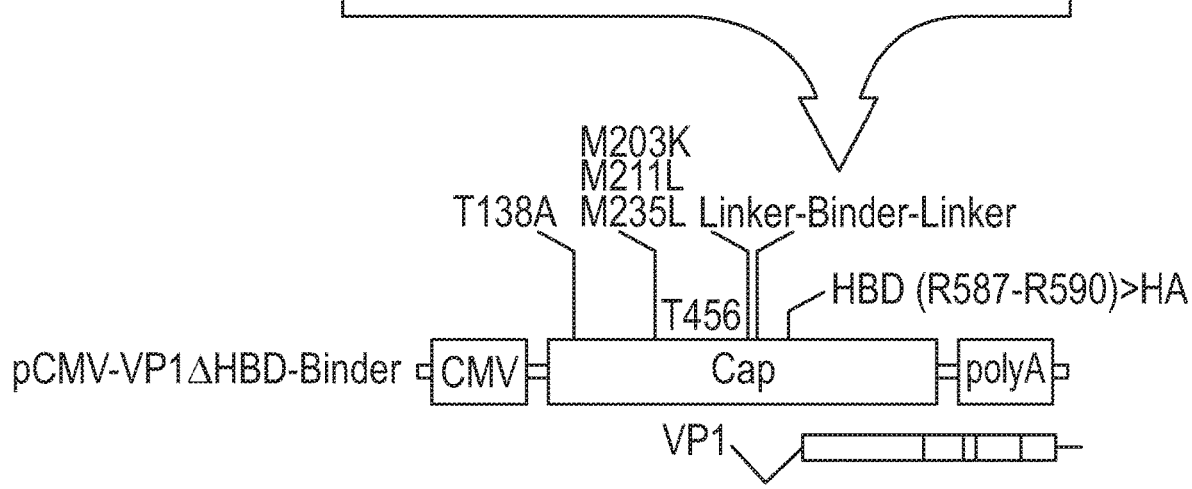
FIG. 10E

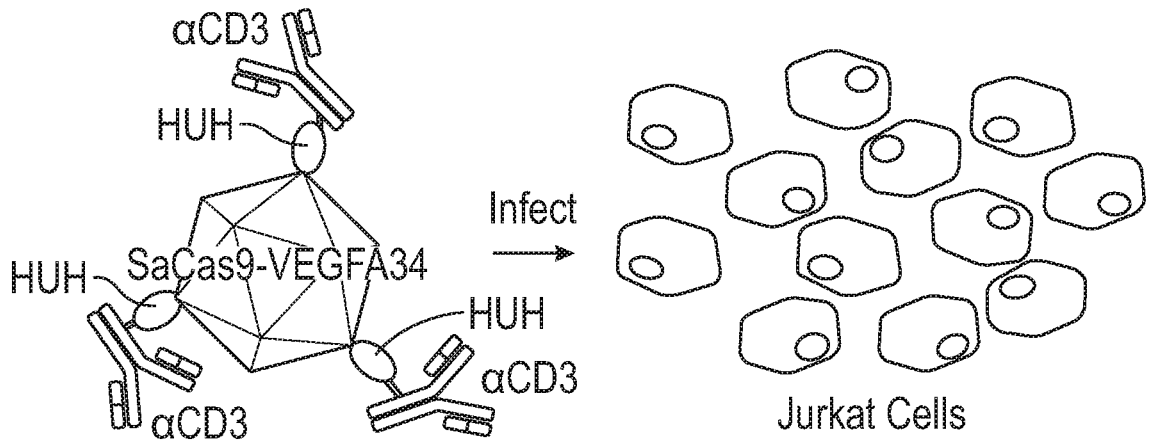
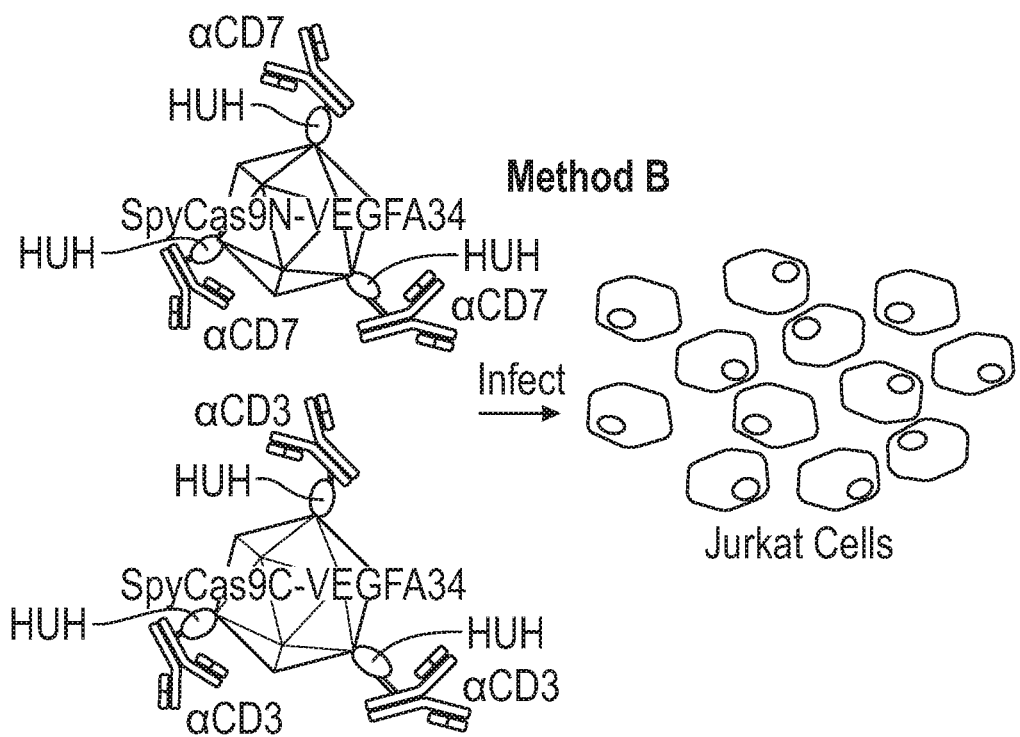
FIG. 21B

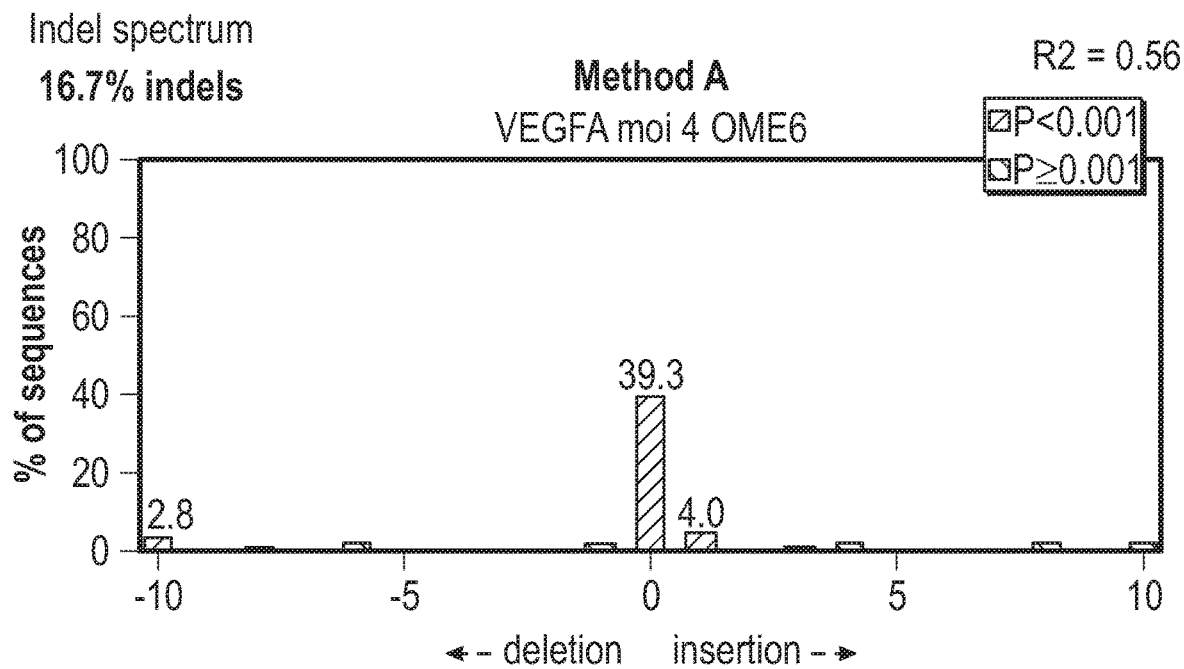
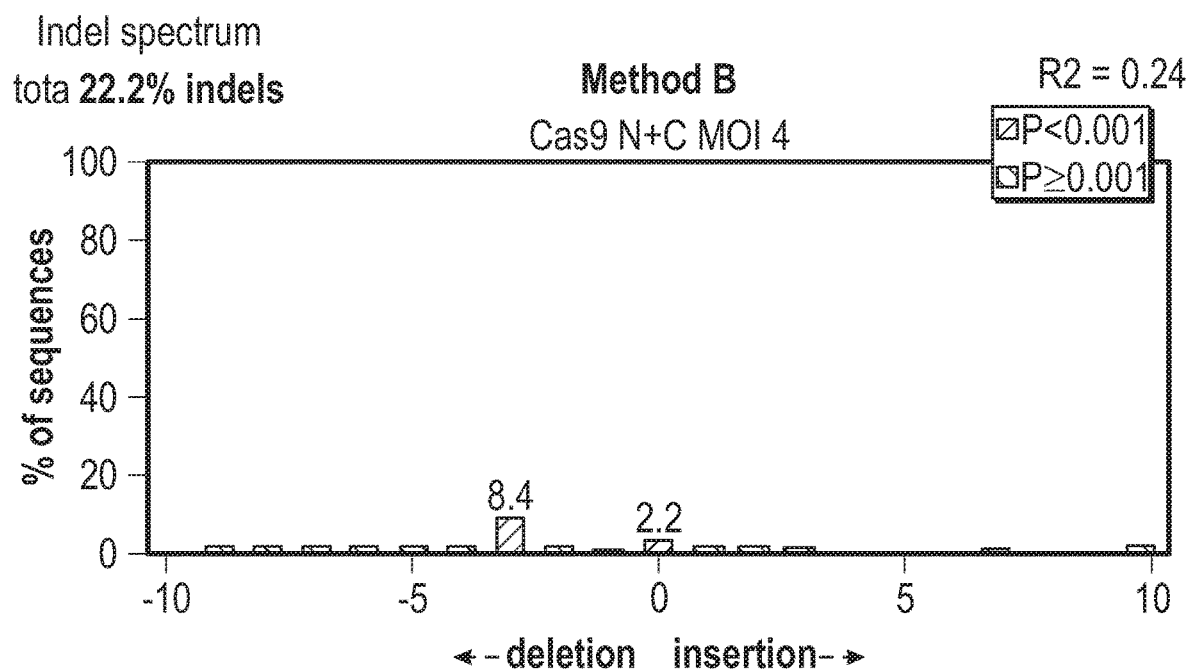
FIG. 21D

SEQUENCE LISTING

<160> NUMBER OF SEQ ID NOS: 59

<210> SEQ ID NO 1
<211> LENGTH: 15
<212> TYPE: DNA
<213> ORGANISM: Porcine circovirus

<400> SEQUENCE: 1
aagtattacc agaaa                                                        15

<210> SEQ ID NO 2
<211> LENGTH: 116
<212> TYPE: PRT
<213> ORGANISM: Porcine circovirus

<400> SEQUENCE: 2

Ser Pro Ser Lys Lys Asn Gly Arg Ser Gly Pro Gln Pro His Lys Arg
1               5                   10                  15

Trp Val Phe Thr Leu Asn Asn Pro Ser Glu Asp Glu Arg Lys Lys Ile
            20                  25                  30

Arg Asp Leu Pro Ile Ser Leu Phe Asp Tyr Phe Ile Val Gly Glu Glu

```
            35                  40                  45
Gly Asn Glu Glu Gly Arg Thr Pro His Leu Gln Gly Phe Ala Asn Phe
 50                  55                  60

Val Lys Lys Gln Thr Phe Asn Lys Val Lys Trp Tyr Leu Gly Ala Arg
 65                  70                  75                  80

Cys His Ile Glu Lys Ala Lys Gly Thr Asp Gln Gln Asn Lys Glu Tyr
                 85                  90                  95

Cys Ser Lys Glu Gly Asn Leu Leu Met Glu Glu Gly Ala Pro Arg Ser
            100                 105                 110

Gln Gly Gln Arg
        115

<210> SEQ ID NO 3
<211> LENGTH: 340
<212> TYPE: PRT
<213> ORGANISM: Enterobacteria phage

<400> SEQUENCE: 3

Lys Ser Arg Arg Gly Phe Ala Ile Gln Arg Leu Met Asn Ala Met Arg
 1               5                  10                  15

Gln Ala His Ala Asp Gly Trp Phe Ile Val Phe Asp Thr Leu Thr Leu
                20                  25                  30

Ala Asp Asp Arg Leu Glu Ala Phe Tyr Asp Asn Pro Asn Ala Leu Arg
            35                  40                  45

Asp Tyr Phe Arg Asp Ile Gly Arg Met Val Leu Ala Ala Glu Gly Arg
 50                  55                  60

Lys Ala Asn Asp Ser His Ala Asp Cys Tyr Gln Tyr Phe Cys Val Pro
 65                  70                  75                  80

Glu Tyr Gly Thr Ala Asn Gly Arg Leu His Phe His Ala Val His Phe
                 85                  90                  95

Met Arg Thr Leu Pro Thr Gly Ser Val Asp Pro Asn Phe Gly Arg Arg
            100                 105                 110

Val Arg Asn Arg Arg Gln Leu Asn Ser Leu Gln Asn Thr Trp Pro Tyr
            115                 120                 125

Gly His Ser Met Pro Ile Ala Val Arg Tyr Thr Gln Asp Ala Phe Ser
130                 135                 140

Arg Ser Gly Trp Leu Trp Pro Val Asp Ala Lys Gly Glu Pro Leu Lys
145                 150                 155                 160

Ala Thr Ser Tyr Met Ala Val Gly Phe Tyr Val Ala Lys Tyr Val Asn
                165                 170                 175

Lys Lys Ser Asp Met Asp Leu Ala Ala Lys Gly Leu Gly Ala Lys Glu
            180                 185                 190

Trp Asn Asn Ser Leu Lys Thr Lys Leu Ser Leu Leu Pro Lys Lys Leu
            195                 200                 205

Phe Arg Ile Arg Met Ser Arg Asn Phe Gly Met Lys Met Leu Thr Met
210                 215                 220

Thr Asn Leu Ser Thr Glu Cys Leu Ile Gln Leu Thr Lys Leu Gly Tyr
225                 230                 235                 240

Asp Ala Thr Pro Phe Asn Gln Ile Leu Lys Gln Asn Ala Lys Arg Glu
                245                 250                 255

Met Arg Leu Arg Leu Gly Lys Val Thr Val Ala Asp Val Leu Ala Ala
            260                 265                 270

Gln Pro Val Thr Thr Asn Leu Leu Lys Phe Met Arg Ala Ser Ile Lys
            275                 280                 285
```

```
Met Ile Gly Val Ser Asn Leu Gln Ser Phe Ile Ala Ser Met Thr Gln
    290                 295                 300
Lys Leu Thr Leu Ser Asp Ile Ser Asp Glu Ser Lys Asn Tyr Leu Asp
305                 310                 315                 320
Lys Ala Gly Ile Thr Thr Ala Cys Leu Arg Ile Lys Ser Lys Trp Thr
                325                 330                 335
Ala Gly Gly Lys
            340

<210> SEQ ID NO 4
<211> LENGTH: 186
<212> TYPE: PRT
<213> ORGANISM: Escherichia coli

<400> SEQUENCE: 4

Met Ala Ile Tyr His Leu Thr Ala Lys Thr Gly Ser Arg Ser Gly Gly
1               5                   10                  15
Gln Ser Ala Arg Ala Lys Ala Asp Tyr Ile Gln Arg Glu Gly Lys Tyr
                20                  25                  30
Ala Arg Asp Met Asp Glu Val Leu His Ala Glu Ser Gly His Met Pro
            35                  40                  45
Glu Phe Val Glu Arg Pro Ala Asp Tyr Trp Asp Ala Asp Leu Tyr
    50                  55                  60
Glu Arg Ala Asn Gly Arg Leu Phe Lys Glu Val Glu Phe Ala Leu Pro
65                  70                  75                  80
Val Glu Leu Thr Leu Asp Gln Gln Lys Ala Leu Ala Ser Glu Phe Ala
                85                  90                  95
Gln His Leu Thr Gly Ala Glu Arg Leu Pro Tyr Thr Leu Ala Ile His
            100                 105                 110
Ala Gly Gly Gly Glu Asn Pro His Cys His Leu Met Ile Ser Glu Arg
        115                 120                 125
Ile Asn Asp Gly Ile Glu Arg Pro Ala Ala Gln Trp Phe Lys Arg Tyr
    130                 135                 140
Asn Gly Lys Thr Pro Glu Lys Gly Gly Ala Gln Lys Thr Glu Ala Leu
145                 150                 155                 160
Lys Pro Lys Ala Trp Leu Glu Gln Thr Arg Glu Ala Trp Ala Asp His
                165                 170                 175
Ala Asn Arg Ala Leu Glu Arg Ala Gly His
            180                 185

<210> SEQ ID NO 5
<211> LENGTH: 330
<212> TYPE: PRT
<213> ORGANISM: E. Coli

<400> SEQUENCE: 5

Met Met Ser Ile Ala Gln Val Arg Ser Ala Gly Ser Ala Gly Asn Tyr
1               5                   10                  15
Tyr Thr Asp Lys Asp Asn Tyr Tyr Val Leu Gly Ser Met Gly Glu Arg
                20                  25                  30
Trp Ala Gly Arg Gly Ala Glu Gln Leu Gly Leu Gln Gly Ser Val Asp
            35                  40                  45
Lys Asp Val Phe Thr Arg Leu Leu Glu Gly Arg Leu Pro Asp Gly Ala
        50                  55                  60
Asp Leu Ser Arg Met Gln Asp Gly Ser Asn Arg His Arg Pro Gly Tyr
65                  70                  75                  80
```

```
Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Thr
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Lys Met Ala Glu Trp Met Gln Thr Leu Lys Glu Thr Gly Phe Asp Ile
        275                 280                 285

Arg Ala Tyr Arg Asp Ala Ala Asp Gln Arg Ala Asp Leu Arg Thr Leu
    290                 295                 300

Thr Pro Gly Pro Ala Ser Gln Asp Gly Pro Asp Val Gln Gln Ala Val
305                 310                 315                 320

Thr Gln Ala Ile Ala Gly Leu Ser Glu Arg
                325                 330

<210> SEQ ID NO 6
<211> LENGTH: 138
<212> TYPE: PRT
<213> ORGANISM: Streptococcus algalactiase

<400> SEQUENCE: 6

Met Ala Lys Glu Lys Ala Arg Tyr Phe Thr Phe Leu Leu Tyr Pro Glu
1               5                   10                  15

Ser Ile Pro Ser Asp Trp Glu Leu Lys Leu Glu Thr Leu Gly Val Pro
            20                  25                  30

Met Ala Ile Ser Pro Leu His Asp Lys Asp Lys Ser Ser Ile Lys Gly
        35                  40                  45

Gln Lys Tyr Lys Lys Ala His Tyr His Val Leu Tyr Ile Ala Lys Asn
    50                  55                  60

Pro Val Thr Ala Asp Ser Val Arg Lys Lys Ile Lys Leu Leu Leu Gly
65                  70                  75                  80

Glu Lys Ser Leu Ala Met Val Gln Val Val Leu Asn Val Glu Asn Met
                85                  90                  95

Tyr Leu Tyr Leu Thr His Glu Ser Lys Asp Ala Ile Ala Lys Lys Lys
            100                 105                 110

His Val Tyr Asp Lys Ala Asp Ile Lys Leu Ile Asn Asn Phe Asp Ile
        115                 120                 125
```

Asp Arg Tyr Leu Glu Phe Asx Asn Tyr Val
        130                 135

<210> SEQ ID NO 7
<211> LENGTH: 101
<212> TYPE: PRT
<213> ORGANISM: Faba bean necrosis yellows virus

<400> SEQUENCE: 7

Met Ala Arg Gln Val Ile Cys Trp Cys Phe Thr Leu Asn Asn Pro Leu
1               5                   10                  15

Ser Pro Leu Ser Leu His Asp Ser Met Lys Tyr Leu Val Tyr Gln Thr
            20                  25                  30

Glu Gln Gly Glu Ala Gly Asn Ile His Phe Gln Gly Tyr Ile Glu Met
        35                  40                  45

Lys Lys Arg Thr Ser Leu Ala Gly Met Lys Lys Leu Ile Pro Gly Ala
    50                  55                  60

His Phe Glu Lys Arg Arg Gly Thr Gln Gly Ala Arg Ala Tyr Ser
65                  70                  75                  80

Met Lys Glu Asp Thr Arg Leu Glu Gly Pro Trp Glu Tyr Gly Glu Phe
                85                  90                  95

Val Pro Asn Glu Ser
            100

<210> SEQ ID NO 8
<211> LENGTH: 218
<212> TYPE: PRT
<213> ORGANISM: Staphylococcus aureus

<400> SEQUENCE: 8

Ala Met Tyr His Phe Gln Asn Lys Phe Val Ser Lys Ala Asn Gly Gln
1               5                   10                  15

Ser Ala Thr Ala Lys Ser Ala Tyr Asn Ser Ala Ser Arg Ile Lys Asp
            20                  25                  30

Phe Lys Glu Asn Glu Phe Lys Asp Tyr Ser Asn Lys Gln Cys Asp Tyr
        35                  40                  45

Ser Glu Ile Leu Leu Pro Asn Asn Ala Asp Asp Lys Phe Lys Asp Arg
    50                  55                  60

Glu Tyr Leu Trp Asn Lys Val His Asp Val Glu Asn Arg Lys Asn Ser
65                  70                  75                  80

Gln Val Ala Arg Glu Ile Ile Ile Gly Leu Pro Asn Glu Phe Asp Pro
                85                  90                  95

Asn Ser Asn Ile Glu Leu Ala Lys Glu Phe Ala Glu Ser Leu Ser Asn
            100                 105                 110

Glu Gly Met Ile Val Asp Leu Asn Ile His Lys Ile Asn Glu Glu Asn
        115                 120                 125

Pro His Ala His Leu Leu Cys Thr Leu Arg Gly Leu Asp Lys Asn Asn
    130                 135                 140

Glu Phe Glu Pro Lys Arg Lys Gly Asn Asp Tyr Ile Arg Asp Trp Asn
145                 150                 155                 160

Thr Lys Glu Lys His Asn Glu Trp Arg Lys Arg Trp Glu Asn Val Gln
                165                 170                 175

Asn Lys His Leu Glu Lys Asn Gly Phe Ser Val Arg Val Ser Ala Asp
            180                 185                 190

Ser Tyr Lys Asn Gln Asn Ile Asp Leu Glu Pro Thr Lys Lys Glu Gly
        195                 200                 205

-continued

Trp Lys Ala Arg Lys Phe Glu Asp Glu Thr
        210                 215

<210> SEQ ID NO 9
<211> LENGTH: 298
<212> TYPE: PRT
<213> ORGANISM: Adeno-associated virus

<400> SEQUENCE: 9

Met Leu Ser His Met Val Leu Thr Arg Gln Asp Ile Gly Arg Ala Ala
1               5                   10                  15

Ser Tyr Tyr Glu Asp Gly Ala Asp Tyr Tyr Ala Lys Asp Gly Asp
            20                  25                  30

Ala Ser Glu Trp Gln Gly Lys Gly Ala Glu Leu Gly Leu Ser Gly
        35                  40                  45

Glu Val Asp Ser Lys Arg Phe Arg Glu Leu Leu Ala Gly Asn Ile Gly
    50                  55                  60

Glu Gly His Arg Ile Met Arg Ser Ala Thr Arg Gln Asp Ser Lys Glu
65                  70                  75                  80

Arg Ile Gly Leu Asp Leu Thr Phe Ser Ala Pro Lys Ser Val Ser Leu
                85                  90                  95

Gln Ala Leu Val Ala Gly Asp Ala Glu Ile Ile Lys Ala His Asp Arg
            100                 105                 110

Ala Val Ala Arg Thr Leu Glu Gln Ala Glu Ala Arg Ala Gln Ala Arg
        115                 120                 125

Gln Lys Ile Gln Gly Lys Thr Arg Ile Glu Thr Thr Gly Asn Leu Val
    130                 135                 140

Ile Gly Lys Phe Arg His Glu Thr Ser Arg Glu Arg Asp Pro Gln Leu
145                 150                 155                 160

His Thr His Ala Val Ile Leu Asn Met Thr Lys Arg Ser Asp Gly Gln
                165                 170                 175

Trp Arg Ala Leu Lys Asn Asp Glu Ile Val Lys Ala Thr Arg Tyr Leu
            180                 185                 190

Gly Ala Val Tyr Asn Ala Glu Leu Ala His Glu Leu Gln Lys Leu Gly
        195                 200                 205

Tyr Gln Leu Arg Tyr Gly Lys Asp Gly Asn Phe Asp Leu Ala His Ile
    210                 215                 220

Asp Arg Gln Gln Ile Glu Gly Phe Ser Lys Arg Thr Glu Gln Ile Ala
225                 230                 235                 240

Glu Trp Tyr Ala Ala Arg Gly Leu Asp Pro Asn Ser Val Ser Leu Glu
                245                 250                 255

Gln Lys Gln Ala Ala Lys Val Leu Ser Arg Ala Lys Lys Thr Ser Val
            260                 265                 270

Asp Arg Glu Ala Leu Arg Ala Glu Trp Gln Ala Thr Ala Lys Glu Leu
        275                 280                 285

Gly Ile Asp Phe Ser Thr Leu Tyr Cys Val
    290                 295

<210> SEQ ID NO 10
<211> LENGTH: 120
<212> TYPE: PRT
<213> ORGANISM: Tomato yellow leaf curl virus

<400> SEQUENCE: 10

Met Pro Arg Leu Phe Lys Ile Tyr Ala Lys Asn Tyr Phe Leu Thr Tyr
1               5                   10                  15

```
Pro Asn Cys Ser Leu Ser Lys Glu Glu Ala Leu Ser Gln Leu Lys Lys
         20                  25                  30

Leu Glu Thr Pro Thr Asn Lys Lys Tyr Ile Lys Val Cys Lys Glu Leu
         35                  40                  45

His Glu Asn Gly Glu Pro His Leu His Val Leu Ile Gln Phe Glu Gly
 50                  55                  60

Lys Tyr Gln Cys Lys Asn Gln Arg Phe Phe Asp Leu Val Ser Pro Asn
 65                  70                  75                  80

Arg Ser Ala His Phe His Pro Asn Ile Gln Ala Ala Lys Ser Ser Thr
                 85                  90                  95

Asp Val Lys Thr Tyr Val Glu Lys Asp Gly Asn Phe Ile Asp Phe Gly
         100                 105                 110

Val Ser Gln Ile Asp Gly Arg Ser
         115                 120

<210> SEQ ID NO 11
<211> LENGTH: 45
<212> TYPE: DNA
<213> ORGANISM: Staphylococcus aureus

<400> SEQUENCE: 11
acgcgaacgg aacgttcgca taagtgcgcc cttacgggat ttaac            45

<210> SEQ ID NO 12
<211> LENGTH: 23
<212> TYPE: DNA
<213> ORGANISM: Streptococcus agalactiae

<400> SEQUENCE: 12
tgcttccgta ctacgacccc cca                                    23

<210> SEQ ID NO 13
<211> LENGTH: 22
<212> TYPE: DNA
<213> ORGANISM: E. coli

<400> SEQUENCE: 13
tttgcgtggg gtgtggtgct tt                                     22

<210> SEQ ID NO 14
<211> LENGTH: 38
<212> TYPE: DNA
<213> ORGANISM: E. coli

<400> SEQUENCE: 14
ccagtttctc gaagagaaac cggtaagtgc accctccc                    38

<210> SEQ ID NO 15

<400> SEQUENCE: 15

000

<210> SEQ ID NO 16

<400> SEQUENCE: 16

000

<210> SEQ ID NO 17
```

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 130
<212> TYPE: PRT
<213> ORGANISM: Fructobacilus tropaeoli

<400> SEQUENCE: 20

```
Met Ser Glu Lys Lys Glu Ile Val Lys Gly Arg Asp Trp Thr Phe Leu
1               5                   10                  15

Val Tyr Pro Glu Ser Ala Pro Glu Asn Trp Arg Thr Ile Leu Asp Glu
            20                  25                  30

Thr Phe Met Arg Trp Val Glu Ser Pro Leu His Asp Lys Asp Val Asn
        35                  40                  45

Ala Asp Gly Glu Ile Lys Lys Pro His Trp His Ile Leu Leu Ser Ser
    50                  55                  60

Asp Gly Pro Ile Thr Gln Thr Ala Val Gln Lys Ile Ile Gly Pro Leu
65                  70                  75                  80

Asn Cys Pro Asn Ala Gln Lys Val Gly Ser Ala Lys Gly Leu Val Arg
                85                  90                  95

Tyr Met Val His Leu Asp Asn Pro Glu Lys Tyr Gln Tyr Ser Leu Asp
            100                 105                 110

Glu Ile Val Gly His Asn Gly Ala Asp Val Ala Ser Tyr Phe Glu Leu
        115                 120                 125

Thr Ala
    130
```

<210> SEQ ID NO 21
<211> LENGTH: 111
<212> TYPE: PRT
<213> ORGANISM: Duck circovirus

<400> SEQUENCE: 21

```
Met Ala Lys Ser Gly Asn Tyr Ser Tyr Lys Arg Trp Val Phe Thr Ile
1               5                   10                  15

Asn Asn Pro Thr Phe Glu Asp Tyr Val His Val Leu Glu Phe Cys Thr
            20                  25                  30

Leu Asp Asn Cys Lys Phe Ala Ile Val Gly Glu Glu Lys Gly Ala Asn
        35                  40                  45

Gly Thr Pro His Leu Gln Gly Phe Leu Asn Leu Arg Ser Asn Ala Arg
    50                  55                  60

Ala Ala Ala Leu Glu Glu Ser Leu Gly Gly Arg Ala Trp Leu Ser Arg
65                  70                  75                  80

Ala Arg Gly Ser Asp Glu Asp Asn Glu Glu Tyr Cys Ala Lys Glu Ser
                85                  90                  95
```

Thr Tyr Leu Arg Val Gly Glu Pro Val Ser Lys Gly Arg Ser Ser
              100                 105                 110

<210> SEQ ID NO 22
<211> LENGTH: 15
<212> TYPE: PRT
<213> ORGANISM: Artificial Sequence
<220> FEATURE:
<223> OTHER INFORMATION: a synthetic amino acid linker

<400> SEQUENCE: 22

Gly Gly Gly Gly Ser Gly Gly Gly Ser Gly Gly Gly Gly Ser
1               5                   10                  15

<210> SEQ ID NO 23

<400> SEQUENCE: 23

000

<210> SEQ ID NO 24
<211> LENGTH: 10
<212> TYPE: PRT
<213> ORGANISM: Artificial Sequence
<220> FEATURE:
<223> OTHER INFORMATION: A synthetic amino acid linker

<400> SEQUENCE: 24

Glu Ala Ala Ala Lys Glu Ala Ala Ala Lys
1               5                   10

<210> SEQ ID NO 25
<211> LENGTH: 8
<212> TYPE: PRT
<213> ORGANISM: Artificial Sequence
<220> FEATURE:
<223> OTHER INFORMATION: A synthetic amino acid linker

<400> SEQUENCE: 25

Gly Gly Gly Gly Gly Gly Gly Gly
1               5

<210> SEQ ID NO 26
<211> LENGTH: 6
<212> TYPE: PRT
<213> ORGANISM: Artificial Sequence
<220> FEATURE:
<223> OTHER INFORMATION: A synthetic amino acid linker

<400> SEQUENCE: 26

Gly Gly Gly Gly Gly Gly
1               5

<210> SEQ ID NO 27
<211> LENGTH: 15
<212> TYPE: PRT
<213> ORGANISM: Artificial Sequence
<220> FEATURE:
<223> OTHER INFORMATION: A synthetic amino acid linker

<400> SEQUENCE: 27

Glu Ala Ala Ala Lys Glu Ala Ala Ala Lys Glu Ala Ala Ala Lys
1               5                   10                  15

<210> SEQ ID NO 28
<211> LENGTH: 5
<212> TYPE: PRT

```
<213> ORGANISM: Artificial Sequence
<220> FEATURE:
<223> OTHER INFORMATION: A synthetic amino acid linker

<400> SEQUENCE: 28

Glu Ala Ala Ala Lys
1               5

<210> SEQ ID NO 29
<211> LENGTH: 46
<212> TYPE: PRT
<213> ORGANISM: Artificial Sequence
<220> FEATURE:
<223> OTHER INFORMATION: A synthetic amino acid linker

<400> SEQUENCE: 29

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
            35                  40                  45

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33
<211> LENGTH: 20
<212> TYPE: PRT
<213> ORGANISM: Artificial Sequence
<220> FEATURE:
<223> OTHER INFORMATION: A synthetic amino acid linker

<400> SEQUENCE: 33

Gly Gly Gly Gly Ser Gly Gly Gly Gly Ser Gly Gly Gly Gly Ser Gly
1               5                   10                  15

Gly Gly Gly Ser
            20

<210> SEQ ID NO 34
<211> LENGTH: 5
<212> TYPE: PRT
<213> ORGANISM: Artificial Sequence
<220> FEATURE:
<223> OTHER INFORMATION: A synthetic amino acid linker

<400> SEQUENCE: 34

Gly Gly Gly Gly Ser
1               5
```

```
<210> SEQ ID NO 35
<211> LENGTH: 5
<212> TYPE: PRT
<213> ORGANISM: Artificial Sequence
<220> FEATURE:
<223> OTHER INFORMATION: A synthetic amino acid linker

<400> SEQUENCE: 35

Pro Ala Pro Ala Pro
1               5

<210> SEQ ID NO 36
<211> LENGTH: 12
<212> TYPE: PRT
<213> ORGANISM: Artificial Sequence
<220> FEATURE:
<223> OTHER INFORMATION: A synthetic amino acid linker

<400> SEQUENCE: 36

Ala Glu Ala Ala Ala Lys Glu Ala Ala Ala Lys Ala
1               5                   10

<210> SEQ ID NO 37
<211> LENGTH: 10
<212> TYPE: PRT
<213> ORGANISM: Artificial Sequence
<220> FEATURE:
<223> OTHER INFORMATION: A synthetic amino acid linker

<400> SEQUENCE: 37

Gly Gly Gly Gly Ser Gly Gly Gly Gly Ser
1               5                   10

<210> SEQ ID NO 38
<211> LENGTH: 34
<212> TYPE: PRT
<213> ORGANISM: Artificial Sequence
<220> FEATURE:
<223> OTHER INFORMATION: A synthetic amino acid linker

<400> SEQUENCE: 38

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro

<210> SEQ ID NO 39
<211> LENGTH: 17
<212> TYPE: PRT
<213> ORGANISM: Artificial Sequence
<220> FEATURE:
<223> OTHER INFORMATION: A synthetic amino acid linker

<400> SEQUENCE: 39

Val Ser Gln Thr Ser Lys Leu Thr Arg Ala Glu Thr Val Phe Pro Asp
1               5                   10                  15

Val

<210> SEQ ID NO 40
<211> LENGTH: 6
<212> TYPE: PRT
<213> ORGANISM: Artificial Sequence
<220> FEATURE:
<223> OTHER INFORMATION: A synthetic amino acid linker
```

<400> SEQUENCE: 40

Pro Leu Gly Leu Trp Ala
1               5

<210> SEQ ID NO 41
<211> LENGTH: 6
<212> TYPE: PRT
<213> ORGANISM: Artificial Sequence
<220> FEATURE:
<223> OTHER INFORMATION: A synthetic amino acid linker

<400> SEQUENCE: 41

Arg Val Leu Ala Glu Ala
1               5

<210> SEQ ID NO 42
<211> LENGTH: 10
<212> TYPE: PRT
<213> ORGANISM: Artificial Sequence
<220> FEATURE:
<223> OTHER INFORMATION: A synthetic amino acid linker

<400> SEQUENCE: 42

Glu Asp Val Val Cys Cys Ser Met Ser Tyr
1               5                   10

<210> SEQ ID NO 43
<211> LENGTH: 8
<212> TYPE: PRT
<213> ORGANISM: Artificial Sequence
<220> FEATURE:
<223> OTHER INFORMATION: A synthetic amino acid linker

<400> SEQUENCE: 43

Gly Gly Ile Glu Gly Arg Gly Ser
1               5

<210> SEQ ID NO 44
<211> LENGTH: 10
<212> TYPE: PRT
<213> ORGANISM: Artificial Sequence
<220> FEATURE:
<223> OTHER INFORMATION: A synthetic amino acid linker

<400> SEQUENCE: 44

Thr Arg His Arg Gln Pro Arg Gly Trp Glu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: A synthetic amino acid linker

<400> SEQUENCE: 45

Ala Gly Asn Arg Val Arg Arg Ser Val Gly
1               5                   10

<210> SEQ ID NO 46
<211> LENGTH: 9
<212> TYPE: PRT
<213> ORGANISM: Artificial Sequence
<220> FEATURE:
<223> OTHER INFORMATION: A synthetic amino acid linker

<400> SEQUENCE: 46

```
Arg Arg Arg Arg Arg Arg Arg Arg Arg
1               5

<210> SEQ ID NO 47
<211> LENGTH: 4
<212> TYPE: PRT
<213> ORGANISM: Artificial Sequence
<220> FEATURE:
<223> OTHER INFORMATION: A synthetic amino acid linker

<400> SEQUENCE: 47

Gly Phe Leu Gly
1

<210> SEQ ID NO 48
<211> LENGTH: 46
<212> TYPE: PRT
<213> ORGANISM: Artificial Sequence
<220> FEATURE:
<223> OTHER INFORMATION: A synthetic amino acid linker

<400> SEQUENCE: 48

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45

<210> SEQ ID NO 49
<211> LENGTH: 20
<212> TYPE: PRT
<213> ORGANISM: Artificial Sequence
<220> FEATURE:
<223> OTHER INFORMATION: A synthetic amino acid linker

<400> SEQUENCE: 49

Gly Gly Gly Gly Ser Gly Gly Gly Gly Ser Gly Gly Gly Gly Ser Gly
1               5                   10                  15

Gly Gly Gly Ser
            20

<210> SEQ ID NO 50
<211> LENGTH: 2
<212> TYPE: PRT
<213> ORGANISM: Artificial Sequence
<220> FEATURE:
<223> OTHER INFORMATION: A synthetic amino acid linker

<400> SEQUENCE: 50

Leu Glu
1

<210> SEQ ID NO 51
<211> LENGTH: 10
<212> TYPE: PRT
<213> ORGANISM: Artificial Sequence
<220> FEATURE:
<223> OTHER INFORMATION: A synthetic amino acid linker

<400> SEQUENCE: 51

Gly Gly Ser Ser Gly Gly Gly Ser Gly Gly
1               5                   10
```

```
<210> SEQ ID NO 52
<211> LENGTH: 4
<212> TYPE: PRT
<213> ORGANISM: Artificial Sequence
<220> FEATURE:
<223> OTHER INFORMATION: A synthetic amino acid linker

<400> SEQUENCE: 52

Gly Gly Gly Ser
1

<210> SEQ ID NO 53
<211> LENGTH: 735
<212> TYPE: PRT
<213> ORGANISM: Adeno-associated virus

<400> SEQUENCE: 53

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Arg
65                  70                  75                  80

Gln Leu Asp Ser Gly Asp Asn Pro Tyr Leu Lys Tyr Asn His Ala Asp
                85                  90                  95

Ala Glu Phe Gln Glu Arg Leu Lys Glu Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Glu Pro Val Lys Thr Ala Pro Gly Lys Lys Arg Pro
    130                 135                 140

Val Glu His Ser Pro Val Glu Pro Asp Ser Ser Ser Gly Thr Gly Lys
145                 150                 155                 160

Ala Gly Gln Gln Pro Ala Arg Lys Arg Leu Asn Phe Gly Gln Thr Gly
                165                 170                 175

Asp Ala Asp Ser Val Pro Asp Pro Gln Pro Leu Gly Gln Pro Pro Ala
            180                 185                 190

Ala Pro Ser Gly Leu Gly Thr Asn Thr Met Ala Thr Gly Ser Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Thr Trp Met Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Ser Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Arg Leu Asn Phe Lys Leu Phe Asn Ile Gln Val Lys
305                 310                 315                 320
```

```
Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 54
<211> LENGTH: 598
<212> TYPE: PRT
<213> ORGANISM: Adeno-associated virus

<400> SEQUENCE: 54

Met Ala Pro Gly Lys Lys Arg Pro Val Glu His Ser Pro Val Glu Pro
1               5                   10                  15

Asp Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
            35                  40                  45

Gln Pro Leu Gly Gln Pro Pro Ala Ala Pro Ser Gly Leu Gly Thr Asn
50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

```
Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
            405                 410                 415

Ile Glu Lys Val Met Ile Thr Asp Glu Glu Ile Arg Thr Thr Asn
        420                 425                 430

Pro Val Ala Thr Glu Gln Tyr Gly Ser Val Ser Thr Asn Leu Gln Arg
            435                 440                 445

Gly Asn Arg Gln Ala Ala Thr Ala Asp Val Asn Thr Gln Gly Val Leu
        450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
            485                 490                 495

Met Gly Gly Phe Gly Leu Lys His Pro Pro Gln Ile Leu Ile Lys
        500                 505                 510

Asn Thr Pro Val Pro Ala Asn Pro Ser Thr Thr Phe Ser Ala Ala Lys
            515                 520                 525

Phe Ala Ser Phe Ile Thr Gln Tyr Ser Thr Gly Gln Val Ser Val Glu
        530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
            565                 570                 575

Val Asp Thr Asn Gly Val Tyr Ser Glu Pro Arg Pro Ile Gly Thr Arg
        580                 585                 590

Tyr Leu Thr Arg Asn Leu
        595

<210> SEQ ID NO 55
<211> LENGTH: 533
<212> TYPE: PRT
<213> ORGANISM: Adeno-associated virus

<400> SEQUENCE: 55

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
            85                  90                  95

Leu Ile Asn Asn Asn Trp Gly Phe Arg Pro Lys Arg Leu Asn Phe Lys
        100                 105                 110

Leu Phe Asn Ile Gln Val Lys Glu Val Thr Gln Asn Asp Gly Thr Thr
    115                 120                 125

Thr Ile Ala Asn Asn Leu Thr Ser Thr Val Gln Val Phe Thr Asp Ser
        130                 135                 140

Glu Tyr Gln Leu Pro Tyr Val Leu Gly Ser Ala His Gln Gly Cys Leu
```

```
                145                 150                 155                 160
Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
                180                 185                 190

Leu Glu Tyr Phe Pro Ser Gln Met Leu Arg Thr Gly Asn Asn Phe Thr
                195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
                260                 265                 270

Arg Asn Trp Leu Pro Gly Pro Cys Tyr Arg Gln Gln Arg Val Ser Lys
                275                 280                 285

Thr Ser Ala Asp Asn Asn Asn Ser Glu Tyr Ser Trp Thr Gly Ala Thr
                290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
                340                 345                 350

Glu Lys Val Met Ile Thr Asp Glu Glu Glu Ile Arg Thr Thr Asn Pro
                355                 360                 365

Val Ala Thr Glu Gln Tyr Gly Ser Val Ser Thr Asn Leu Gln Arg Gly
                370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
                420                 425                 430

Gly Gly Phe Gly Leu Lys His Pro Pro Pro Gln Ile Leu Ile Lys Asn
                435                 440                 445

Thr Pro Val Pro Ala Asn Pro Ser Thr Thr Phe Ser Ala Ala Lys Phe
    450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
                500                 505                 510

Asp Thr Asn Gly Val Tyr Ser Glu Pro Arg Pro Ile Gly Thr Arg Tyr
                515                 520                 525

Leu Thr Arg Asn Leu
    530

<210> SEQ ID NO 56
<211> LENGTH: 738
<212> TYPE: PRT
<213> ORGANISM: Adeno-associated virus
```

<400> SEQUENCE: 56

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr

```
            405                 410                 415
Thr Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
                515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 57
<211> LENGTH: 737
<212> TYPE: PRT
<213> ORGANISM: Adeno-associated virus

<400> SEQUENCE: 57

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
```

```
                35                  40                  45
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
                180                 185                 190

Pro Ala Ala Pro Ser Ser Val Gly Ser Gly Thr Val Ala Ala Gly Gly
                195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
                370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ala
                435                 440                 445

Arg Thr Gln Ser Asn Pro Gly Gly Thr Ala Gly Asn Arg Glu Leu Gln
450                 455                 460
```

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 58
<211> LENGTH: 14
<212> TYPE: PRT
<213> ORGANISM: Artificial Sequence
<220> FEATURE:
<223> OTHER INFORMATION: A synthetic amino acid sequence
<221> NAME/KEY: SITE
<222> LOCATION: 4
<223> OTHER INFORMATION: Xaa = any amino acid
<221> NAME/KEY: SITE
<222> LOCATION: 9,11
<223> OTHER INFORMATION: Xaa = Y or W
<221> NAME/KEY: SITE
<222> LOCATION: 10,12,13
<223> OTHER INFORMATION: Xaa = any amino acid

<400> SEQUENCE: 58

Asn Pro Leu Xaa Asp Gln Tyr Leu Xaa Xaa Xaa Xaa Xaa Thr
1               5                   10

<210> SEQ ID NO 59
<211> LENGTH: 11

```
<212> TYPE: PRT
<213> ORGANISM: Artificial Sequence
<220> FEATURE:
<223> OTHER INFORMATION: A synthetic amino acid sequence
<221> NAME/KEY: SITE
<222> LOCATION: (1)...(5)
<223> OTHER INFORMATION: Xaa = any amnio acid
<221> NAME/KEY: SITE
<222> LOCATION: 6
<223> OTHER INFORMATION: Xaa = K or
<221> NAME/KEY: SITE
<222> LOCATION: 8
<223> OTHER INFORMATION: Xaa = W or Y
<221> NAME/KEY: SITE
<222> LOCATION: 9
<223> OTHER INFORMATION: Xaa = any amnio acid
<221> NAME/KEY: SITE
<222> LOCATION: 10
<223> OTHER INFORMATION: Xaa = P or T

<400> SEQUENCE: 59

Xaa Xaa Xaa Xaa Xaa Xaa Asn Xaa Xaa Xaa Gly
1               5                   10
```

PROGRAMMABLE ASSEMBLY OF VIRUS COMPOSITES FOR RECEPTOR-TARGETED GENE DELIVERY

CROSS-REFERENCE TO RELATED APPLICATIONS

This application is a U.S. National Stage Application under 35 U.S.C. 371 from International Application Serial No. PCT/US2018/057119, filed on Oct. 23, 2018, and published as WO 2019/084015 A1 and published on May 2, 2019, which claims the benefit of the filing date of U.S. application Ser. No. 62/575,722, filed on Oct. 23, 2017, the disclosures of which is are incorporated by reference herein.

BACKGROUND

Molecular approaches to treat cancer (predominantly chemotherapy) are often ineffective and cause severe side effects owing to the non-targeted mode of action. It is difficult to achieve an effective dose of a chemotherapeutic compound in cancer cells without also affecting bystander cells. Recognizing that target selectivity is arguably the most important contributor to making an effective and safe treatment, several lines of research have studied conjugation of highly potent cytotoxic drugs to antibodies that target antigens highly expressed on the surface of cancer cells, but not healthy cells (Sievers et al., 2013). While several of these Antibody-Drug-Conjugates (ADC) are now approved for cancer therapy, challenges remain, such as limitation to a single mode of action (cytotoxcity), widely varying efficacy as a function of antigen expression, and a paucity of conjugation-chemistries and linker design that minimize systemic release while maximizing release after uptake by a cancer cell.

Unlike molecular therapies in which the reagents are eventually cleared from the body, cell-based therapies combine the selectivity of antibodies and other binding proteins with long-term persistence. They have come a long way from the earliest allogeneic hematopoietic grafts (Weiden et al., 1979) to recent breakthroughs with engineering T cells to express chimeric antigen receptors (T-CAR) (Porter et al., 2011a). Recognizing that cancer specific antigens are rare, a new generation of dual-mode CAR-Ts were recently developed that emphasize a unique strength of cellular systems: the ability to do logic; to require two or more antigens coinciding on the same cell before eliciting a pre-programmed response. Clinical trials to treat B cell lymphomas and leukemia have shown promising results and many more studies are underway. Significant barriers remain, including the need for ex vivo modification and expansion of T cells and the need to determine which T cell population to target. The need for pheresis and ex vivo expansion is in great part due to a lack of precise and effective gene delivery methods that can target subset of lymphocytes in vivo. At the same time, collected patient blood might contain too few highly replicative T cell types, which some studies have suggest are ideal targets for Autologous Cell Transplants (Hinrichs et al., 2009; Berger et al., 2008; Paulos et al., 2010; Gattinoni et al., 2011).

In recent years, adeno-associated virus (AAV) has emerged as a viral gene delivery that is safe in humans, able to infect both dividing and arrested cells, and drive long-term expression (>6 months). About 30% of all gene therapy clinical trials use AAV; for trials started in the last two years, that number is approaching 60% (clinicaltrials.gov). However, most known AAV serotypes have broad tropism, making it hard to limit expression of therapeutic transgenes only to the therapeutic target (e.g., cancer), and not healthy cells. In an effort to alter AAV tropism, several groups have been able to display scFV and DARPINs on AAV capsids as genetic fusions to viral capsid proteins (Munch et al., 2012; Hagen et al., 2014; Munch et al., 2015). In several instances this modification was sufficient to redirect tropism toward specific cancer cell markers. However, only a few binding protein scaffolds have proven to be compatible with this approach as large fusions to capsid protein interferes with the delicate supramolecular viral packaging process (Kronenberg et al., 2005). In essence, without extensive case-by-case optimization, there is no generalizable and scalable way to engineer cell type specificity by generating AAVs that display a specific binding protein.

SUMMARY

This disclosure enables modular retargeting of viruses such as adeno-associated virus (AAV) towards virtually any receptor for which receptor-specific binding molecules (targeting molecules) such as antibodies are available. In one embodiment, a genetic modification is made to the capsid coding region to remove the endogenous tropism of the virus. In one embodiment, a genetic modification is made to the capsid coding region to interrupt and neutralize the endogenous tropism by introducing into the coding region sequences that when expressed as protein domain, covalently bind single strand DNA (ssDNA) in a sequence specific and non-overlapping (orthogonal) fashion. In one embodiment, a genetic modification is made to the capsid coding region to remove the endogenous tropism of the virus and another genetic modification is made to introduce into capsid protein domains that covalently bind ssDNA in a sequence specific and non-overlapping fashion. In one embodiment, by linking different monoclonal antibodies (mAB) to one of the ssDNA, which nucleotides may be modified, e.g., with peptide nucleic acid (PNA) or locked nucleic acid (LNA), and then combining the mAB/ssDNA with virus having the modified capsid, the virus becomes decorated with a selected antibody to form covalent mAB/virus composites. This approach extends to other receptor-specific binding proteins (e.g., nanobodies, Darpin. Affibodies, etc.) or non-antibody based proteins.

In one embodiment, AAV viral capsid proteins including proteins VP1 or VP2 are modified to incorporate a specific class of ssDNA-binding domains, e.g., from HUH endonucleases, and ssDNA oligonucleotide conjugated antibodies are then reacted with these ssDNA-binding domains to form mAB-AAV composites.

This disclosure also provides a method of rapidly and covalently conjugating a targeting molecule, e.g., an antibody, to a pre-assembled viral capsid. While other groups have incorporated antibodies and other targeting molecules into viral capsids, previous approaches were not generalizable and required case-by-case protein and genetic engineering of the viral vectors. The present approach, in contrast, does not have these limitations; it is generalizable, follows a predictable and programmable logic, and is not specific to one targeting molecule. A user-programmable process of 'arming' viral vectors with targeting molecule, e.g., antibodies, has several useful characteristics: 1) removing the broad tropism observed with some viruses, e.g., many AAV serotypes, that can cause undesirable off-target expression, 2) leveraging targeting molecules such as antibodies to mediate much more precise and engineer-able virus targeting, 3) any targeting molecule is compatible with this process, 4) since re-targeting of viral gene delivery would only require decorating virus with a different targeting molecule and no modification of the virus itself, off-the shelf 'unarmed' viral stocks could be pre-made and bio-banked, thus removing repeated labor-intensive virus production, and 5) complex mixtures of viral particles targeting different receptors and delivering different transgenes to specific sets of cells can be assembled in a single reaction according to a predictable logic: target molecule binds to viral particles, e.g., in a DNA sequence-specific manner, and form an irreversible targeting molecule/virus adduct. Thus, the system enables rapid, covalent attachment of a targeting molecule to the adaptor-modified viral capsid. The use of a stable covalently linked HUH-tag in this context provides for a linkage between the targeting molecule and the viral capsid that is completely covalent.

This disclosure also provides a method of highly-specific gene delivery. Due to the properties of the attachment technology (the ability to use virtually any targeting molecule and the covalent linkage between targeting molecule and capsid), the efficacy of gene delivery to many different antigens in an animal model can be rapidly tested. This enables development of new clinical gene therapies in a relatively short timeline. Moreover, the system may be used in veterinary applications.

In one embodiment, this disclosure provides a population of infectious recombinant virus with altered tropism, comprising: recombinant virus comprising a modified viral capsid and a viral genome, wherein at least one modification in the viral capsid provides the altered tropism which is altered relative to a corresponding virus without the modification in the viral capsid, and/or wherein the modified viral capsid comprises an insertion that includes one or more HUH domains optionally flanked at one or more ends by one or more linkers. In one embodiment, wherein at least one modification in the viral capsid that alters tropism is a deletion of one or more amino acids. In one embodiment, the deletion is 2, 3, 4, 5, or 10 amino acids or less than 50 amino acids. In one embodiment, the insertion alters the tropism. In one embodiment, the virus is adeno-associated virus (AAV). In one embodiment, the deletion in the AAV capsid includes one or more residues of the heparin binding domain. In one embodiment, the deletion in the AAV capsid includes one or more of residues 587-590 of the AAV capsid proteins, VP1, VP2, and/or VP3 (the heparin binding domain). In one embodiment, the insertion in the AAV capsid is at residue T456 or T457, or from residue Q586 to Q591 in VP1. In one embodiment, the insertion in the AAV capsid is at residue T456 or T457, or from residue Q586 to Q591 in VP1, VP2, and VP3. In one embodiment, the virus is adenovirus, sindbis virus or vesicular stomatitis virus (VSV). In one embodiment, the one or more HUH domains have a sequence having at least 80% amino acid sequence identity to a HUH domain in one or more of SEQ ID Nos. 2-10 and 20-21. In one embodiment, the one or more HUH domains are flanked by at least one linker. In one embodiment, at least one HUH domain is flanked by two linkers. In one embodiment, the viral capsid includes an affinity tag, e.g., a His-tag, HA-tag, a FLAG-tag, or a Strep-tag, or other tags useful for affinity purification and isolation, e.g., to purify virions. In one embodiment, the population has a plurality of distinct recombinant viruses having a plurality of different HUH domains. In one embodiment, the recombinant viruses with different HUH domains have different viral genomes. In one embodiment, the recombinant viruses have the same HUH domain. In one embodiment, the viral genome is a recombinant genome having at least one expression cassette for an exogenous gene product. In one embodiment, the exogenous gene product is a prophylactic or therapeutic gene product, e.g., a cytotoxic gene product.

Also provided is a composition comprising a targeting molecule covalently linked to a substrate for HUH. In one embodiment, the targeting molecule comprises an antibody or an antigen binding portion thereof. In one embodiment, the HUH substrate comprises a peptide nucleic acid (PNA) or a locked nucleic acid (LNA).

Further provided is a method of targeting mammalian cells. In one embodiment, a population of infectious recombinant virus with altered tropism, comprising: recombinant virus comprising a modified viral capsid and a viral genome, wherein at least one modification in the viral capsid provides the altered tropism which is altered relative to a corresponding virus without the modification in the viral capsid, and/or wherein the modified viral capsid comprises an insertion that includes one or more HUH domains is combined with a HUH substrate for the one or more HUH domains covalently linked to a targeting molecule to form a conjugate, and the conjugate is contacted with mammalian cells, e.g., primate cells including human cells, or bovine, equine, canine, feline ovine, swine or caprine cells. In one embodiment, the targeting molecule is an antibody or an antigen binding portion thereof.

In addition, a system is provided. In one embodiment, the system includes a population of infectious recombinant virus with altered tropism, comprising: recombinant virus comprising a modified viral capsid and a viral genome, wherein at least one modification in the viral capsid provides the altered tropism which is altered relative to a corresponding virus without the modification in the viral capsid, and/or wherein the modified viral capsid comprises an insertion that includes one or more linkers and one or more HUH domains; and a substrate for the HUH. In one embodiment, the system further comprises a targeting molecule.

BRIEF DESCRIPTION OF FIGURES

FIG. 6A-B. In Vitro Infection Assay to determine composite nanobody/AAV target specificity, (A) mMobA-displaying AAV packaging a RFP protein payload was incubated with anti-GFP nanobody fused to SNAP protein in the absence (left panel) or presence (right) of cognate benzylguanine-modified ssDNA oligo. In the absence of oligo, no nanobody/AAV composites were formed (left panel), while they did in the presence of oligo (right panel) as confirmed by western blot (data not shown). Either reaction products were added to HEK293 cells expressing in the extracellular surface membrane-anchored GFP (green cells). Only GFP expressing cells to which nanobody/AAV composites were added (right panel) show expression of RFP (the AAV payload). This means that (1) Infection depends on the presence of targeting domain. AAV lacking a targeting domain (anti-GFP nanobody) is unable to infect any cell (target or non-target). (2) Infection is target-specific. Nanobody/AAV composites only infect cells that express the target molecule (GFP) but not off-target cells. (B) Further supporting the notion that nanobody/AAV composites are infecting cells in target-specific manner, is that GFP expression levels, and RFP expression levels are correlated. One interpretation of this correlation is that more GFP on the cells surface results in more virus binding and uptake, thus a higher apparent multiplicity of infection (MOI). Higher MOI result in more genome copies of transgenes delivered and thus higher transgene expression.

FIG. 8. Exemplary AAV VP sequences (SEQ ID Nos. 53-57).

FIGS. 10A-G. A description of exemplary plasmids employed in the production of recombinant AAV that is compatible with the formation of programmable AAV/antibody composites. The name of the plasmid is shown on the left. Shown to the right of the names is the DNA-level plasmid map, which includes promoters, genes, and other regulatory elements (e.g., WPRE, polyA etc.). Approximate position modifications are indicated by vertical lines. The protein products that are transcribed and translated from each plasmid are listed below. Splicing sites are connected by blue lines. (A) A transfer vector. The transgene that is flanked by the two ITR sites becomes packaged into the viral capsid. The CAG promoter is broadly active in many cell types. By replacing the CAG with other tissue- and cell-type specific promoters (e.g., murine stem cell virus, MSCV, or CD3δ) receptor-mediated viral infection can be combined with widely used means of restricting transgene expression. (B) The AAV-DJ rep/cap plasmid. A helper plasmid that drives the expression of replication factors and capsid proteins required for recombinant AAV production. (C-E) Expression constructs for individual capsid protein splice forms (VP1, VP2, and VP3) with the endogenous HBD domain replaced by a HA tag. One of these plasmids is used in combination with a binding scaffold or HUH presenting capsid (E-G) to produce recombinant AAV that displays on the capsid surface either a genetically encoded binding scaffold (e.g., nanobody, GP2) or a HUH domain.

Figure 11A:
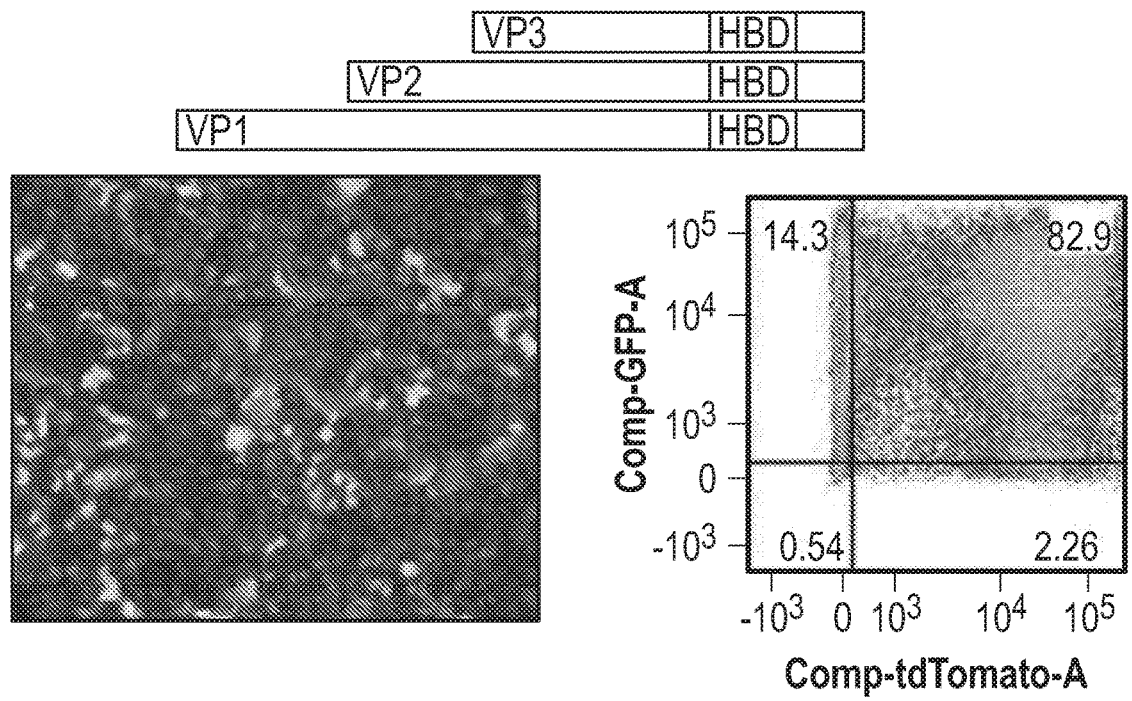
Figure 11B:
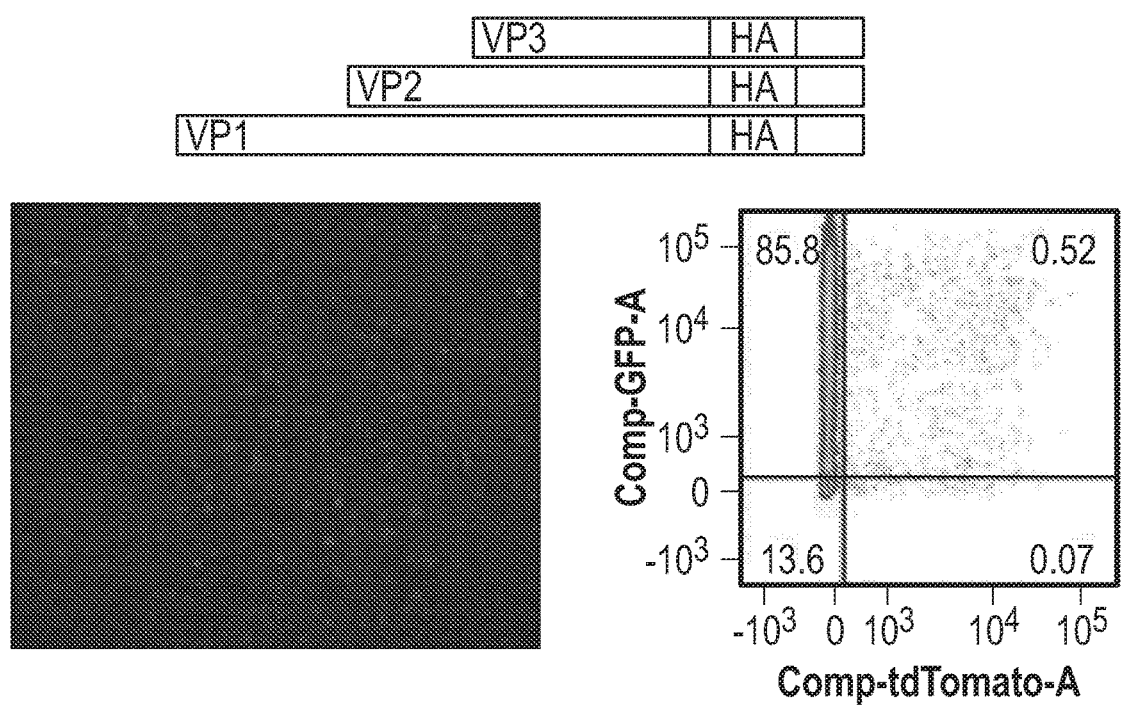

FIGS. 11A-B. A two step approach to remove and replace tropism. (A) Wild-type AAV-DJ capsid (Grimm et al., 20013) is composed of three capsid proteins VP1, VP2, and VP3 at a 1:1:10 ratio. HEK293FT cells are transduced at multiplicity of infection (MOI) $1\times10^6$ genome copies (g.c.)/cell. Transduction is reported by tdtomato expression (left panel, yellow). Cells nuclei are counter-stained with DAPI (blue). Right panel, flow analysis of WT AAV-DJ transduction. 83% of cells are transduced. (B) Replacing the HBD domain in AAV-DJ with a HA tag removed endogenous tropism. HEK293FT cells are transduced at multiplicity of infection (MOI) $1\times10^6$ genome copies (g.c.)/cell. Left panel, no transduction is observed. Cells nuclei are counter-stained with DAPI (blue). Right panel, flow analysis of ΔHBD AAV-DJ transduction. 0.5% of cells are transduced. All experiments were performed 48 hours after viral transduction.

Figures 12A, 12B:
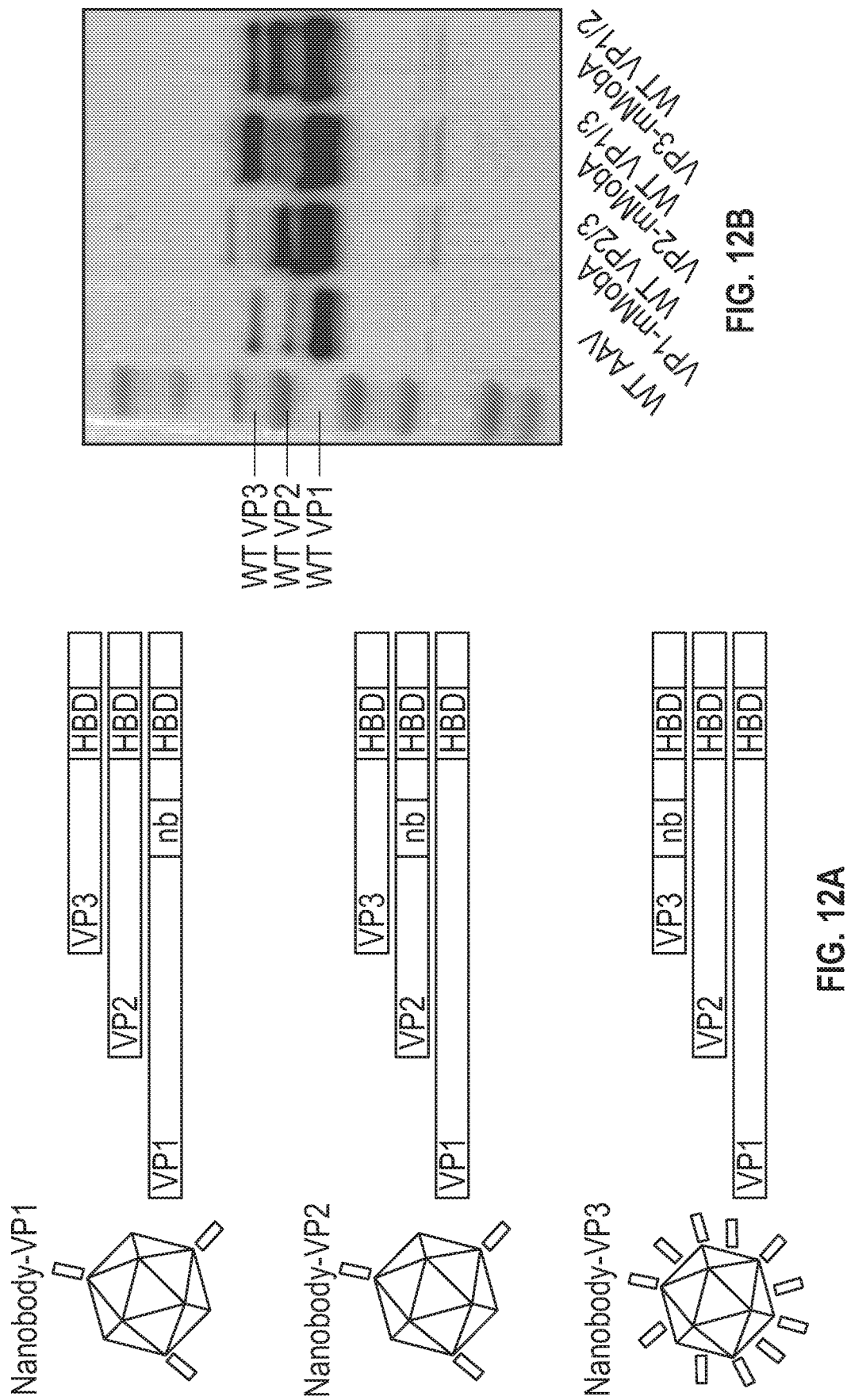

FIGS. 12A-B. Individual capsid protein splice forms can be modified, (A) By using different combinations of rep/cap plasmids, AAV capsid can be formed that carries modifications (e.g., nanobody, GP2, HUH) in only one of the capsid proteins. (B) Western blot analysis of WT AAV-DJ and recombinant modified AAVcapsid in which the mMobA HUH domain is added to either VP1, VP2, or VP3. Individual bands shift to larger molecular weight due to the addition of mMobA. In all cases capsid can form in the presence of the mMobA insertion and, relative ratios of VP1, VP2, and VP3 are comparable to WT AAV-DJ.

Figure 13A:
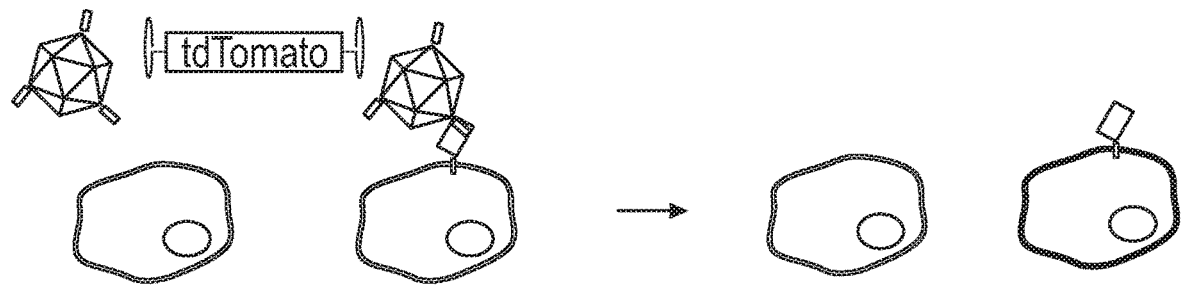
Figure 13B:
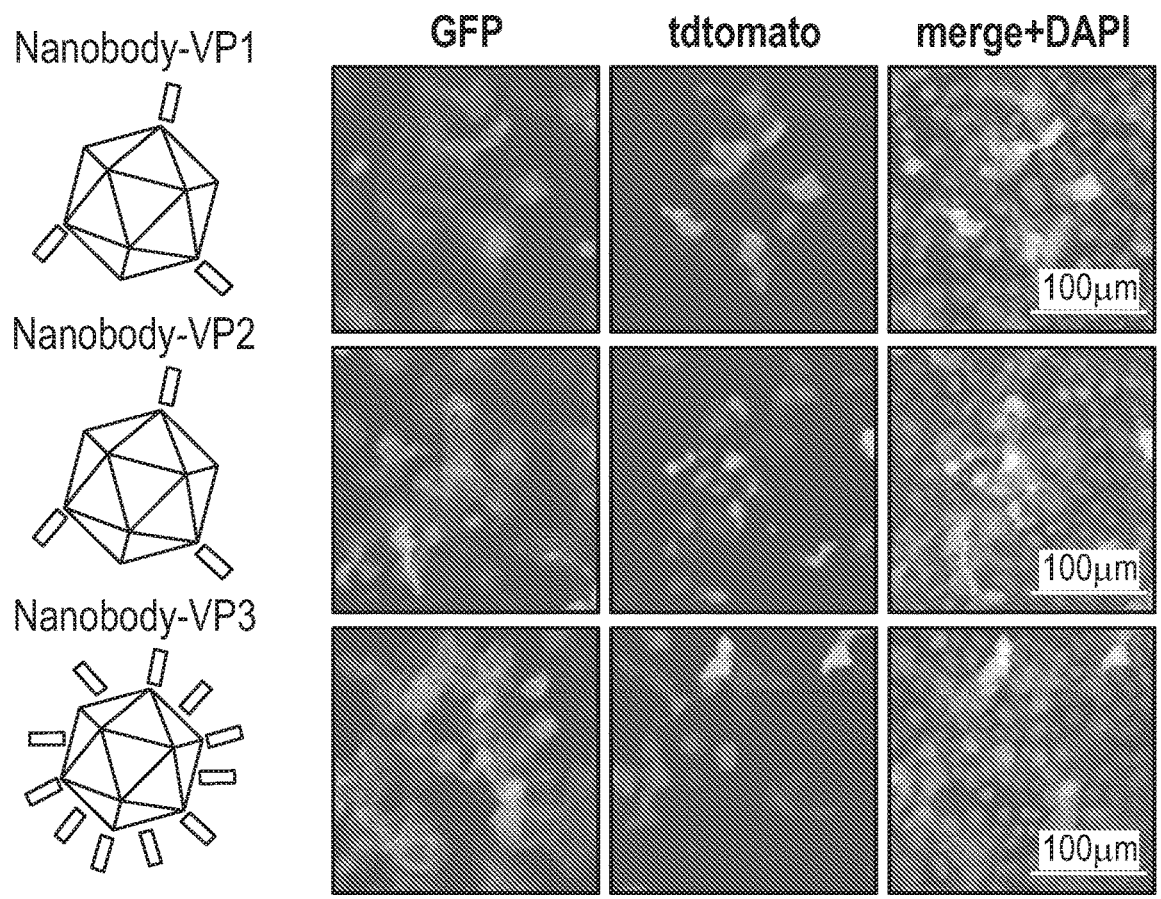
Figure 13C:
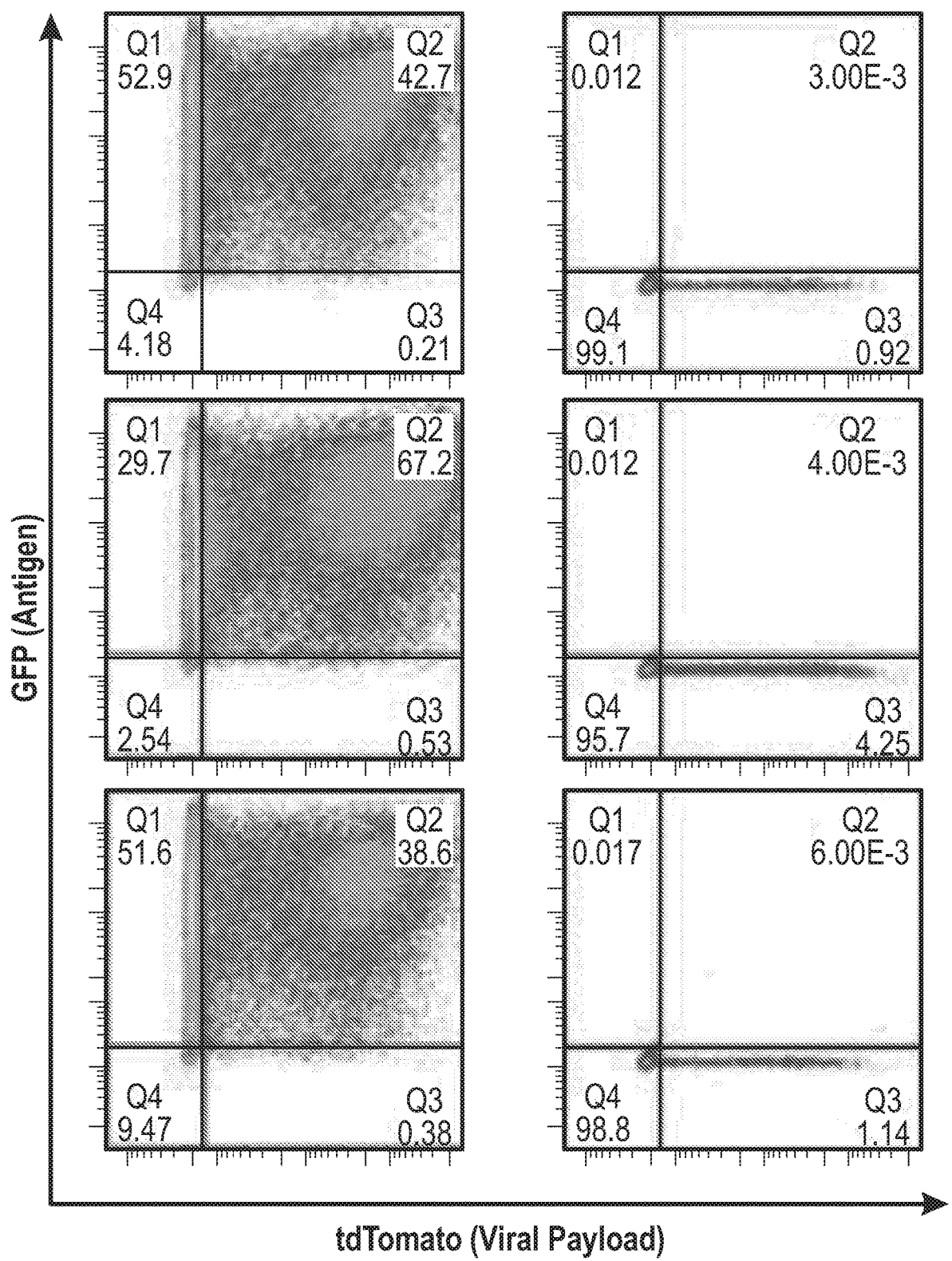

FIGS. 13A-C. Receptor-mediated infection in a synthetic system. (A) HEK239FT cells are transiently transduced to express GFP on the extracellular surface (via a GPI post-translational modification). An AAV-nanobody composite is produced that displays an anti-GFP nanobody on either VP1, VP2, or VP3. In each case the composite packages a tdtomato transgene. If infection is receptor-specific, only green (GFP-expressing) cells are expected to express tdtomato (indicating viral transduction). (B) Left, AAV-nb composite used in the experiment. Center, GFP channel, tdtomato channel, and overlay with DAPI shows only GFP positive cells are infected and express tdtomato. (C) Flow analysis. On target infection is 43%, 67%, and 39% for VP1-nb, VP2-nb, and VP3-nb, respectively. Off target infection is below 1% in every case.

Figure 14:
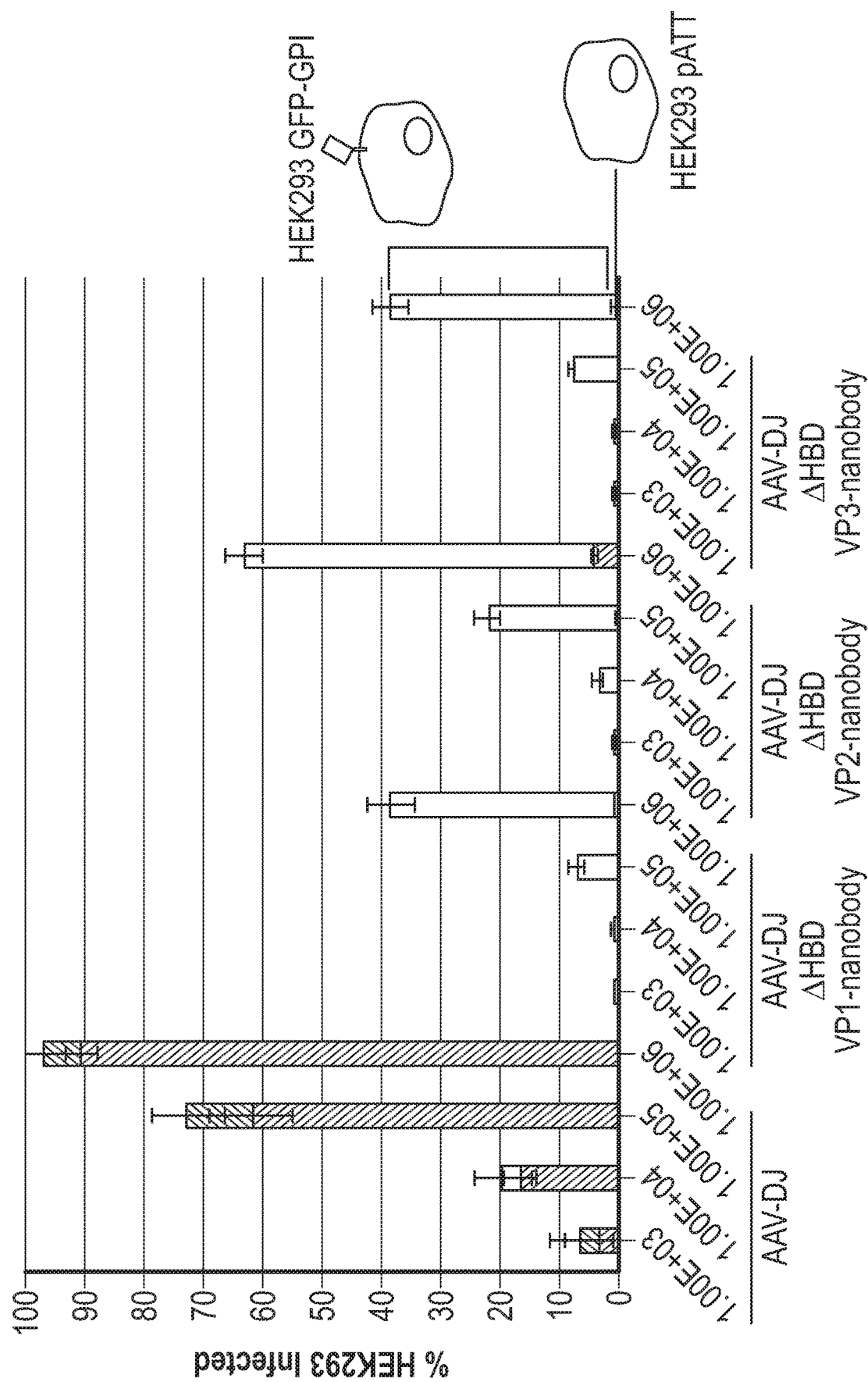

FIG. 14. Characterization of receptor-specificity for different MOI and different capsid modifications. Shown are stacked bar graphs indicating on target infection (green) and off-target infection (black). While AAV-DJ show no receptor-specificity, all nb-displaying AAVs are specific at any MOI and achieve near WT AAV infection levels.

Figure 15A:
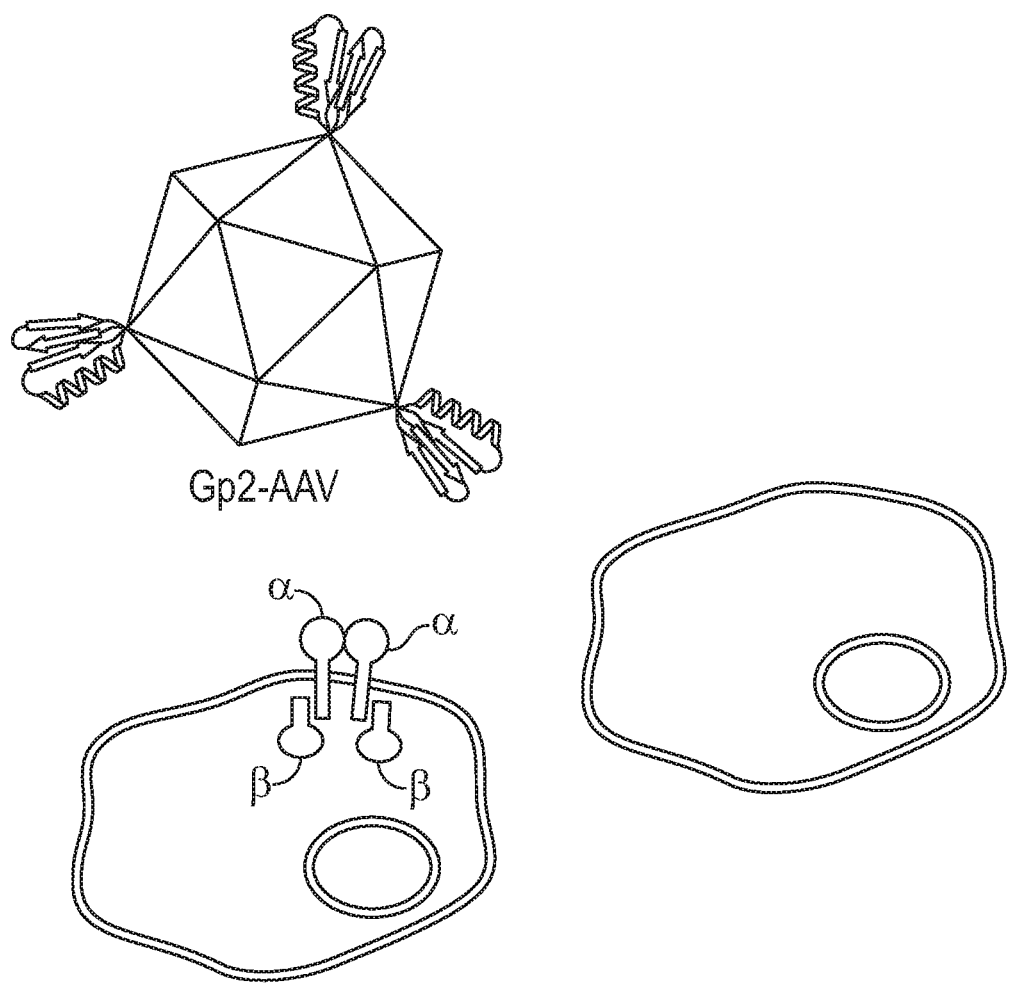
Figure 15B:
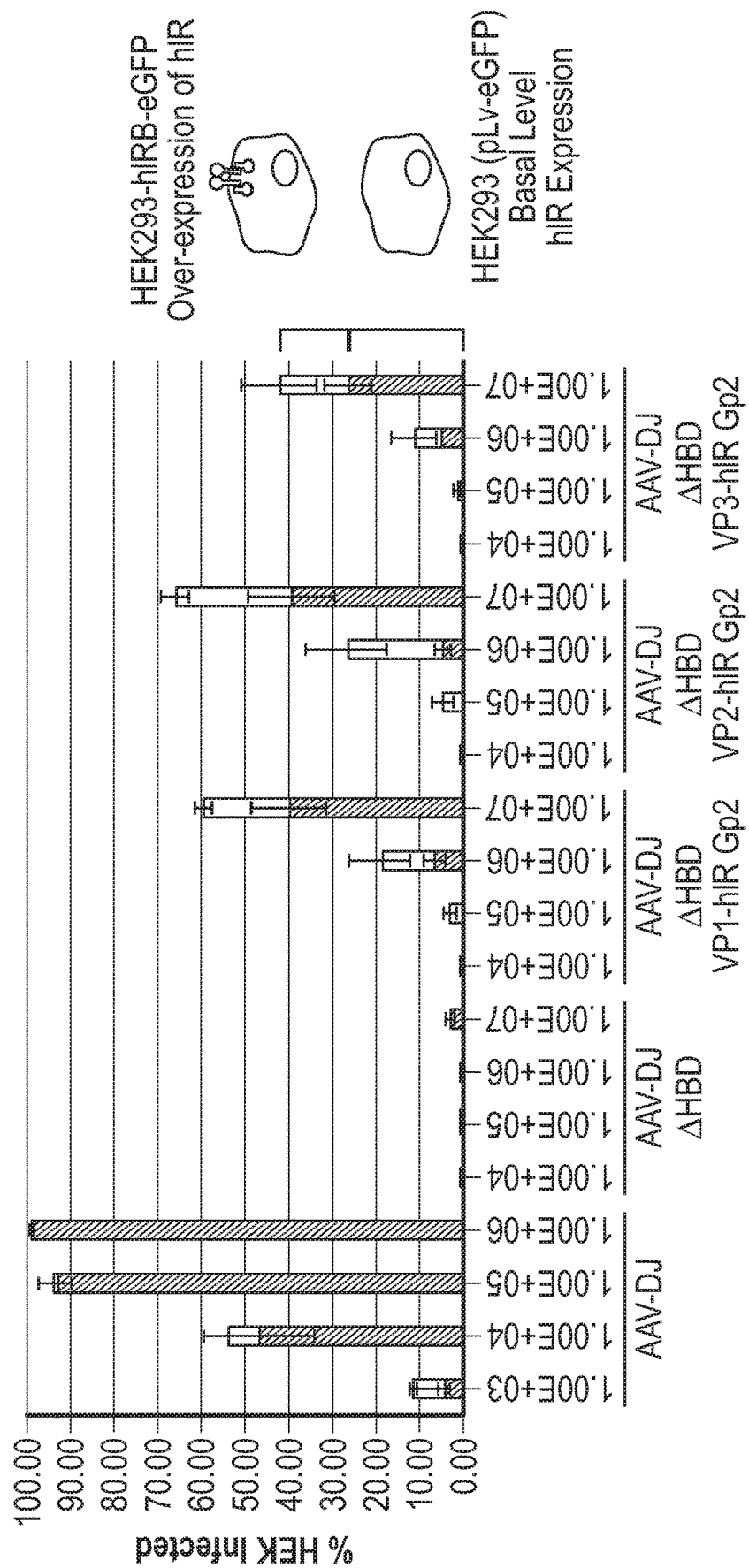
Figure 15C:
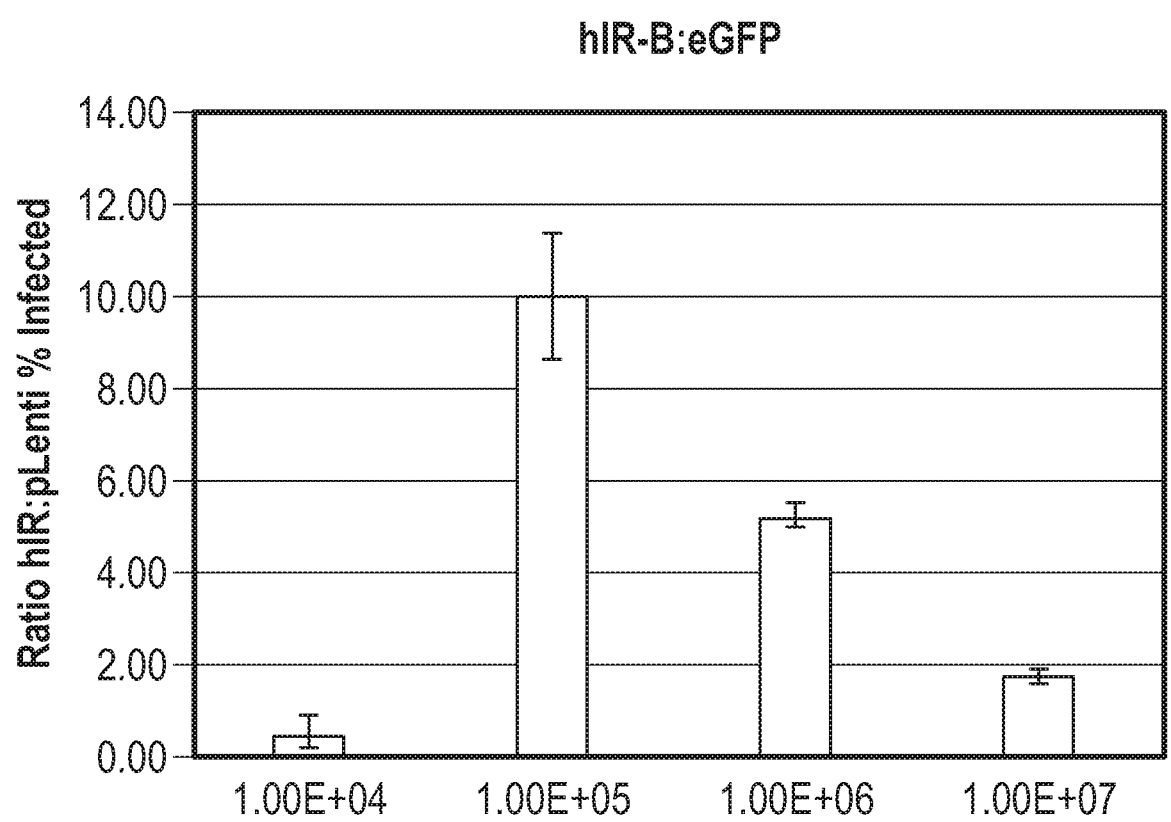

FIGS. 15A-C. Receptor-mediated transduction of a breast cancer model cell line. (A) A composite virus capsid is formed between ΔHBD AAV and binding scaffold based on the phage gene 2 (GP2) which selectively binds to human insulin receptor isoform B (hIR-B). Overexpression of hIR-B is a hallmark of many estrogen-receptor positive cancers. Specificity of infection is tested by incubating AAV-GP2 composites with a mixture of cells, some expressing hIR-B ('breast cancer'-like) and those that do not ('healthy cells'). Infection is reported by expression of tdtomato, the viral payload. (B) While WT AAV-DJ is infecting cells indiscriminately most MOI, and ΔHBD AAV in non-infective, presenting GP2 on either VP1. VP2, or VP3 provides for preferential transduction of hIR-B-positive cells. The observed off-target infection is due to basal expression of endogenous hIR-8 in HEK293 cells. (C) While off-target transduction is observed at high MOI, at lower MOI excellent specific can be achieved. For example, at a MOI of $1\times10^5$ g.c./cell, the ratio of on-target vs. off-target is 10-fold.

Figure 16B:
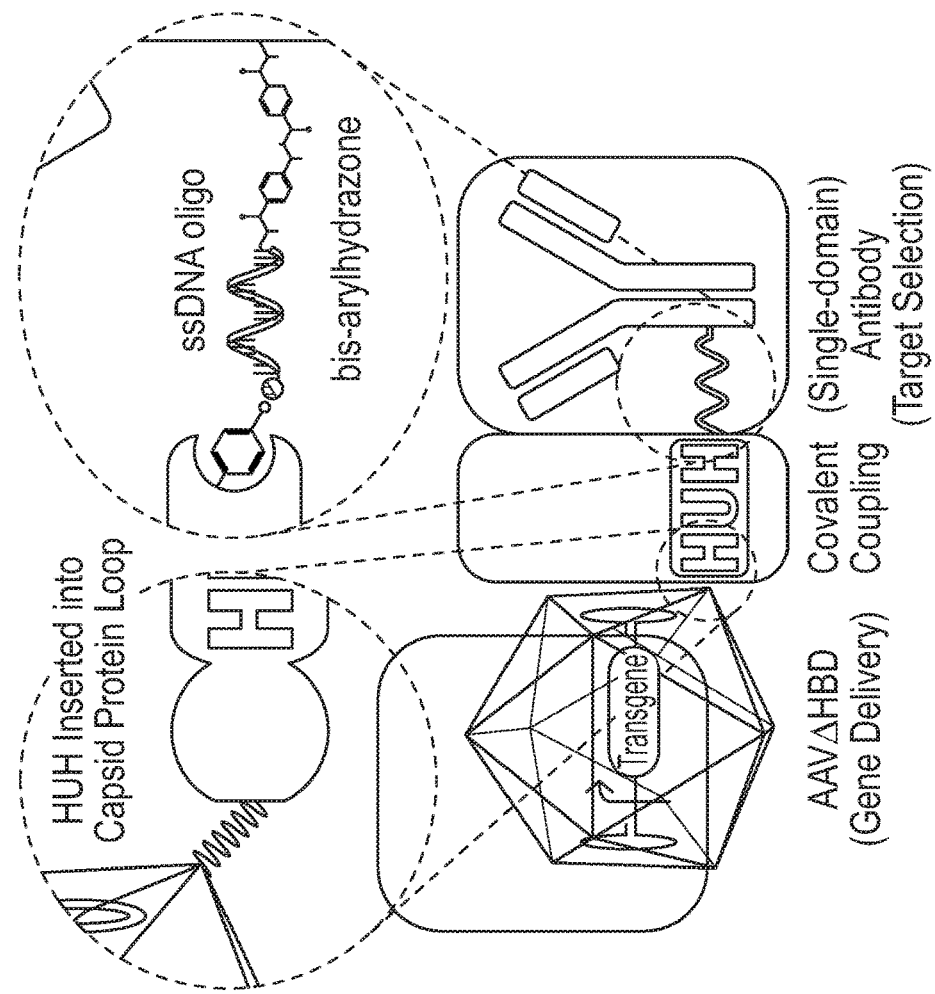
Figure 16A:
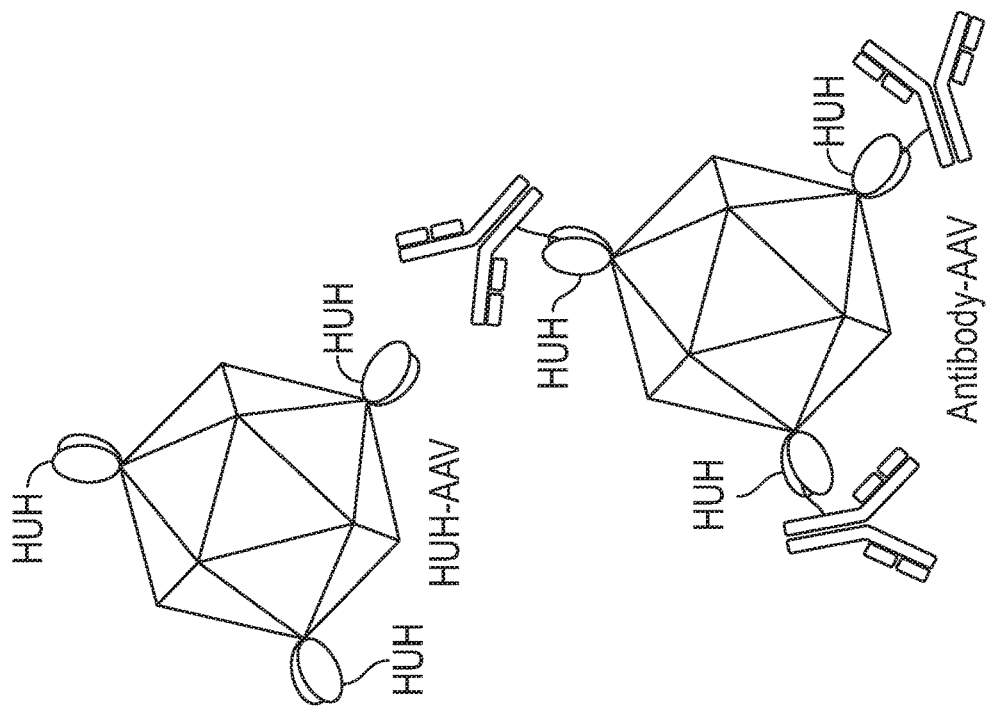

FIGS. 16A-B. How Antibody-AAV composites are formed. (A) Incorporating HUH domains into AAV capsid (HUH-AAV) allows for assembly of receptor-targeted viral vector through a predictable logic. The covalently linked antibody determines what type cell- and tissue-types the antibody-AAV composite infects. HUH-AAV can be pre-packaged and biobanked, before it is activated by 'arming' it with an antibody or other binding molecule. (B) The receptor-specific antibody is decorated with ssDNA via commercially available hydrazone-chemistry based oligonucleotide, conjugation kits (e.g., Innova Biosciences). A HUH domain specific to the oligo sequence used in this conjugation covalently attaches to this conjugated antibody via phosphotyrosine in the HUH domain's active site. If this HUH domain is covalently linked to the rcAAV capsid surface—through genetic engineering of capsid proteins VP1, VP2, and VPS—this results in covalently linked composite structures containing an AAV particle (packaging the delivered transgene) and an antibody that selectively binds cell-type specific surface markers.

Figure 17:
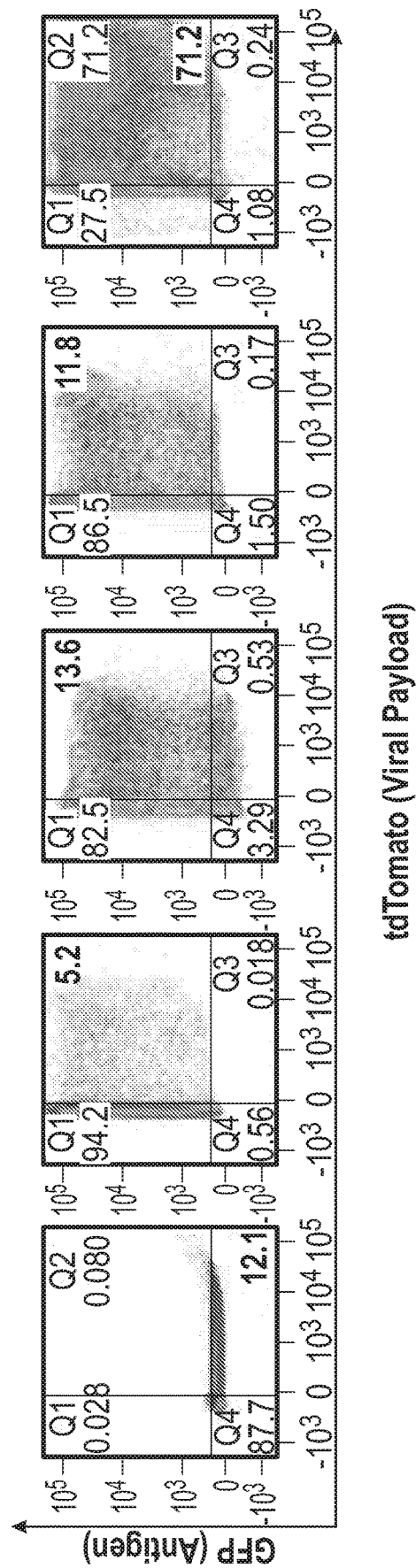

FIG. 17. Receptor-mediated transduction with antibody-AAV composites. HEK239FT cells are transiently transduced to express GFP on the extracellular surface (via a GPI post-translational modification). An AAV-antibody composite by covalently linking a commercially source anti-GFP antibody (Abcam) to ΔHBD AAV packaging tdtomato as the viral payload. Only when (1) the surface antigen (GFP) is present, (2) a HUH domain is incorporated. (3) antibody is conjugated with ssDNA, and (4) the antibody is linked to the capsid, are cell transduced at >70% efficiency. Observed off-target infection in great part stems from the HUH domain (compare panel 2 vs 1.3, and 4).

Figure 18:
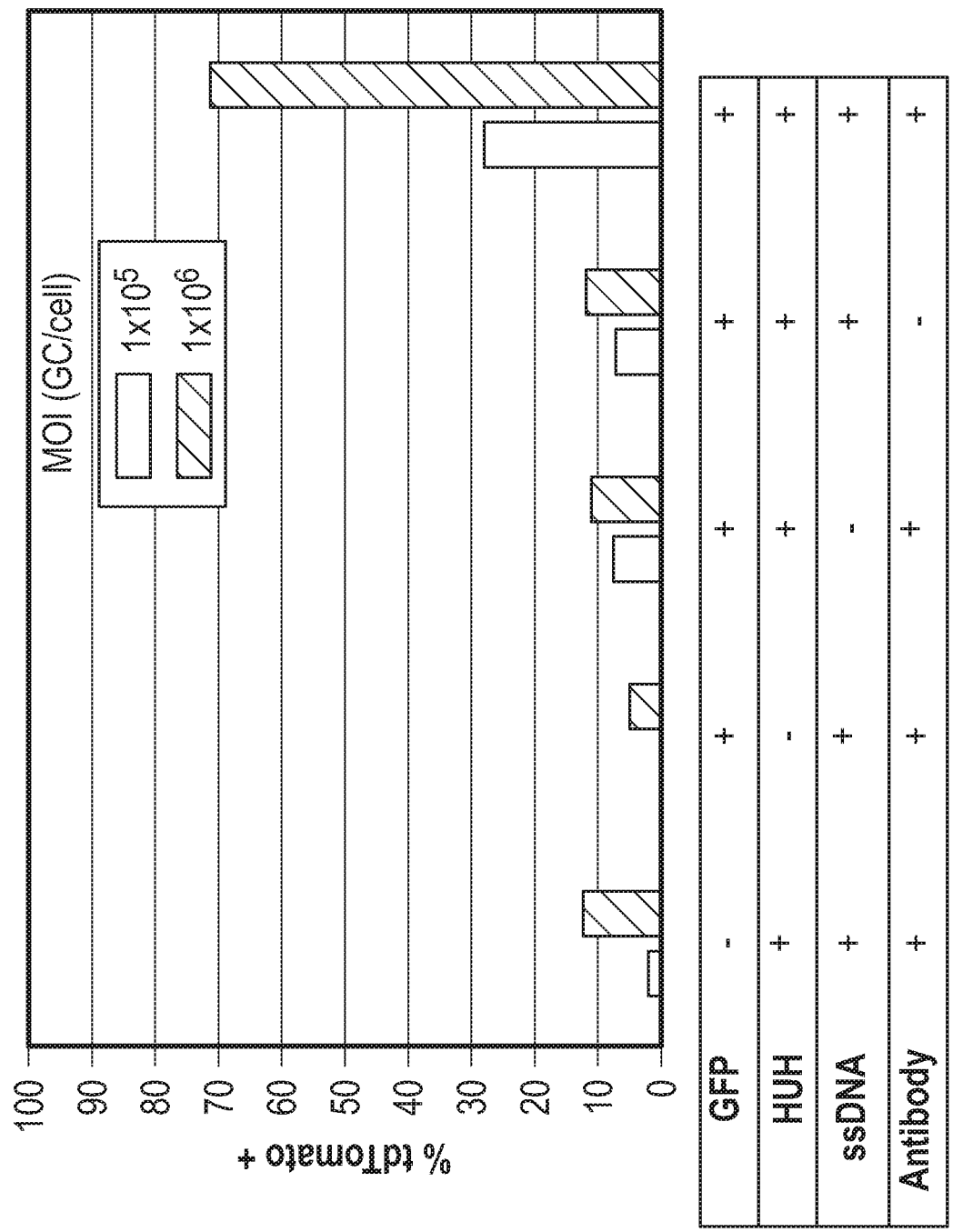

FIG. 18. On- and off-target infection scale favorably. Increasing MOI tenfold, from $1\times10^5$ to $1\times10^6$ g.c./cell greatly increases on-target infection (last group), while having only modest effects on off-target infection (first 4 groups).

Figure 19:
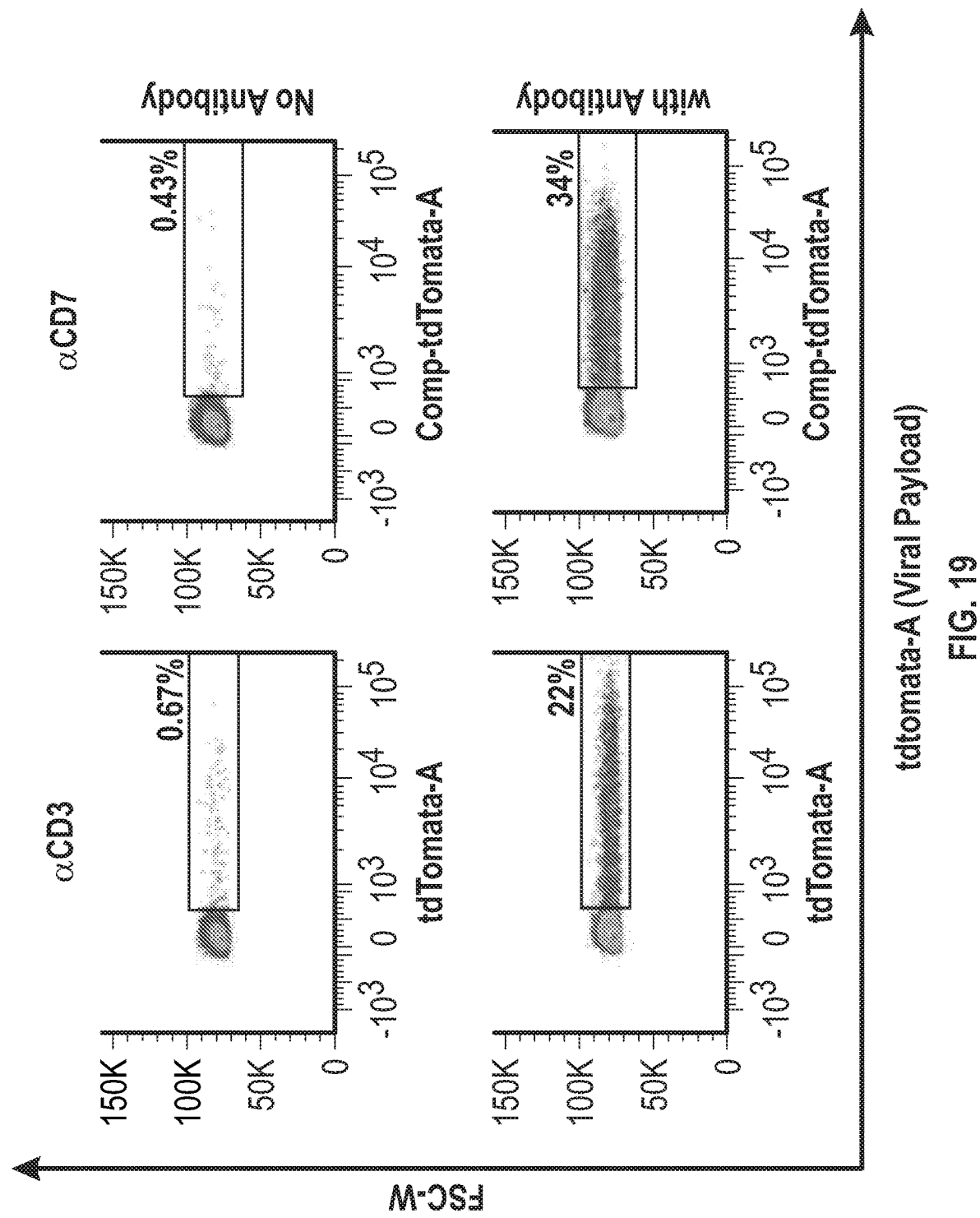

FIG. 19. The antibody-AAV composite approach is generalizable. Linking commercially available antibodies against surface receptors (CD3 and CD7) commonly expressed on Jurkat cell (a lymphocyte cell line) to ΔHBD AAV packaging tdtomato provides for high efficiency transduction. Less than 1% off-target infection was observed.

Figure 20A:
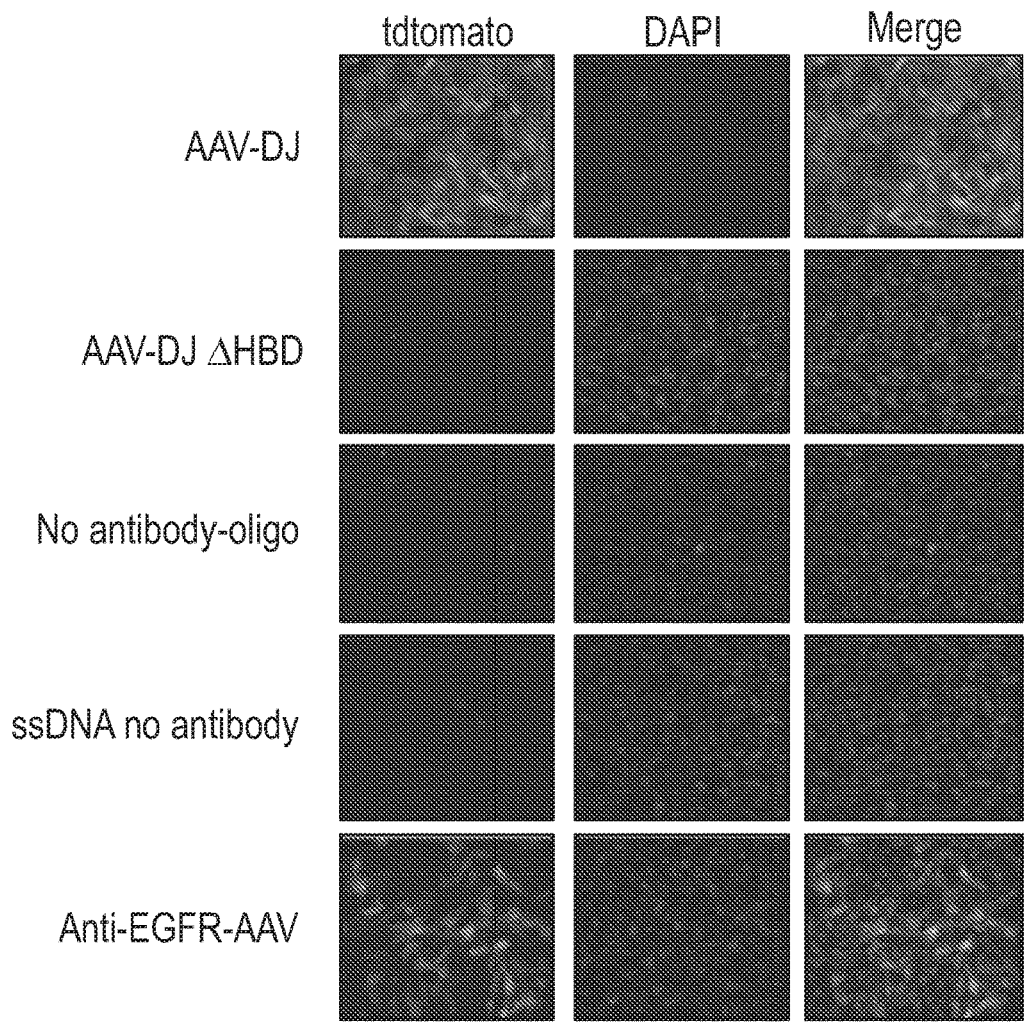
Figure 20B:
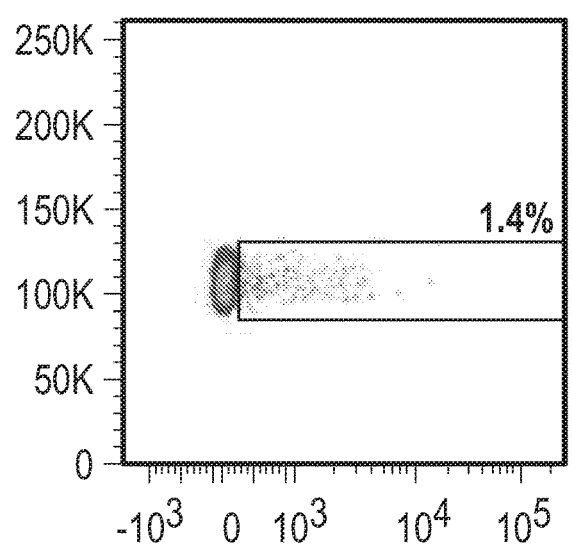
Figure 20C:
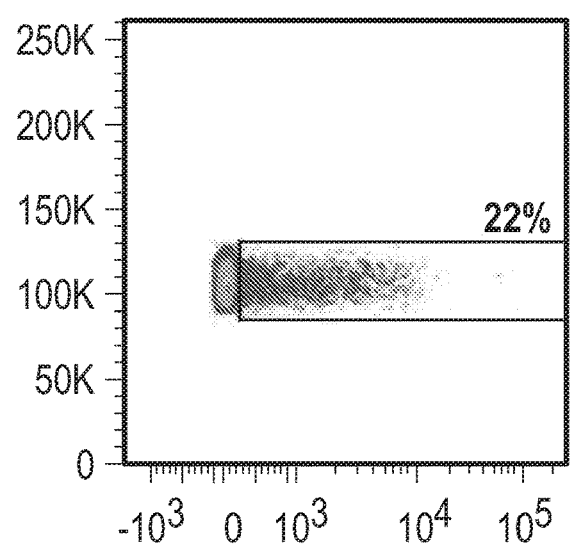
Figure 21A:
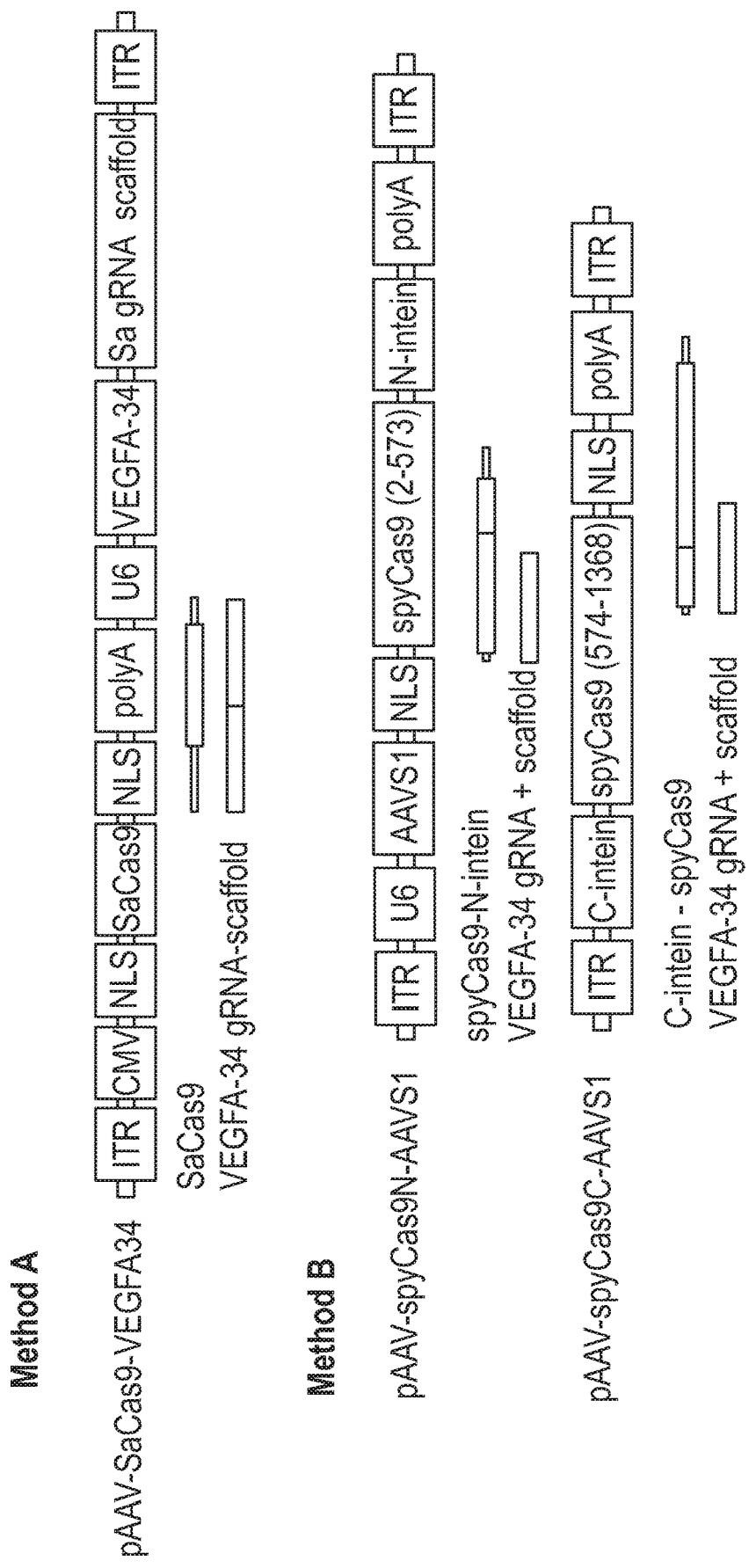
Figure 21C:
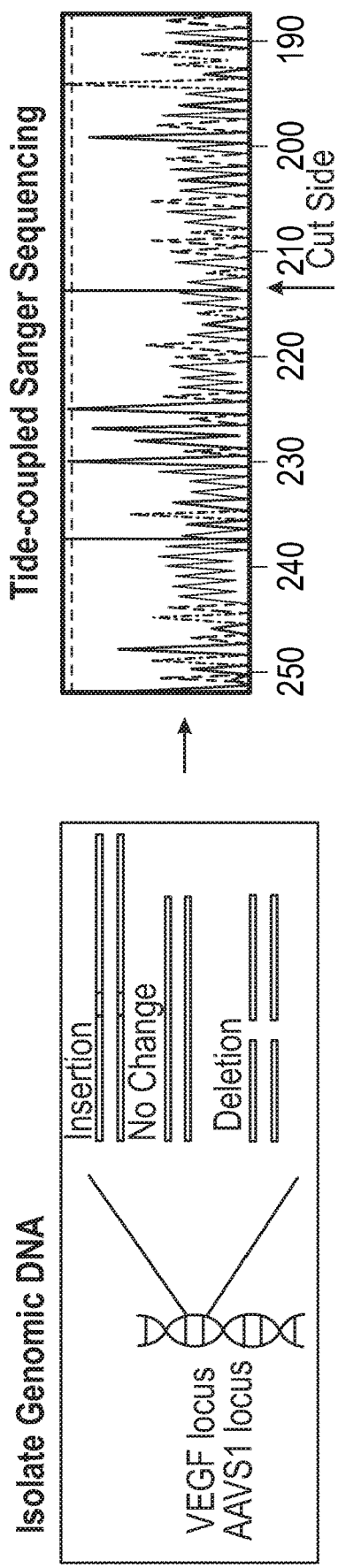

FIGS. 20A-C. EGFR-mediated transduction of U251 cells. (A) Epi-fluorescent imaging of U251 after 72 hours transduced with the indicated virus. Left panels are tdtomato reporter expression (the viral payload). Center panels are DAPI stained cell nuclei. Right panel are a merge of tdtomato and DAPI signal. Data show that WT AAV-DJ infects nearly all cells, and tropism null AAV (AAV-DJΔHBD) is non-infective. Composite AAVs formed with either ssDNA oligos or anti-EGFR antibody omitted were also non-infective. Only the fully formed anti-EGFR-AAV composite was able to transduce U251 cells. (B) Off-target infection (ΔHBD AAV packaging tdtomato without linked antibody) (C) On-target infection (ΔHBD AAV packaging tdtomato with anti-EGFR antibody).

FIGS. 21A-D. Two methods for receptor-mediated genome editing. (A) Method A: SaCas9 and VEGF-targeting gRNA (VEGFA-34) are encoded on the same plasmid along with the SaCas9 scaffold RNA. Method B: A split version of spyCas9 is encoded on two packaging plasmids along with an AAVS1-targeting gRNA. (B) The payload for Method A is packaged into a composite virus, which is then linked to an anti-CD3 antibody. Incubating this virus with Jurkat cells (expressing CD3) delivers both Cas9 and gRNA genes, which upon transcription and translation introduce indels at the AAVS1 locus. The payload for Method B is packaged into two different composite viruses, one modified with anti-CD3 and the other with anti-CD7. Incubating both viruses with Jurkat cells (expressing both CD3 and CD7) delivers both payloads into the same cell. Upon transcription and translation, inteins mediate protein ligation to reconstitute full-length spyCas9. A cell type that only expresses CD3 or CD7 only receives one half of the split Cas9. In this way Cas9 can be delivered to cell types or tissues that are defined by two overlapping surface markers. (C) To measure indel efficiency genomic DNA is isolated and subjected to TIDE coupled Sanger Sequencing. (D) Total indel efficiency was 16.7% and 22.2% for Method A (SaCas9) and 22.2% for Method B (split spy Cas9), respectively.

DETAILED DESCRIPTION

Definitions

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, viral vectors, e.g., adenovirus including helper-dependent adenovirus vectors, which do not express any adenovirus genes and are immunologically silent to allow for persistent expression, adeno-associated virus (AAV), e.g., an AAV-1, AAV-2, AAV-3, AAV-4, AAV-5, AAV-6, AAV-7, AAV-8, AAV-9, AAV-10, AAV-11 or AAV-12, and including pseudotyped viruses and non-natural serotypes such as AAV-D J (Grimm et al., *J. Virol.*, 82:5887 (2008)), and AAV-PHP.eB or AAV-PHP.S (Chan et al., *Nat. Neurosci.*, 20:1172 (2017)), the disclosures of which are incorporated by reference herein. Vectors can also comprise other components or functionalities that further modulate gene delivery and/or gene expression, or that otherwise provide beneficial properties to the cells to which the vectors will be introduced. Such other components include, for example, components that influence binding or targeting to cells; components that influence uptake of the vector nucleic acid by the cell; components that influence localization of the polynucleotide within the cell after uptake (such as agents mediating nuclear localization); and components that influence expression of the polynucleotide. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene"), e.g., via a recombinant virus, into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the cell if integrated into the genome or maintained extrachromosomally. Such a transgene may include a gene which is partly or entirely heterologous (i.e., foreign) to the transgenic host cell or organism, or may represent a gene homologous to an endogenous gene of the host cell or organism.

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are at least eight serotypes of primate AAVs, for example, AAV-1 to AAV-8. For example, serotype AAV2 is used to refer to an AAV which contains capsid proteins encoded from the cap gene of AAV 2 and a genome containing 5' and 3' ITR sequences from the same AAV2 serotype. The abbreviation "rAAV" refers to recombinant adeno-associated virus, also referred to as a recombinant AAV vector (or "rAAV vector").

A cell has been "transformed", "transduced", "transfected" or "genetically modified" by exogenous or heterologous nucleic acids when such nucleic acids have been introduced inside the cell. Transforming DNA may or may not be integrated (covalently linked) with chromosomal DNA making up the genome of the cell. In mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication.

The term "wild-type" with respect to a gene or gene product refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" or "variant" refers to a gene or gene product that displays modifications in sequence and or functional properties (i.e., altered characteristics) when compared to the wild-type gene or gene product. It is noted that naturally-occurring mutants can be isolated: these are identified by the fact that they have altered characteristics when compared to the wild-type gene or gene product.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3'(carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

The term "control elements" refers collectively to promoter regions, polyadenylation stimulations, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a cleavable or targeting peptide sequence is operably linked to another protein if the resulting fusion is cleaved into two or more parts as a result of cleavable sequence or is transported into an organelle as a result of the presence of an organelle targeting peptide.

"Homology" refers to the percent of identity between two polynucleotides or two polypeptides. For example, polypeptides, e.g., viral capsid protein, may have at least 50%, 55%, 60%, 65%, 70%, 75%, 80%, 85%, 90%, 92%, 95%, 96%, 97%, 98% or 99% amino acid sequence identity to a reference polypeptide sequence, e.g., have at least 50%, 55%, 60%, 65%, 70%, 75%, 80%, 85%, 90%, 92%, 95%, 96%, 97%, 98% or 99% amino acid sequence identity to any of Accession Nos. P03135 (AAV-2), AGA39530 (AAV-8), YP_077178.1 (AAV-7, AAS99264.1 (AAV-9), or AAC58045.1 (AAV-4). The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, at least about 90%, or at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination stimulation, may also be included.

The term "exogenous," when used in relation to a protein, gene or nucleic acid, e.g., polynucleotide, in a cell or organism refers to a protein, gene, or nucleic acid which has been introduced into the cell or organism by artificial or natural means, or in relation to a cell refers to a cell which was isolated and subsequently introduced to other cells or to an organism by artificial or natural means (a "donor" cell).

An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "peptide", "polypeptide and protein" are used interchangeably herein unless otherwise distinguished to refer to polymers of amino acids of any length. These terms also include proteins that are post-translationally modified through reactions that include glycosylation, acetylation and phosphorylation.

The term "linked" in the context of polypeptide sequences includes a linkage introduced through recombinant means or chemical means.

The terms "effective amount" or "amount effective to" or "therapeutically effective amount" refers to an amount sufficient to induce a detectable therapeutic response in the subject. Assays for determining therapeutic responses are well known in the art.

The terms "patient" or "subject" are used interchangeably and refer to a mammalian subject to be treated, for instance, a human patient. In some cases, the methods of the invention find use in experimental animals, in veterinary application, and in the development of animal models for disease, including, but not limited to, rodents including mice, rats, and hamsters; and primates.

As used herein, "administering" or "delivering" a molecule or treatment to a cell (e.g., a molecule such as a linear or circular nucleic acid optionally in a delivery vehicle) includes contacting the molecule with the cell, e.g., by mixing, fusing, transducing, transfecting, microinjecting, electroporating, or shooting. For instance, for in vivo delivery, a molecule may be delivered via a device such as a catheter, canula or needle.

The term "antibody," as used herein, refers to a full-length immunoglobulin molecule or an immunologically-active fragment of an immunoglobulin molecule such as the Fab or F(ab')2 fragment generated by, for example, cleavage of the antibody with an enzyme such as pepsin or co-expression of an antibody light chain and an antibody heavy chain in, for example, a mammalian cell, or ScFv. The antibody can also be an IgG, IgD, IgA, IgE or IgM antibody. Full-length immunoglobulin "light chains" (about 25 kD or 214 amino acids) are encoded by a variable region gene at the amino-terminus (about 110 amino acids) and a kappa or lambda constant region gene at the carboxy-terminus. Full-length immunoglobulin "heavy chains" (about 50 kD or 446 amino acids), are similarly encoded by a variable region gene (about 116 amino acids) and one of the other aforementioned constant region genes, e.g., gamma (encoding about 330 amino acids). Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. In each pair of the tetramer, the light and heavy chain variable regions are together responsible for binding to an antigen, and the constant regions are responsible for the antibody effector functions. In addition to naturally occurring antibodies, immunoglobulins may exist in a variety of other forms including, for example, Fv, ScFv, Fab, and F(ab')$_2$, as well as bifunctional hybrid antibodies (e.g., Lanzavecchia et al. (1987)) and in single chains (e.g., Huston et al. (1988) and Bird et al. (1988), which are incorporated herein by reference). (See, generally, Hood et al., "Immunology", Benjamin. N.Y., $2^{nd}$ ed. (1984), and Hunkapiller and Hood (1986), which are incorporated herein by reference). Thus, the term "antibody" includes antigen binding antibody fragments, as are known in the art, including Fab, Fab$_2$, single chain antibodies (scFv for example), chimeric antibodies, etc., either produced by the modification of whole antibodies or those synthesized de novo using recombinant DNA technologies.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., U.S. Department of Health and Human Services, (1983); which is incorporated herein by reference). The sequences of the framework regions of different light or heavy chains are relatively conserved within a species. As used herein, a "human framework region" is a framework region that is substantially identical (about 85% or more, usually 90 to 95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. One example of a chimeric antibody is one composed of the variable or antigen-binding domain from a mouse antibody and the constant or effector domain from a human antibody, although other mammalian species may be used.

As used herein, the term "humanized" immunoglobulin refers to an immunoglobulin having a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they are generally substantially identical to human immunoglobulin constant regions, i.e., at least about 85-90%, or about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. One says that the donor antibody has been "humanized", by the process of "humanization", because the resultant humanized antibody is expected to bind to the same antigen as the donor antibody that provides the CDR's.

Thus, humanized forms of non-human (e.g., murine) antibodies are chimeric immunoglobulins, immunoglobulin chains or fragments thereof (such as Fv, Fab, Fab', F(ab")2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody has substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will include at least a portion of an immunoglobulin constant region (Fc), typically that of a human immunoglobulin (Jones et al. (1986); Riechmann et al. (1988); and Presta (1992)).

It is understood that the humanized antibodies may have additional conservative amino acid substitutions which have substantially no effect on antigen binding or other immunoglobulin functions. By conservative substitutions are intended combinations such as gly, ala; val, ile, leu; asp, glu; asn, gln; ser, thr; lys, arg; and phe, tyr.

Humanized immunoglobulins, including humanized antibodies, have been constructed by means of genetic engineering. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522 (1986); Riechmann et al., Nature. 332:323 (1988); Verhoeyen et al., Science, 239:1534 (1988)), by substituting rodent CDRs or CDR sequences for the corresponding sequences of a human antibody. Accordingly, such "humanized" antibodies are chimeric antibodies that have substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies.

Human antibodies can also be produced using various techniques known in the art, including phage display libraries (Hoogenboom and Winter, *J. Mol. Biol.,* 227:381 (1991); Marks et al., *J. Mol. Biol.,* 222:581 (1991)). The techniques of Cole et al. and Boerner et al. are also available for the preparation of human monoclonal antibodies (Cole et al., *Monoclonal Antibodies and Cancer Therapy*. Alan R. Liss, p. 77 (1985) and Boerner et al., *J. Immunol.,* 147:86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature,* 368:856 (1994): Morrison, *Nature* 368:812 (1994); Fishwild et al., *Nature Biotechnology.* 14:845 (1996); Neuberger, *Nature Biotechnology,* 14:826 (1996); Lonberg and Huszar, *Intern. Rev. Immunol.,* 13:65 (1995). Most humanized immunoglobulins that have been previously described have a framework that is identical to the framework of a particular human immunoglobulin chain and three CDR's from a non-human donor immunoglobulin chain.

A framework may be one from a particular human immunoglobulin that is unusually homologous to the donor immunoglobulin to be humanized, or a consensus framework derived from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60-70%. By choosing one of the human heavy (respectively light) chain variable regions that is most homologous to the heavy (respectively light) chain variable region of the other immunoglobulin, fewer amino acids will be changed in going from the one immunoglobulin to the humanized immunoglobulin, the precise overall shape of a humanized antibody having the humanized immunoglobulin chain may more closely resemble the shape of the donor antibody, also reducing the chance of distorting the CDR's.

Typically, one of the 3-5 most homologous heavy chain variable region sequences in a representative collection of at least about 10 to 20 distinct human heavy chains is chosen as acceptor to provide the heavy chain framework, and similarly for the light chain. One of the 1 to 3 most homologous variable regions may be used. The selected acceptor immunoglobulin chain may have at least about 65% homology in the framework region to the donor immunoglobulin.

In many cases, it may be considered desirable to use light and heavy chains from the same human antibody as acceptor sequences, to be sure the humanized light and heavy chains will make favorable contacts with each other. Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor.

Humanized antibodies generally have advantages over mouse or in some cases chimeric antibodies for use in human therapy: because the effector portion is human, it may interact better with the other parts of the human immune system (e.g., destroy the target cells more efficiently by complement-dependent cytotoxicity (CDC) or antibody-dependent cellular cytotoxicity (ADCC)); the human immune system should not recognize the framework or constant region of the humanized antibody as foreign, and therefore the antibody response against such an antibody should be less than against a totally foreign mouse antibody or a partially foreign chimeric antibody.

DNA segments having immunoglobulin sequences typically further include an expression control DNA sequence operably linked to the humanized immunoglobulin coding sequences, including naturally-associated or heterologous promoter regions. Generally, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, Cells of Immunoglobulin Synthesis, Academic Press, New York, (1979), which is incorporated herein by reference).

Other "substantially homologous" modified immunoglobulins to the native sequences can be readily designed and manufactured utilizing various recombinant DNA techniques well known to those skilled in the art. For example, the framework regions can vary at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, *Gene,* 8:81 (1979) and Roberts et al., *Nature,* 328:731 (1987), both of which are incorporated herein by reference). Substantially homologous immunoglobulin sequences are those which exhibit at least about 85% homology, usually at least about 90%, or at least about 95% homology with a reference immunoglobulin protein.

Alternatively, polypeptide fragments comprising only a portion of the primary antibody structure may be produced, which fragments possess one or more immunoglobulin activities (e.g., antigen binding). These polypeptide fragments may be produced by proteolytic cleavage of intact antibodies by methods well known in the art, or by inserting stop codons at the desired locations in vectors known to those skilled in the art, using site-directed mutagenesis.

As used herein, the term "binds specifically" or "specifically binds," in reference to an antibody/antigen interaction, means that the antibody binds with a particular antigen without substantially binding to other distinct antigens or to unrelated antigens.

The term "peptide" when used with reference to a linker, describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to another molecule through the carboxy terminus, the amino terminus, or through any other convenient point of attachment, such as, for example, through the sulfur of a cysteine. In one embodiment, a peptide linker may comprise 3 to 25, 5 to 21, or 5 to 15, or any integer in between, amino acids.

Exemplary System for Targeted Gene Delivery

Viral vectors are a major means of gene delivery with the potential to impact a number of pediatric diseases including inherited genetic disorders and cancer. Naturally evolved properties of many viral vectors are, however, mismatched to clinical delivery needs. In gene therapy, for example, cell type specificity is paramount, as ectopic expression in off-target tissues or cells is undesirable and poses a safety risk. We propose to remove these legacy constraints of natural evolution by functionally separating viral entry (host recognition) and viral replication (gene delivery).

This is achieved by removing endogenous tropism of the virus, and by introducing into the virus capsid small protein endonuclease domains that covalently bind single strand DNA (ssDNA) in a sequence specific and nonoverlapping (orthogonal) fashion. By linking different targeting molecules, e.g., monoclonal antibodies (mAB), with ssDNA substrates, virus becomes decorated with targeting molecules, e.g., antibody to form covalent mAB/AAV composites (FIG. 1A).

To achieve programmable cell type-specific viral gene delivery, at least two components are combined. In one embodiment, as in ADC and CAR-T, antibodies are used to recognize surface markers of a targeted cell type. In one embodiment, as in viral approaches to gene therapy. AAV is employed as a viral vector that is amenable to facile capsid engineering. In one embodiment, antibodies and AAV are combined via a covalently link using, for example, HUH endonuclease domains. HUH domains are small (10-20 kDa) and robustly form covalent bonds with short single strand (ss) DNA in a sequence specific fashion. HUH domains are orthogonal and multiplexable; there is no overlap between sequences that each HUH domain recognizes and binds to. By displaying different HUH domains on different viruses, e.g., different AAVs, delivering different payloads, different ssDNA-conjugated targeting molecules such as antibodies recognizing different cell surface markers are covalently attached to specific viral particles in a programmable fashion.

The present disclosure achieves a separation of function and roles: cell targeting is mediated by targeting molecules, e.g., antibodies, and gene delivery mediated by the virus. By separating these roles into two independently engineerable components, and then combining them as needed, complex interdependency issues are avoided that have hampered previous efforts in viral vector engineering. A functional separation of components also allows rapid target switching without labor intensive repackaging of virus. Thus, a set of template viruses (packaging a battery of therapeutic/cytotoxic payloads) can be prepared at large scale, biobanked, and 'armed' with a target-directed antibody ad hoc.

In one embodiment, a chimeric AAV that incorporates a ssDNA-binding HUH domain was prepared. The HUH tag is functionally displayed in this context and incorporated into infectious, genome-containing capsids. Without attachment of a nanobody conjugated to the cognate ssDNA of the HUH, the chimeric virus is not infectious. With attachment of an anti-GFP nanobody via the HUH tag, e.g., formation of the mAB/AAV composite, the virus becomes 'armed' and is able to infect cells expressing a surface-displayed GFP.

A chimeric AAV that incorporates a ssDNA-binding HUH domain was prepared. The HUH tag is functionally displayed in this context and incorporated into infectious, genome-containing capsids. Without attachment of a nanobody conjugated to the cognate ssDNA of the HUH, the chimeric virus is not infectious. With attachment of an anti-GFP nanobody via the HUH tag, i.e., formation of the mAB/AAV composite, the virus becomes 'armed' and is able to infect cells expressing a surface-displayed GFP.

The approach enables simultaneous gene delivery to different cell types with minimal crosstalk or off-target effects. This allows for new kinds of gene therapy approaches that could significantly impact the care of children with genetic disorders or cancer.

Exemplary Compositions and Methods

In one embodiment, a method to assemble a highly efficacious oncolytic AAV, and compositions useful in the methods, are provided. Gene therapy to treat brain cancer, while promising in preclinical testing, has so far not been effective in clinical trials and may be due to a mismatch between the naturally evolved properties of viral vectors used in these trials and the clinical delivery requirements to infect cancer cells specifically. In one embodiment, AAV8 is engineered by replacing amino acids 588-591 (counting from start codon of VP1) in capsid proteins VP1, VP2, and W3 with a SpyTag, flanked by GGGGSGGGGS (SEQ. ID NO:61) on both N- and C-terminus thus removing AAV8's endogenous tropism by knocking out the heparin binding domain (HBD). Using a helper-free systems, a payload encoding a 'cellular suicide' gene (cytosine deaminase driven from glial or ubiquitous promoter) is packaged. In a separate reaction, an anti-epidermal growth factor receptor variant III antibody is linked to a ssDNA oligo specific to the HUH domain RepB using hydrazone chemistry. This ssDNA-conjugated antibody is then covalently linked to recombinantly produced RepB, which is in turn genetically fused to the SpyCatcher domain. The latter domain enables covalent linkage of the anti body-ssDNA-RepB product to fully assembled particles via the SpyTag. Using size-selective ultracentrifugation, fully assembled mAB/AAV composites are separated from unreacted components. The resultant oncolytic AAV product is formulated as a foam or an emulsion, and is applied by the surgeon after resection of the main tumor mass. Its role is to seek out the remaining (escaped) glioma cells by virtue of cancer-cell tropism and small (highly diffusive) size of viral capsid, and to kill these cells by delivering a suicide gene. A corollary, the unique access provided by the surgery circumvent many of the issue encountered with systemically delivered AAV gene therapy. These included broad neutralizing serum responses and limited ability to cross the blood-brain barrier.

In one embodiment, a method for multiplexed gene delivery to mononuclear cells from whole blood in vitro and in vivo is provided. Peripheral blood mononuclear cells (PBMCs) include multiple different hematopoietic cell types including T-cells, B-cells, monocytes, and NK cells. Reprogramming, including expression of heterologous proteins and gene editing of hematopoietic cells is highly relevant to both gene therapy and cancer immunotherapy. AAV Serotype 2 (AAV2) is engineered by first separating the expression of capsid proteins VP1 from VP2 and VP3. This is achieved by introducing alternative splice acceptors into one copy the cap gene, which suppresses production of VP2 and VP3. VP2 and VP3 are in turn produced in trans from a cap gene copy in which the start codon of VP1 is mutated to lysine (M1K). In VP2 and VP3 amino acids 585-588 (counting from start codon of VP1) are replaced with a HA-tag. In VP amino acids 585-588 (counting from start codon of VP) are replaced with a HIS-tag, which enables affinity purification of recombinantly produced viral particles that contain VP1. From this plasmid, three different VP1-HUH fusions are constructed by introducing HUH domains mMobA, RepB, or PCV2 into VP1 between amino acids 454-455 (counting from start codon of VP1) flanked by GGGS on both N- and C-terminus of each HUH domain. Each HUH-AAV variant is recombinantly produced in a helper-free systems to package different transgenes: mMobA-displaying AAV will package anti-CD19 scfv/CD28/CD3ζ CAR, PCV2-displaying AAV will package anti-BCMA scfv/4-1BB/CD3ζ CAR, and RepB-displaying AAV will package IL-21. After helper-free production, tropism-null AAVs are armed by incubation with antibodies conjugated to ssDNA specific to one of the three utilized HUH-tags. Specifically, mMobA-displaying AAV is covalently linked to anti-CD8 mAB to target CD8+ T lymphocytes and result in the expression of the anti-CD19 CAR in these cells. PCV2-displaying AAV is linked to anti-CD4 mAB to target CD4+ lymphocytes and result in the expression of anti-BCMA CAR in these cells. Together, thus transformed CD8+ and CD4+ cells are targeting two important antigen targets in multiple myeloma (MM). Last, RepB-linked AAV is linked to anti-OX40 mAB (CD134), which results in the targeting of activated regulatory T-cells (Treg). Delivery of IL-21 to Treg will downregulate their activity in an autocrine fashion, thus limiting their contribution to the highly immunosupressive tumor environment, and enhancing efficacy of cancer-targeted CD8+ and CD4+ cells. Note that due to the orthogonal nature of HUH ssDNA specificity, arming of tropism-null virus can be done in a single reaction which provides maximum flexibility and ease of use. This mixture of AAVs is then used according to clinical protocol specification, for example administered intravenous to the patient, of added the in vitro preparation of patient whole blood.

In one embodiment, methods for veterinary DNA vaccines are provided. DNA-based vaccination is a promising technology for protecting lifestock from a range of veterinary diseases and has important advantages to traditional vaccines that use attenuated or inactivated pathogens. This includes the specificity of the antigen produced and the ability to guide the type of elicited immune response. The critical factors for current DNA vaccines are (1) the efficacy by which professional antigen-presenting cells (APC) are transfected, and (2) the amount of synthesized pathogen-antigen that then elicits and adaptive immune response. Both can be improved with viral vectors that target APCs directly. AAV Serotype DJ (AAV-DJ) is engineered by first separating the expression of capsid proteins VP2 from VP1 & VP3. This is achieved by subcloning the ORF of VP2, and mutating the alternative start codon for VP2 (T138A) in the second cap gene copy. All cap gene copies will have amino acids 587-590 (counting from start codon of VP1) replaced with a HIS-tag, which removes endogenous tropism and enables affinity purification of recombinantly produced viral particles. Furthermore, two concatenated HUH domains—Trail & mMobA separated by a flexible (Gly)$_6$ linker and flanked by (GGGG)$_2$ (SEQ ID NO:62) linkers at the C-terminus—are genetically fused to the N-terminus of VP2. Recombinant AAV is recombinantly produced in a helper-free systems to package transgenes encoding for pathogens antigens g. MOMP from *C. psittaci* to protect poultry from Chlamydiosis, E2 from Picornavirus to protect cattle from Foot and Mouth disease, or E2 from Pestivirus to protect swine from Swine Fever). A second part of the packaged viral genome encodes for cytokine that can direct the type of the elicited adaptive immune response: Th1-type (IL-2, IL-15, and IL-18) and Th2-type (IL-4 and IL-10). After production, tropism-null AAV are armed by incubation with conjugated antibodies targeting APC (e.g. CD205 for dendritic cells, CDG4 for macrophages). Using concatenated HUH domains displayed on the surface of tropism-null AAV ensure stochiometric linkage of APC-directed antibodies. As an alternative to using two antibodies, one HUH domain could be used to link a ssDNA-conjugated adjuvants, e.g. Monophosphoryl lipid A, which will enhance APC uptake and processing. The resulting product is an APC-directed recombinant AAV encoding for a pathogen-derived antigen that is delivered into animal by intramuscular injection.

Exemplary Capsid Regions for Modification

In one embodiment, the VP is an AAV-1, AAV-2, AAV-3, AAV-4, AAV-5, AAV-6, AAV-7, AAV-8, AAVrh10, or AAV-9 VP. In one embodiment, regions for modification, e.g., mutation, deletion and/or insertion, in an AAV capsid include positions 455, 456, 457, 585, 586, 587, 588, 589, 590, or 591. In one embodiment, regions for modification, e.g. mutation, deletion and/or insertion, in an AAV capsid are flanked by the motif NPLXDQYL(Y/W)X(Y/W)XXT (SEQ ID NO:63)—site—XXXXX(K/R)N(W/Y)X(P/T)G (SEQ ID NO:64).

In one embodiment, the fiber is an Ad5 fiber. In one embodiment, regions for modification. e.g. mutation, deletion and/or insertion, in an Ad fiber are positions 408, 409, 450, 451, 468, 469, 542, 543, 560, 561, 564, 565.

In one embodiment, the capsid protein is Sindbis Virus structural polyprotein that is processed to envelope glycoproteins E1, E2, and E3. In one embodiment, regions for modification. e.g., mutation, deletion and/or insertion, in individual envelope glycoproteins are E2: 1, 68, 69, 70, 71, 114, 159, 160; E3: 60, 61, 62, 63, 64

In one embodiment, the capsid protein is a Vesicular Stomatitits Virus envelope glycoprotein (VSV-G). In one embodiment, regions for modification, e.g., mutation, deletion and/or insertion, in the VSV-G include positions 16, 17, 18, 162, 163, 230, 231, 368, 367, 380, 381.

Exemplary Pairs of HUH Domains and ssDNA Substrates Thereof

Exemplary HUH domains may be obtained from PCV2 (SEQ ID NO:2), phiX174 (SEQ ID NO:3), mMobA (SEQ ID NO:4), TraI36 (SE ID NO:5), RepB (SEQ ID NO:6), FBNYV (SEQ ID NO:7), NES (SEQ ID NO:8), TrwC (SEQ ID NO:9), TYLCV (SEQ ID NO:10), RepBm (SEQ ID NO:20), or DCV (SEQ ID NO:21). Moreover, fragments of those sequences may be employed in viral capsids so long as the ssDNA binding and binding specificity is not substantially altered.

SEQ ID NO: 2 is SPSKKNGRSG PQPHKRWVFT LNNPSEDERK

KIRDLPISLF DYFIVGEEGN EEGRTPHLQG FANFVKKQTF

NKVKWYLGAR CHIEKAKGTD QQNKEYCSKE GNLLMEEGAP

RSQGQR.

SEQ ID NO: 3 is KSRRGFAIQR LMNAMRQAHA DGWFIVFDTL

TLADDRLEAF YDNPNALRDY FRDIGRMVLA AEGRKANDSH

ADCYQYFCVP EYGTANGRLH FHAVHFMRTL PTGSVDPNFG

RRVRNRRQLN SLQNTWPYGH SMPIAVRYTQ DAFSRSGWLW

PVDAKGEPLK ATSYMAVGFY VAKYVNKKSD MDLAAKGLGA

KEWNNSLKTK LSLLPKKLFR IRMSRNFGMK MLTMTNLSTE

CLIQLTKLGY DATPFNQILK QNAKREMRLR LGKVTVADVL

AAQPVTTNLL KFMRASIKMI GVSNLQSFIA SMTQKLTLSD

ISDESKNYLD KAGITTACLR IKSKWTAGGK

SEQ ID NO: 4 is MAIYHLTAKT GSRSGGQSAR AKADYIQREG

KYARDMDEVL HAESGHMPEF VERPADYWDA ADLYERANGR

LFKEVEFALP VELTLDQQKA LASEFAQHLT GAERLPYTLA

IHAGGGENPH CHLMISERIN DGIERPAAQW FKRYNGKTPE

KGGAQKTEAL KPKAWLEQTR EAWADHANRA LERAGH.

SEQ ID NO: 5 is MMSIAQVRSA GSAGNYYTDK DNYYVLGSMG

ERWAGRGAEQ LGLQGSVDKD VFTRLLEGRL PDGADLSRMQ

DGSNRHRPGY DLTFSAPKSV SMMAMLGGDK RLIDAHNQAV

DFAVRQVEAL ASTRVMTDGQ SETVLTGNLN MALFNHDTSR

DQEPQLHTHA VVANVTQHNG EWKTLSSDKV GKTGFIENVY

ANQINFGRLY REKLKEQVEA LGYETEVVGK HGMWEMPGVP

VEAFSGRSQT IREAVGEDAS LKSRDVAALD TRKSKQHVDP

EIKMAEWMQT LKETGFDIRA YRDAADQRAD LRTLTPGPAS

QDGPDVQQAV TQAIAGLSER.

SEQ ID NO: 6 is MAKEKARYFT FLLYPESIPS DWELKLETLG

VPMAISPLHD KDKSSIKGQK YKKAHYHVLY IAKNPVTADS

VRKKIKLLLG EKSLAMVQVV LNVENMYLYL THESKDAIAK

KKHVYDKADI KLINNFDIDR YLEFBNYV.

SEQ ID NO: 7 is MARQVICWCF TLNNPLSPLS LHDSMKYLVY

QTEQGEAGNI HFQGYIEMKK RTSLAGMKKL IPGAHFEKRR

GTQGEARAYS MKEDTRLEGP WEYGEFVP NES.

SEQ ID NO: 8 is AMYHFQNKFV SKANGQSATA KSAYNSASRI

KDFKENEFKD YSNKQCDYSE ILLPNNADDK FKDREYLWNK

VHDVENRKNS QVAREIIIRGL PNEFDPNSNI ELAKEFAESL

SNEGMIVDLN IHKINEENPH AHLLCTLRGL DKNNEFEPKR

KGNDYIRDWN TKEKHNEWRK RWENVQNKHL EKNGFSVRVS

ADSYKNQNID LEPTKKEGWK ARKFEDETG.

SEQ ID NO: 9 is MLSHMVLTRQ DIGRAASYYE DGADDYYAKD

GDASEWQGKG AEELGLSGEV DSKRFRELLA GNIGEGHRIM

RSATRQDSKE RIGLDLTFSA PKSVSLQALV AGDAEIIKAH

DRAVARTLEQ AEARAQARQK IQGKTRIETT GNLVIGKFRH

ETSRERDPQL HTHAVILNMT KRSDGQWRAL KNDEIVKATR

YLGAVYNAEL AHELQKLGYQ LRYGKDGNFD LAHIDRQQIE

GFSKRTEQIA EWYAARGLDP NSVSLEQKQA AKVLSRAKKT

SVDREALRAE WQATAKELGI DFSTLYCV.

SEQ ID NO: 10 is MPRLFKIYAK NYFLTYPNCS LSKEEALSQL

KKLETPTNKK YIKVCKELHE NGEPHLHVLI QFEGKYQCKN

QRFFDLVSPN RSAHFHPNIQ AAKSSTDVKT YVEKDGNFID

FGVSQIDGRS.

SEQ ID NO: 20 is MSEKKEIVKG RDWTFLVYPE SAPENWRTIL

DETFMRWVES PLHDKDVNAD GEIKKPHWHI LLSSDGPITQ

TAVQKIIGPL NCPNAQKVGS AKGLYRYMVH LDNPEKYQYS

LDEIVGHNGA DVASYFELTA.

SEQ ID NO: 21 is MAKSGNYSYK RWVFTINNPT FEDYVHVLEF

CTLDNCKFAI VGEEKGANGT PHLQGFLNLR SNARAAALEE

SLGGRAWLSR ARGSDEDNEE YCAKESTYLR VGEPVSKGRS S.

In one embodiment, the HUH domain has at least 80%, 85%, 90%, 92%, 95%, 97%, 98%, or 99% amino acid sequence identity to one of SEQ ID Nos. 2-10 and 20-21.

In one embodiment, the HUH domain is a fragment of one of SEQ ID Nos. 2-10 or 20-21, e.g., one having a deletion of 1, 2, 3, 4, 5, or more, e.g., 10, 15, 20, 25, 30, 35, 40, 45 or 50 residues, that has at least 80%, 85%, 90%, 95%, 98%, 99% or 100% the activity of SEQ ID Nos. 2-10 or 20-21.

In one embodiment, the HUH substrate has at least 80%, 85%, 90%, 92%, 95%, 97%, 98%, or 99% nucleic acid sequence identity to one of SEQ ID Nos. 1-4 or 11.

In one embodiment, the HUH substrate is a fragment of one of SEQ ID Nos. 1-4 or 11, e.g., one having a deletion of 1, 2, 3, 4, 5, or more, e.g., 10, 15, 20, 25, 30, 35, 40, 45 or 50 residues, that has at least 80%, 85%, 90%, 95%, 98%, 99% or 100% the activity of SEQ ID Nos. 1-4 or 11.

Exemplary Linkers

Exemplary linkers include but are not limited to (GGGGS)$_3$, (GGGGS)$_3$, (GGGGS)$_3$, (Gly)$_8$, (Gly)$_6$, (EAAAK)$_3$, (EAAAK)$_n$ (n=1-3), A(EAAAK)$_4$ALEA (EAAAK)$_4$A, A(EAAAK)$_4$ALEA(EAAAK)$_4$A, (GGGGS)$_3$, A(EAAAK)$_4$ALEA(EAAAK)$_4$A, A(EAAAK)$_4$ALEA(EAAAK)$_4$A, GGGGS, PAPAP, AEAAAKEAAAKA, (GGGGS)$_n$ (n=1, 2, 4), (Ala-Pro)$_n$ (10-34 aa), VSQTSKLTR↓AETVFPDV, PLG↓LWA, RVLI-AEA; EDVVCC↓SMSY; GGIEGR↓GS$^c$, TRHRQPR↓GWE; AGNRVRR↓SVG; RRRRRRR↓R↓R, GFLG↓, A(EAAAK)$_4$ALEA(EAAAK)$_4$A, (GlyGlyGlyGly-Ser)$_2$-GGGGSGGGGS, LE, or GGSSGGGSGG (SEQ ID Nos. 22-52).

Exemplary Targeting Molecules

In one embodiment, the target molecule binding protein is an antibody or a portion thereof, e.g., a scFV or a single domain antibody (sdAb) that is based on the recombinant variable heavy domains from the heavy chain only antibodies found in Camelids and sharks. Other binding proteins include intrabodies and nanobodies.

The targeting molecules may be specific for any selected antigen, e.g., any cell surface marker including any post-translational modification (CD52, HER2, CD19, CD20, CD30, CD3, OX40, VEGFR, EGFR, CD205, CD64, CD4, CD8), any membrane protein including any post-translational modification (Nav1.8, Clc3, NMDA receptors, D1 & D2 muscarinic receptors, ASIC1/3), any synthetic or otherwise engineered proteins targeted to the cell surface (GFP-GPI, GFP-PDGR, mGRASP), and any glycosylated lipids (cerebroside, galactoside, lipopolysaccharide).

Exemplary Genes for Delivery

In one embodiment, the gene product is a therapeutic gene product, e.g., GM-CSF, CD40L, IL-2, CD80, MDA-7, or TNF-alpha. In one embodiment, the gene product is a prophylactic gene product, e.g. kallikrein or is pathogen-derived protein fragments (Pestivirus E2, C. psittaci MOMP, S. aureus FnBP, Saureus ClfA, Avian paramyxovirus HN, B. melitensis OMP-31, S. japonicum Sj23). In one embodiment, the gene product is a catalytic RNA. In one embodiment the gene product is a guide RNA. In one embodiment the gene is a donor for homologous recombination. In one embodiment the gene product is a nuclease suitable for genome editing, e.g. TALENS, S. pyogenes Cas9, S. aureus Cas9. In one embodiment, the gene product is a cytotoxic gene product, e.g., suicide genes such as rexin-G or HSVtk in combination with ganciclovir, an apoptosis inducer, e.g., p53, p27Kip1, p21Waf1, p16INK4A, Ad5IkB, or cyclin-dependent kinase inhibitors, or an angiogenesis inhibitor. In one embodiment, the gene product is a chimeric T-cell receptor (anti-CD19 scfv/CD28/CD3ζ CAR, anti-BCMA scfv/4-1BB/CD3ζ CAR).

In one embodiment, the gene to be delivered includes but is not limited to cystic fibrosis transmembrane conductance regulator, α-antitrypsin, β-globin, γ-globin, tyrosine hydroxylase, glucocerebrosidase, aryl sulfatase A, factor VIII, dystrophin or erythropoietin, a viral, bacterial, tumor or fungal antigen, or an immune response modulator, e.g., a cytokine including but not limited to IFN-alpha, IFN-gamma, TNF, IL-1, IL-17, or IL-6.

Exemplary rAAV Genomes

An AAV vector typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, e.g., (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters may be preferred because constitutive expression of the rep gene can have a negative impact on the host cell. A large variety of inducible promoters are known in the art; including, by way of illustration, heavy metal ion inducible promoters (such as metallothionin promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), e.g., linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Removal of one or more AAV genes is in any case desirable, to reduce the likelihood of generating replication-competent AAV ("RCA"). Accordingly, encoding or promoter sequences for rep, cap, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by AAV ITRs and in one embodiment do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

Uses

The virus can be used for administration to an individual for purposes of gene therapy or vaccination. Suitable diseases for therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Vectors may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic or prophylactic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene.

Vaccination can be conducted to protect cells from infection by infectious pathogens. As the traditional vaccine methods, vectors of this invention may be used to deliver transgenes encoding viral, bacterial, tumor or fungal antigen and their subsequent expression in host cells. The antigens, which expose to the immune system to evoke an immune response, can be in the form of virus-like particle vaccines or subunit vaccines of virus-coding proteins. Alternatively, as the method of passive immunization, vectors of this invention might be used to deliver genes encoding neutralizing antibodies and their subsequent expression in host non-hematopoietic tissues. The vaccine-like protection against pathogen infection can be conducted through direct provision of neutralizing antibody from vector-mediated transgene expression, bypassing the reliance on the natural immune system for mounting desired humoral immune responses.

The introduction of the virus to an animal may involve use of any number of delivery techniques (both surgical and non-surgical) which are available and well known in the art. Such delivery techniques, for example, include vascular catheterization, cannulization, injection, inhalation, endotracheal, subcutaneous, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for administration. There are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the virus as a free acid (DNA contains acidic phosphate groups) or a pharmacologically acceptable salt can be prepared in water suitably mixed with a surfactant such as hydroxypropylcellulose. A dispersion of viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the virus in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the methods of preparation include but are not limited to vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Compositions may be used in vivo as well as ex vivo. In vivo gene therapy comprises administering the vectors directly to a subject. Pharmaceutical compositions can be supplied as liquid solutions or suspensions, as emulsions, or as solid forms suitable for dissolution or suspension in liquid prior to use. For administration into the respiratory tract, one mode of administration is by aerosol, using a composition that provides either a solid or liquid aerosol when used with an appropriate aerosolubilizer device. Another mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, at least about 80%, at least about 95%, or at least about 99% of the cells of the desired tissue type. As a guide, the number of vector particles present in a single dose given by bronchoscopy will generally be at least about $1\times10^{12}$, e.g., about $1\times10^{13}$, $1\times10^{14}$, $1\times10^{5}$ or $1\times10^{16}$ particles, including both DNAse-resistant and DNAse-susceptible particles. In terms of DNAse-resistant particles, the dose will generally be between $1\times10^{12}$ and $1\times10^{16}$ particles, more generally between about $1\times10^{12}$ and $1\times10^{15}$ particles. The treatment can be repeated as often as every two or three weeks, as required, although treatment once in 180 days may be sufficient.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

It is understood that variations may be applied to these methods by those of skill in this art without departing from the spirit of this invention.

Dosages, Formulations and Routes of Administration

Administration of the recombinant viruses may be continuous or intermittent, depending, for example, upon the recipient's physiological condition, whether the purpose of the administration is therapeutic or prophylactic, and other factors known to skilled practitioners, the administration of the recombinant viruses may be essentially continuous over a preselected period of time or may be in a series of spaced doses. Both local and systemic administration is contemplated. When the recombinant viruses are employed for prophylactic purposes, recombinant viruses are amenable to chronic use, e.g., by systemic administration.

One or more suitable unit dosage forms comprising the recombinant viruses, can be administered by a variety of routes including oral, or parenteral, including by rectal, transdermal, subcutaneous, intravenous, intramuscular, intraperitoneal, intrathoracic, intrapulmonary and intranasal routes. For example, for administration to the liver, intravenous administration may be preferred. For administration to the lung, airway administration may be preferred. The formulations may, where appropriate, be conveniently presented in discrete unit dosage forms and may be prepared by any of the methods well known to pharmacy. Such methods may include the step of bringing into association the recombinant viruses with liquid carriers, solid matrices, semi-solid carriers, finely divided solid carriers or combinations thereof, and then, if necessary, introducing or shaping the product into the desired delivery system.

When the recombinant viruses are prepared for oral administration, they may be combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the recombinant viruses can be prepared by procedures known in the art using well known and readily available ingredients. For example, the recombinant viruses can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The recombinant viruses can also be formulated as elixirs or solutions for convenient oral administration or as solutions appropriate for parenteral administration, for instance by intramuscular, subcutaneous or intravenous routes.

The pharmaceutical formulations of the recombinant viruses can also take the form of an aqueous or anhydrous solution or dispersion, or alternatively the form of an emulsion or suspension.

Thus, the recombinant viruses may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, e.g., ethyl or isopropyl lactate, fatty acid triglycerides such as the products marketed under the name "Miglyol", isopropyl myristate, animal, mineral and vegetable oils and polysiloxanes.

For administration to the upper (nasal) or lower respiratory tract by inhalation, the recombinant viruses are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the recombinant viruses may be administered via nose drops, a liquid spray, such as via a plastic bottle atomizer or metered-dose inhaler. Typical of atomizers are the Mistometer (Wintrop) and the Medihaler (Riker).

The local delivery of the recombinant viruses can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The formulations and compositions described herein may also contain other ingredients such as antimicrobial agents, or preservatives. Furthermore, the active ingredients may also be used in combination with other agents, for example, bronchodilators.

The recombinant viruses may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice.

The dosage of the recombinant viruses will vary with the form of administration, the particular compound chosen and the physiological characteristics of the particular patient under treatment. Generally, small dosages will be used initially and, if necessary, will be increased by small increments until the optimum effect under the circumstances is reached.

The invention will be further described by the following non-limiting examples.

Example 1

The ability to covalently attach DNA to proteins has broad applications in, for example, DNA nanotechnology, cellular imaging, and/or targeted nucleotide delivery. DNA is highly programmable, easy and cost-effective to manipulate, and can be engineered to include various useful modifications such as, for example, a fluorophore, a reactive chemical moiety, and/or a photocrosslinker. Current strategies for conjugating DNA to a protein involve using a thiol and/or an amine moiety encoded in oligonucleotides to couple to proteins, but these strategies can lack specificity. Another conventional method involves enzymatic ligation of a protein fusion tag such as a SNAP tag (New England Biolabs, Inc., Ipswich. Mass.) or a HALOTAG (Promega, Madison, Wis.) tags) to a modified DNA base. However, these require modified oligonucleotides to attach the target bases, along with purification and verification of the strands, and even then are still limited to two or three orthogonal attachment sites.

Proteins that recognize a specific sequence of DNA and form stable covalent bonds between the protein and the DNA can be employed to covalently link other components. These proteins include HUH endonuclease domains. HUH endonuclease domains are present in hundreds of viral replication proteins, at least 20 relaxases, and many transposases. The HUH proteins are so named because of a catalytic motif that most commonly involves two histidines and a third amino acid that is usually a hydrophobic amino acid. The amino acids in the catalytic motif coordinate a metal. HUH proteins represent a group of proteins that include, for example, virus proteins and bacterial relaxases. In many cases, an HUH protein contains an N-terminal "Rep" or "relaxase" domain that contains the HUH catalytic motif, including a catalytic tyrosine as the polar amino acid residue. A HUH protein often includes at least one domain in addition to the Rep/relaxase domain such as, for example, a helicase domain. The HUH-based capsid fusion polypeptides described herein include at least a functional portion of the HUH domain, i.e., the metal coordinating amino acid residues (typically histidine residues) and the catalytic tyrosine residue.

The HUH endonuclease-based capsid fusion-tag strategy can covalently link DNA to a protein of interest by exploiting the native covalent DNA linking character of the HUH endonucleases. The HUH endonucleases possess a small "nicking domain" that in isolation can bind a specific single-stranded DNA sequence, nick the DNA sequence using a transesterification mechanism similar to that of topoisomerases, and subsequently form a covalent phosphotyrosine link between the protein and the 5' end of the DNA strand. This nicking domain is often found in series with other protein domains, e.g., a helicase domain, a primase domain, and/or a multimerization domain. The nicking activity of several HUH endonucleases has been characterized biochemically and structurally. The catalysis often involves coordinating a magnesium ion, a nickel ion, or a manganese ion in the active site by two conserved histidines and a polar residue 'U' that form the so-called "HUH motif" although the HUH motif may possess only one histidine residue.

The nicking domains of HUH endonucleases can range in size from 90-300 amino acids. Moreover, there are many examples of HUH endonucleases in nature, each with its own specific target sequence. Therefore, a library of HUH fusion-tagged proteins, each protein of interest with a unique HUH tag, can allow one to specifically label many proteins in the same reaction mixture at the same time. A panel of exemplary HUH-endonucleases is provided in Table 1.

TABLE 1

Properties of exemplary HUH-tags.

| HUH-tag | Full name | Pdb ID | MW (kDa) | pI | Ori sequence[&] |
|---|---|---|---|---|---|
| PCV2* (SEQ ID NO: 2) | Porcine circovirus 2 | 2HW0 | 13.4 | 9.5 | aagtatt/accagana (SEQ ID NO: 1) |
| DCV (SEQ NO: 21) | ID circovirus | Duck | 13.4 | 5.4 | |
| FBNYV {circumflex over ( )} (SEQ ID NO: 7) | Faba bean necrosis yellow virus | 2HWT | 11.3 | 8.6 | |
| RepB[#] (SEQ ID NO: 6) | Replication protein RepB *Streptococcus agalactiae* | 3DKY | 15.2 | 9.4 | tgettccgtactacg/accccca (SEQ ID NO: 2) |

TABLE 1-continued

Properties of exemplary HUH-tags.

| HUH-tag | Full name | Pdb ID | MW (kDa) | pI | Ori sequence[&] |
|---|---|---|---|---|---|
| RepBm (SEQ ID NO: 20) | RepB *Fructobacilus tropaeoli* | | 14.7 | 5.5 | |
| TraI[+] (SEQ ID NO: ) | Conjugation protein TraI *E. coli* | 1P4D | 36.4 | 5.6 | tttgcgtggggtgt/ ggtgctt (SEQ ID NO: 3) |
| mMobA[°] (SEQ ID NO: 4) | Mobilization protein A *E. coli* | 2NS6 | 20.9 | 6.3 | ccagtttctcgaagaga aaccggtaagtgca/ ccctccc (SEQ ID NO: 4) |
| NES[@] (SEQ ID NO: 8) | Nicking enzyme *Staphylococcus aureus* | 4HT4 | 25.9 | 6.7 | acgcgaacggaacgttc gcataagtgcg/cccttacgg gatttaac (SEQ ID NO: 11) |

[&]slash (/) denotes site of cleavage by endonuclease
*Vega-Rocha et al., J. Mol. Biol. 367, 473-487 (2007).
{circumflex over ( )} Vega-Rocha et al., Biochemistry 46, 6201-6212 (2007).
Boer et al., EMBO J. 28, 1666-1678 (2009).
+Datta et al., Structure/Folding and Design 11, 1369-1379 (2003).
°Monzingo et al., J. Mol. Biol. 366, 165-178 (2007).
@Edwards et al., Proceedings of the National Academy of Sciences 110, 2804-2809 (2013).

This disclosure describes adapting the HUH catalytic motif for capsid protein tagging. The tags robustly form covalent complexes with DNA oligonucleotides. The catalytic residue of an HUH endonuclease can be a tyrosine that forms a phosphotyrosine ester with the target DNA.

As noted above, the HUH catalytic motif includes the metal-coordinating histidine residue or residues and a catalytic polar amino acid residue. Thus, a capsid fusion polypeptide can include any functional fragment of an HUH polypeptide. A functional fragment of an HUH polypeptide will include the metal-coordinating histidine residue or residues and the polar amino acid residue and sufficient additional amino acids to allow the fragment to possess DNA nicking activity.

In addition to or as an alternative to the sequences in Table 2, fragments thereof, such as amino acids 69-99, optionally with a deletion of amino acids 46-55, of SEQ ID NO:2, amino acids 6-126 of SEQ ID NO:4, amino acids 6-101 of SEQ ID NO:6, amino acids 7-97 of SEQ ID NO:7, amino acids 12-98 of SEQ ID NO:20, or amino acids 11-101 of SEQ ID NO:21, an HUH polypeptide can include one or more amino acid sequence modifications compared to the listed amino acid sequences. In certain cases, the amino acid sequence modification can include a deletion of one or more amino acid residues such as, for example, deletion of one or more of amino acids. In other cases, an amino acid modification can include a conservative amino acid substitution. A conservative substitution for an amino acid in a reference amino acid sequence may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Conservative substitutions include, for example, Lys for Arg or Arg for Lys to maintain a positive charge, Glu for Asp or Asp for Glu to maintain a negative charge, Ser for Thr so that a free —OH is maintained, and Gln for Asn to maintain a free —NH$_2$. Likewise, biologically active analogs of a polypeptide containing deletions or additions of one or more contiguous or noncontiguous amino acids that do not eliminate a functional activity of the polypeptide are also contemplated.

An HUH polypeptide also can be designed to provide additional sequences, such as, for example, an addition of one or more amino acid residues added C-terminal or N-terminal amino acids that would facilitate purification by trapping on columns or use of antibodies. Such tags include, for example, histidine-rich tags that allow purification of polypeptides on nickel columns. Such gene modification techniques and alternative suitable additional sequences are well known in the molecular biology arts.

An advantage of using HUH-tag fusion partners is that there are several classes of HUH-endonucleases with divergent structures, DNA recognition motifs, and/or functions. This characteristic allows which allows one to design a panel HUH-based fusion polypeptides, each of which binds to a distinct sequence of ssDNA, for use in, for example, multiplexed labeling of multiple species in a single reaction.

The HUH endonuclease-based protein tags allow one to orthogonally label proteins in cells.

Conventional protein tags that employ small protein modules based on DNA repair enzymes that form a covalent bond with DNA must do so through a modified DNA base. In contrast, the HUH tags recognize a specific sequence of standard nucleotides rather than modified bases. The conventional protein tags also use a catalytic cysteine, which can be prone to deactivation by oxidation. In contrast, as discussed above, HUH endonucleases use a catalytic tyrosine residue, which is less vulnerable to deactivation than cysteine. Many of the HUH proteins are smaller (100 amino acids) than conventional (e.g., SNAP/CLIP (New England Biolabs, Inc., Ipswich, Mass.) or HALOTAG (Promega, Madison, Wis.)) protein tags, so they may be less disruptive to protein function than the larger conventional tags, which can be 200-300 amino acids in size.

Designing the target sequence for a particular HUH-tag can enhance yield of covalent complex and/or specificity. Moreover, an HUH-endonuclease may be designed. e.g., by amino acid mutation, to alter DNA sequence specificity.

Example 2

Methods
Parallel Construction of Antibody/AAV Composites

AAV capsids are engineered to remove endogenous tropism and introduce conjugation handles. The majority of known receptors that AAV binds prior to endocytosis are proteoglycans through the heparin binding domain (HBD) (summarized here: (Nonnenmacher et al., 2012)). The engineering of viral capsid proteins is challenging; alterations must be compatible with assembly of viral particles, and must not interfere with internalization and trafficking to the nucleus. The development of a packaging system providing wild-type VP1 and VP3 in trans enabled the insertion of large protein domains at the N-terminus of VP2 without affecting packaging and infectivity (Warrington et al., 2004).

Figure 1A:
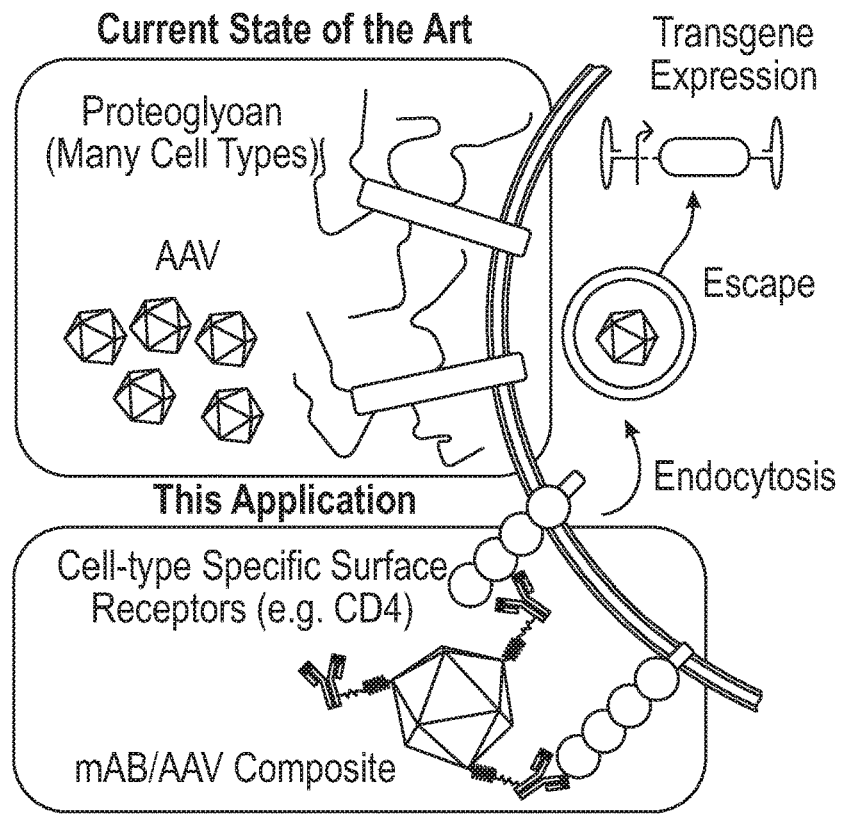
FIG. 1A. A method to redirect viral tropism vectors delivering transgenes towards cell-type specific receptors in a user-programmable and multiplexable way.
Figure 1B:
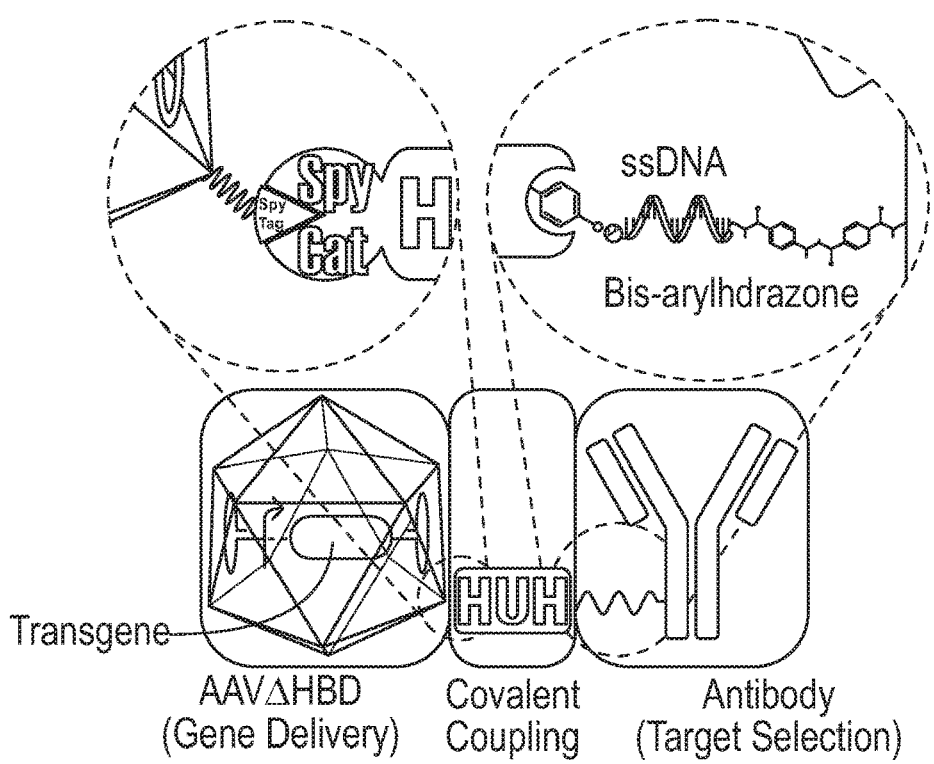
FIG. 1B. Covalently linked composite structures contain an AAV particle (packaging the delivered transgene) and an antibody that selectively binds cell-type specific surface markers. A HUH domain bridges the two components and confers programmable assembly. Insets provide further detail on HUH domain display on the capsid surface in one embodiment (via covalent SpyTag/SpyCatcher linkage), and HUH/antibody linkage (formation of a phosphotyrosine adduct with hydrazone-conjugated ssDNA-mAB).
Figure 2A:
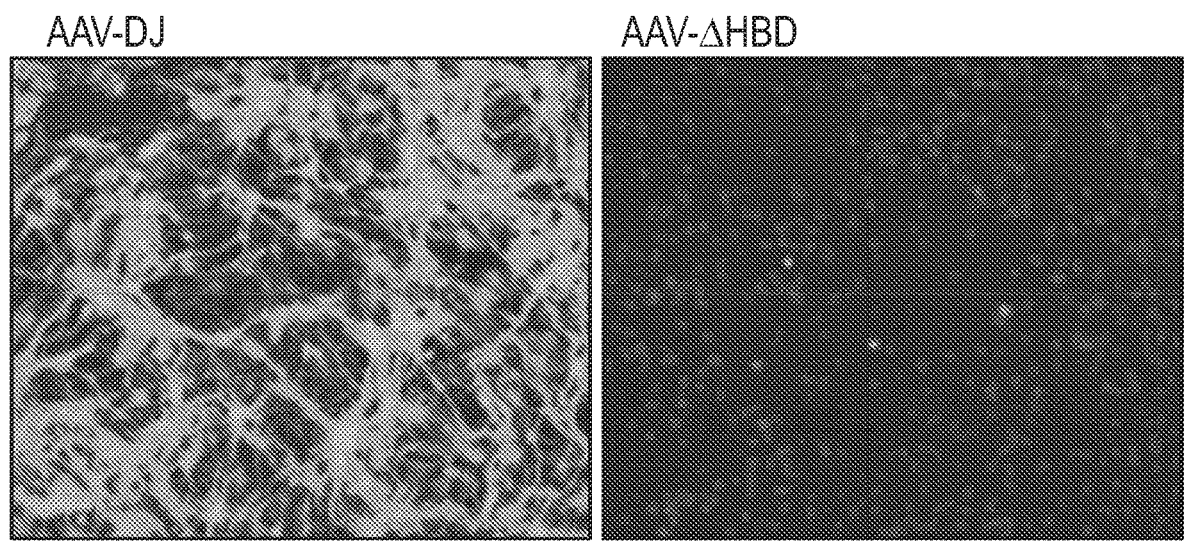
FIGS. 2A-D. A) Hippocampal neurons infected with wild-type virus (AAV-DJ), virus carrying mutations that interfere with neuron binding (AAV-ΔHBD). Reporter: GFP; nuclei strained with Hoechst 33342. B) Quantification of virus titer. Median (red bar). C) Cartoon of reaction chemistry showing catalytic tyrosine in HUH endonuclease nicking ssDNA (SEQ ID NO:60) and forming a covalent phosphotyrosine adduct. SDS-PAGE showing formation of covalent adduct between HUH protein and target oligonucleotide in the presence of $Mn^{2+}$ and EDTA. D) Heat map of DNA target sequence preferences of HUH-tags. Indicated HUH proteins were incubated individually with a 10-fold excess of preferred oligonucleotide target sequence preferences of HUH-tags. Indicated HUH proteins were incubated individually with a 10-fold excess of preferred oligonucleotide target sequences for each HUH protein; the reaction products were analyzed by SDS-PAGE and quantified.

To demonstrate that the endogenous tropism of AAV can be removed, mutations were introduced in the HBD domains of all capsid proteins. After packaging, the infectivity of AAV-ΔHBD was compared, and it was unable to deliver a genetic payload (GFP in this case) to any appreciable degree (FIG. 2A). qPCR confirmed that viral titers of AAV-ΔHBD were comparable to those of wild-type virus (FIG. 2B), demonstrating the introduced mutations do not interfere with virus packaging.

The HBD of AAV-DJ was removed in order to ablate the virus' natural tropism and it was replaced with the 13-AA SpyTag peptide, a short peptide that forms an isopeptide bond upon encountering its protein partner SpyCatcher. This provides a site for later covalent attachment to SpyCatcher-HUH. To verify integrity of viral capsids containing this modification, virus is produced by helper-free transfection of HEK293FT cells using established protocols (Grieger et al., 2006). Viral particles are collected from supernatant by polyethylene glycol (PEG)/aqueous two-phase partitioning (Guo et al., 2012). Titers are determined by qPCR or ddPCR. Three stocks of AAV-ΔHBD are produced, each encoding a different fluorescent protein (mTagBFP, GFP, mRuby) compatible with multi-color flow cytometry under a strong promoter (CAG, or SFFV and CMVI as alternatives) shown to be efficient in B cells and T cells (Zhang, 2013).

Recombinant Production of Three HUH Endonuclease Domains

Figure 2B:
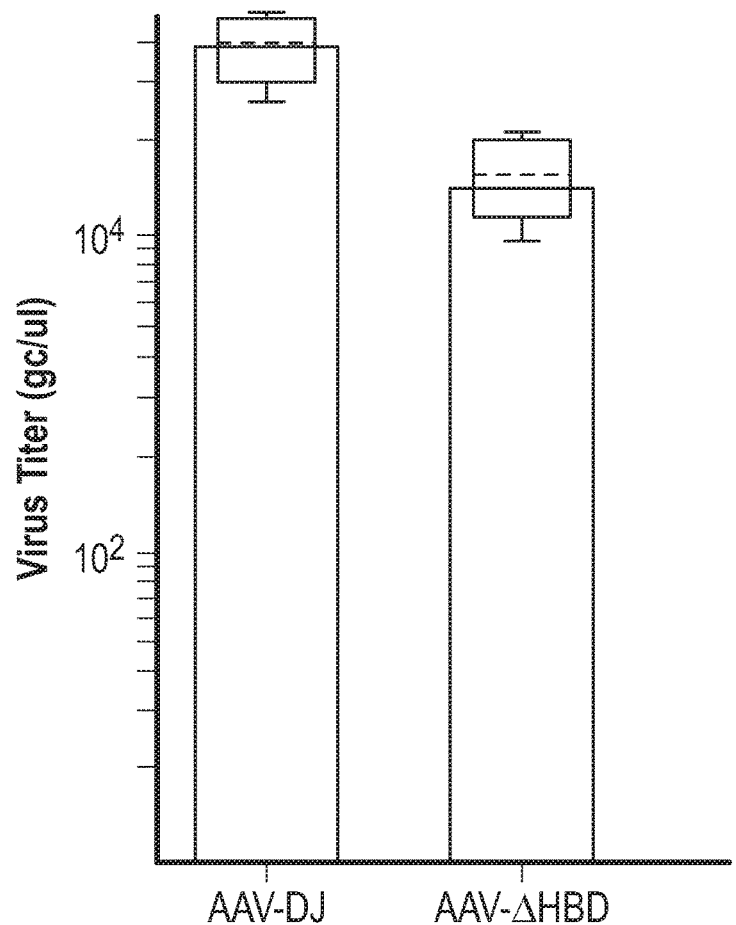
Figure 2C:
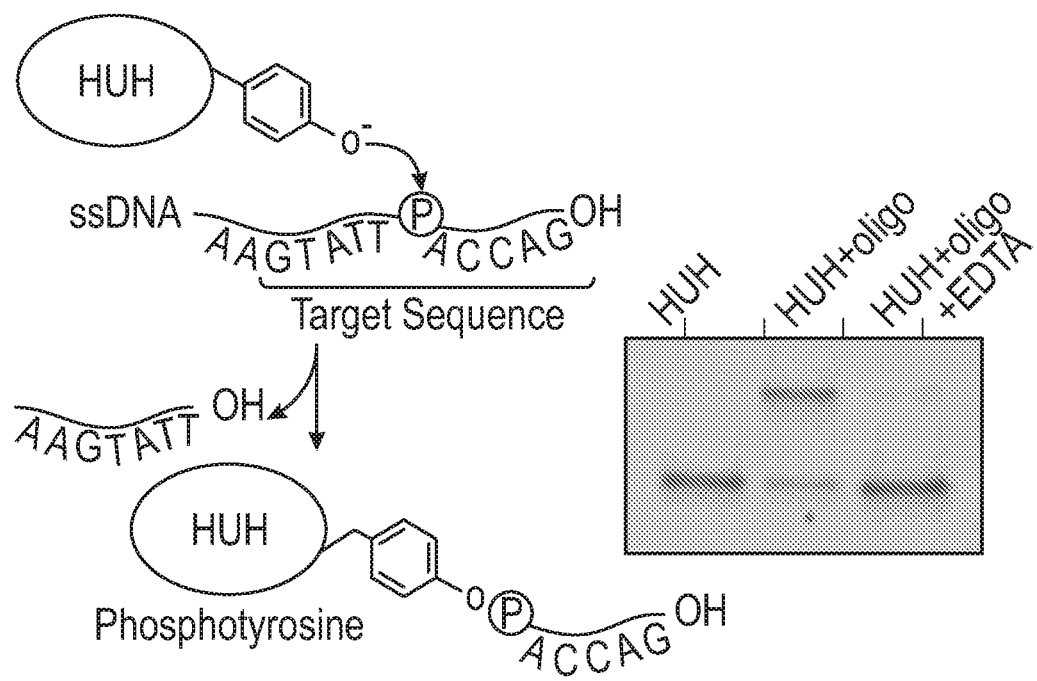
Figure 2D:
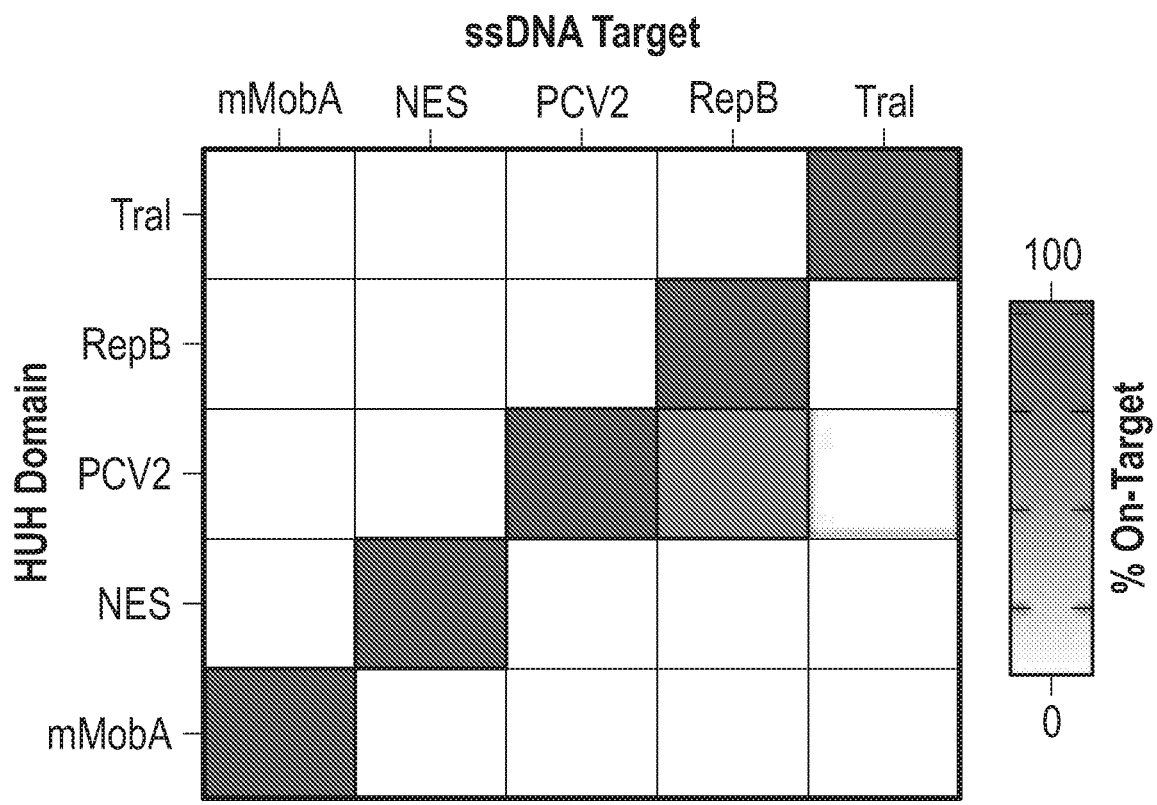
Figure 3:
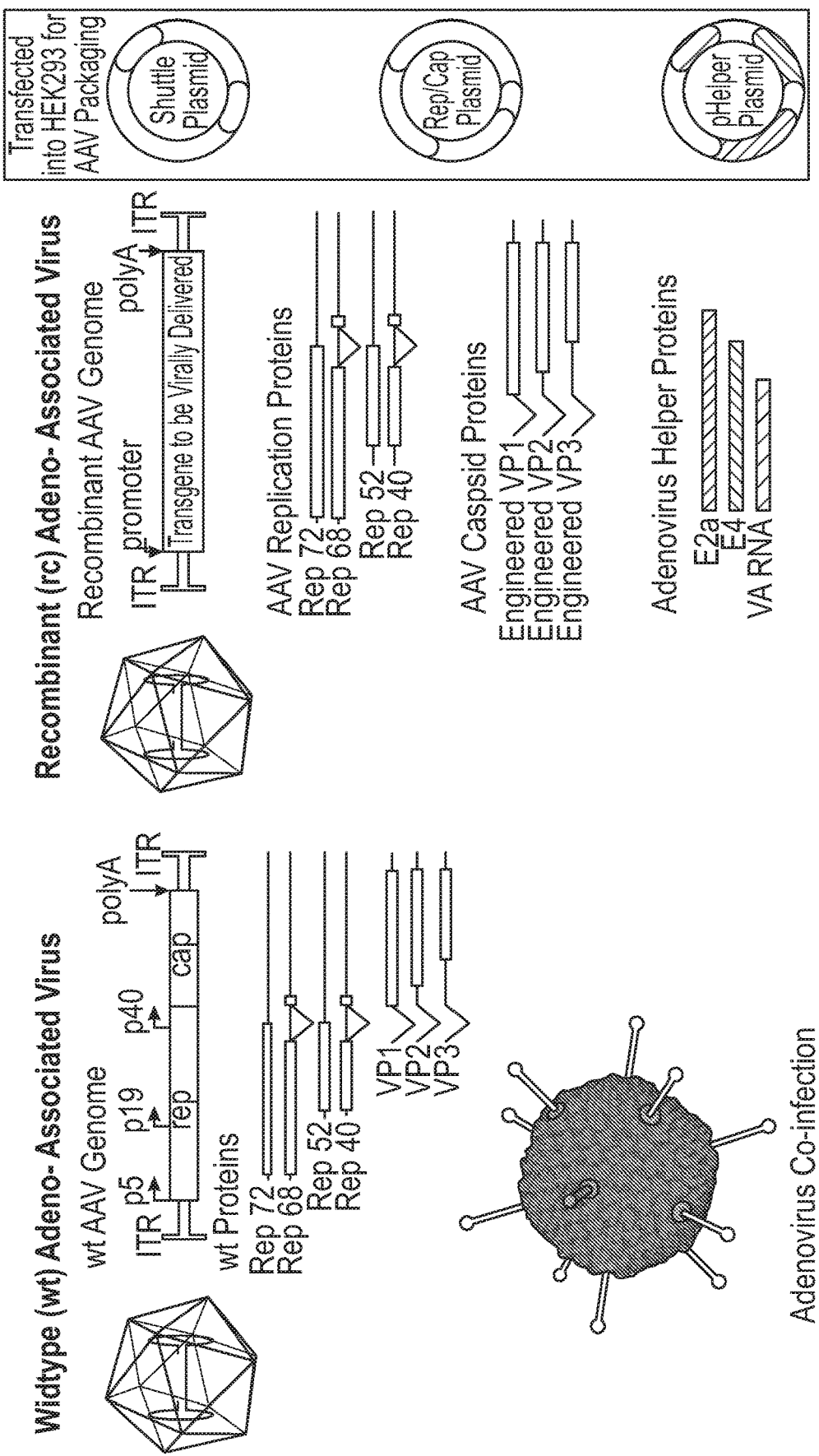
FIG. 3. A comparison of wildtype and recombinant Adeno-Associated Virus (AAV). Left: Wildtype AAV consists of a proteinaceous capsid that encapsulates a single copy of the ssDNA AAV genome, flanked by two Internal Terminal Repeats (ITRs). The genome consists of two genes (rep & cap) that are driven from endogenous promoters (p5, p19, etc) to encode multiple protein products (Rep 72, Rep68, etc.) whose open reading frames are indicated by thick lines. Splicing sites are connected by blue lines. AAV requires helper proteins (in a wildtype setting delivered by a Adenovirus—Ad—superinfection) to initiate viral replication. While the Rep protein product regulates the replication of viral genomes, capsid proteins VP1, VP2, and VP3 assemble in a 1:1:8 ratio to form new viral capsid. Right: Recombinant and replication-incompetent AAV (rAAV), able to deliver arbitrary transgenes (<4.2 kb), can be produced without the need for helper virus (Ad) by HEK293 cells transfected with multiple plasmids. One, a shuttle plasmid that encodes the transgene to be packaged by the rAAV which is flanked by AAV ITRs. Two, a plasmid that encodes AAV rep & cap genes. Cap genes are modified so they encode engineered capsid proteins compatible with forming mAB/AVV composites in a user-programmable fashion. Three, a helper plasmid that encodes helper virus (Ad) proteins allows for AAV replication and packaging.
Figure 4:
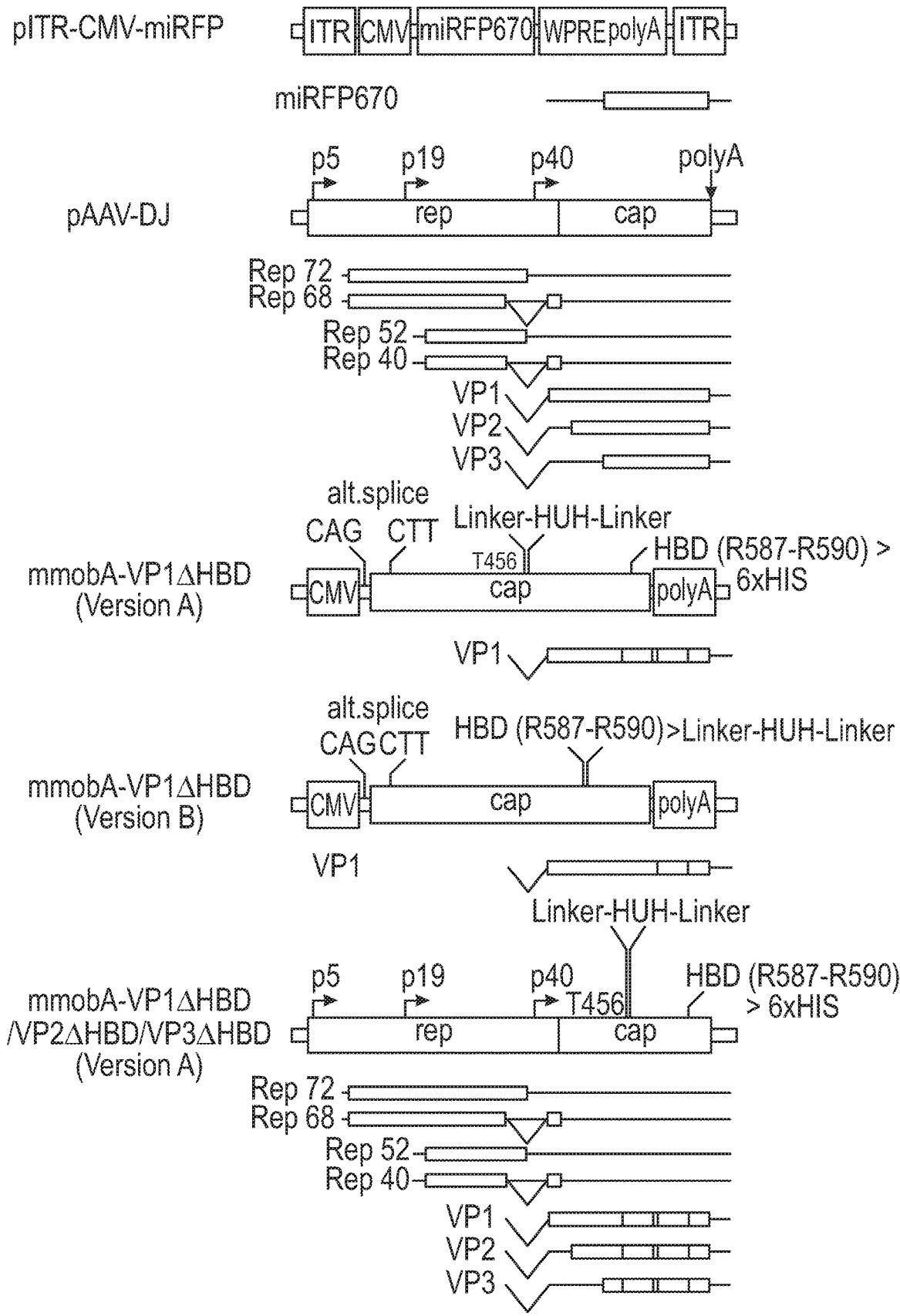
FIG. 4. A description of plasmids used in the production of recombinant AAV that is compatible with the formation of programmable AAV/antibody composites. The name of the plasmid is shown on the left; refer to the main text for a detailed workflow on how each plasmid was constructed. Shown to the right of the names is the DNA-level plasmid map, which includes promoters, genes, and other regulatory elements (WPRE, polyA). Approximate position modifications are indicated by vertical lines. The protein products that are transcribed and translated from each plasmid are listed below. Splicing sites are connected by blue lines.
Figure 4:
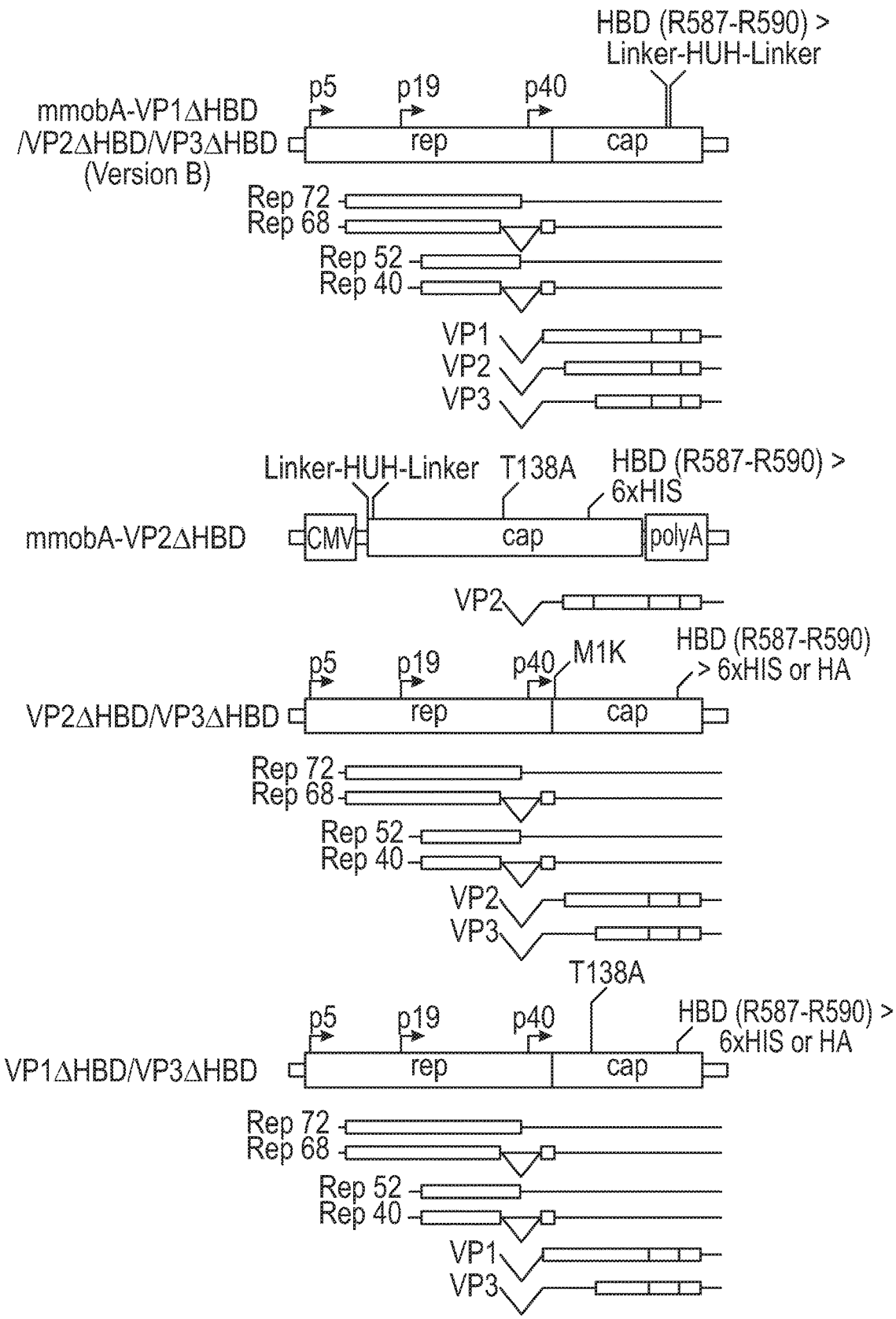
Figure 5A:
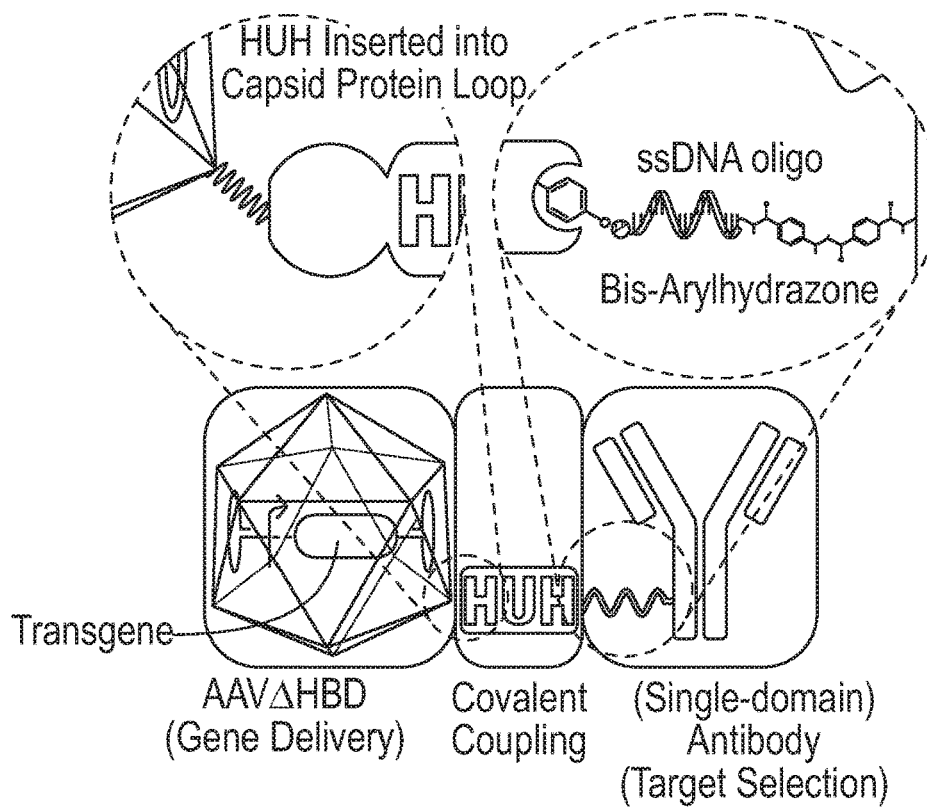
FIG. 5. Two example methods of how AAV/antibody composites are formed. (A) In one implementation the target-specific antibody is decorated with ssDNA via commercially available hydrazone-chemistry based oligonucleotide conjugation kits (e.g., Innova Biosciences). A HUH domain specific to the oligo sequence used in this conjugation covalently attaches via phosphotyrosine linkage to the ssDNA conjugated to the antibody via tyrosine in the HUH domain's active site. If this HUH domain is covalently linked to the rAAV capsid surface—through genetic engineering of capsid proteins VP1 and/or VP2 and VP3—this results in covalently linked composite structures containing an AAV particle (packaging the delivered transgene) and an antibody that selectively binds cell-type specific surface markers. (B) In another implementation a protein that has innate target specificity (e.g. nanobody, DARPin, etc.) and that can be produced recombinantly, is genetically fused with the SNAP protein (New England Biolabs). The SNAP protein covalently binds to a ssDNA oligo that is modified with a benzylguanine base. The remaining steps are the same as for (A).
Figure 5B:
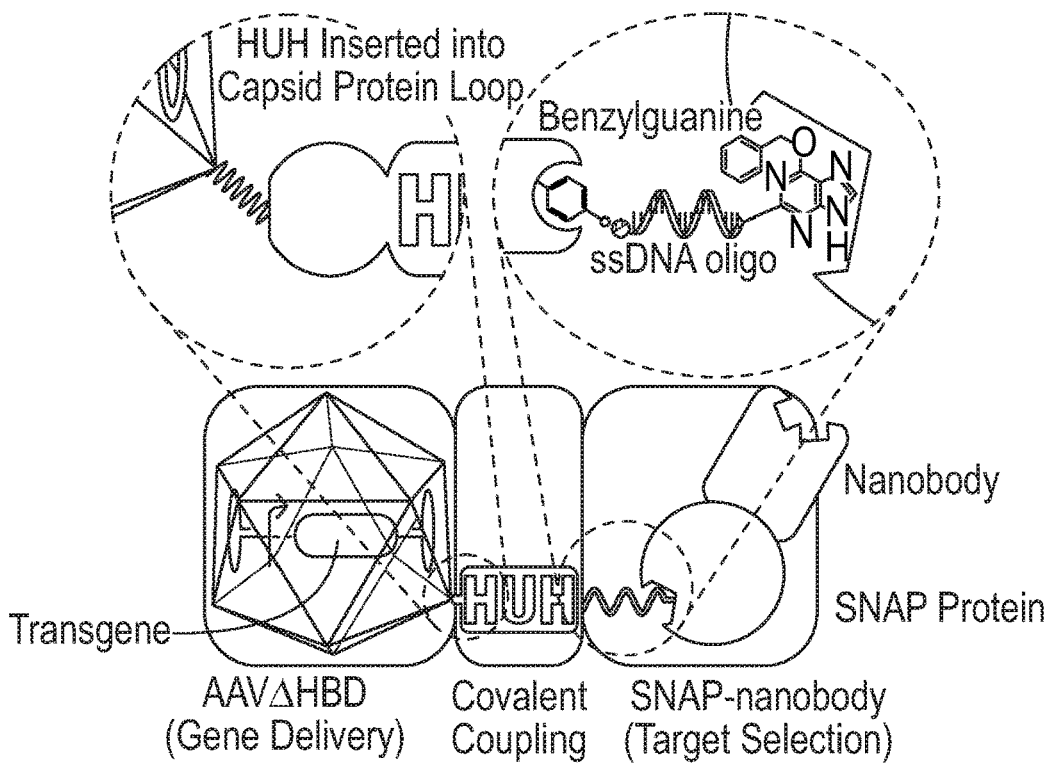
Figure 7:
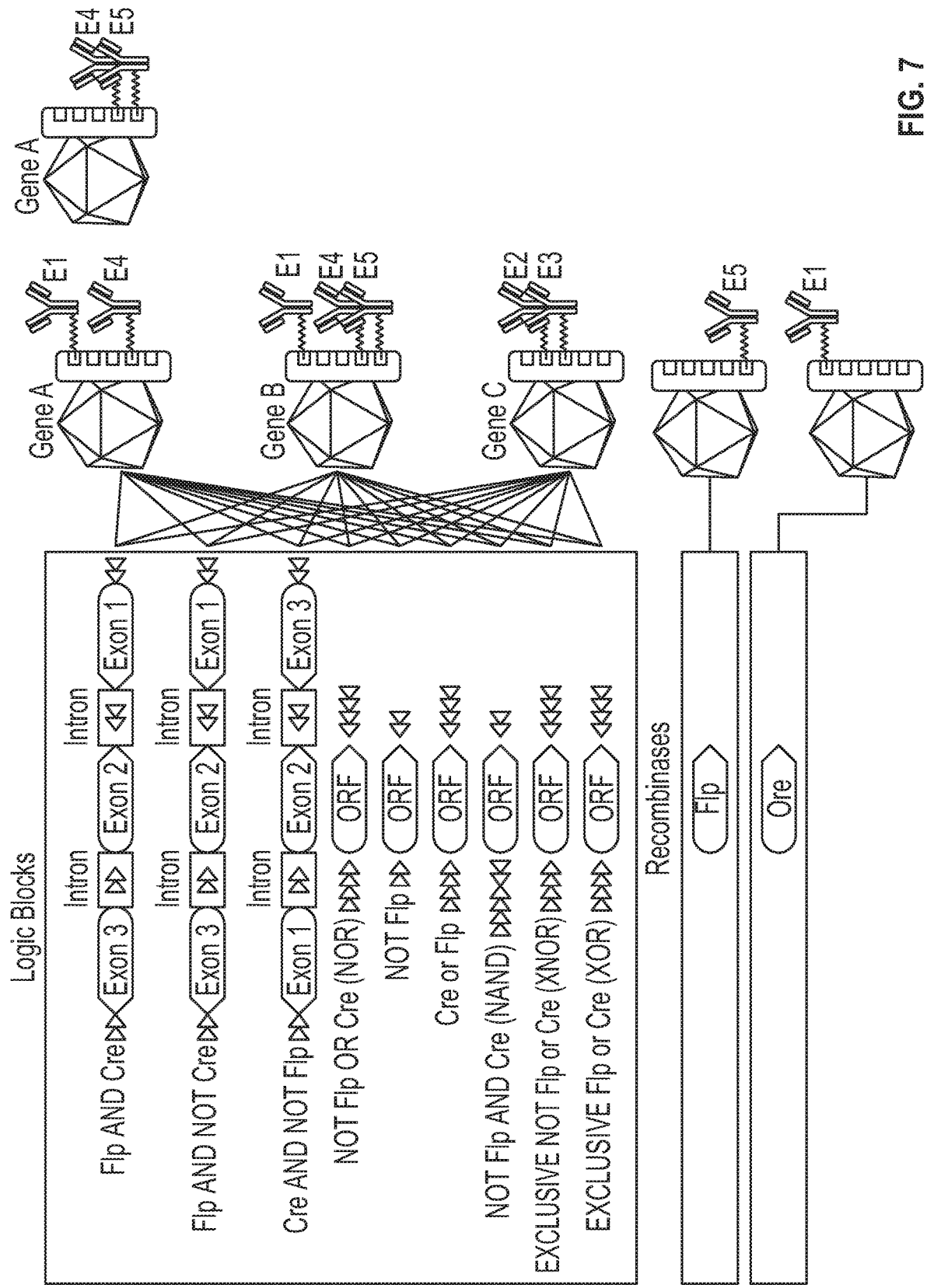
FIG. 7. Schematic of multiplexing genes and targeting molecules. If the application requires the delivery of different transgenes (Gene A, Gene B, etc.) in a single application/dose to different populations of cells (shown here regulatory T cells, regulatory B cells, and Lymphoma cells) that are characterized by expressing on the surface partially different & partially overlapping epitopes (E1, E2, E3, etc), packaged transgenes can be put under binary on/off control of recombinases that, depending on arrangement, implement different logic functions (Fenno et al., 2014). For example, a transgene arranged with site-specific recombinase recognition sequences to form a [Flp and not Cre] logic, is only activated in cells that are only infected with Flp recombinase, not cells that are transfected with (1) only Cre, (2) both Flp and Cre, or (3) neither. By displaying on the surface of unarmed viral stocks packaging these transgenes different concatenated HUH domains that have non-overlapping ssDNA specificity (shown as different colors), one can then devise an antibody/AAV linkage scheme for both transgene-delivering and recombinase-delivering viruses to infect specific subsets of cells in accordance to the specificity of linked antibodies. Whether transgenes are active or inactive in these subset of cells depends on the logic gate used in their construction and the presence or absence of recombinase.
Figures 9A, 9B:
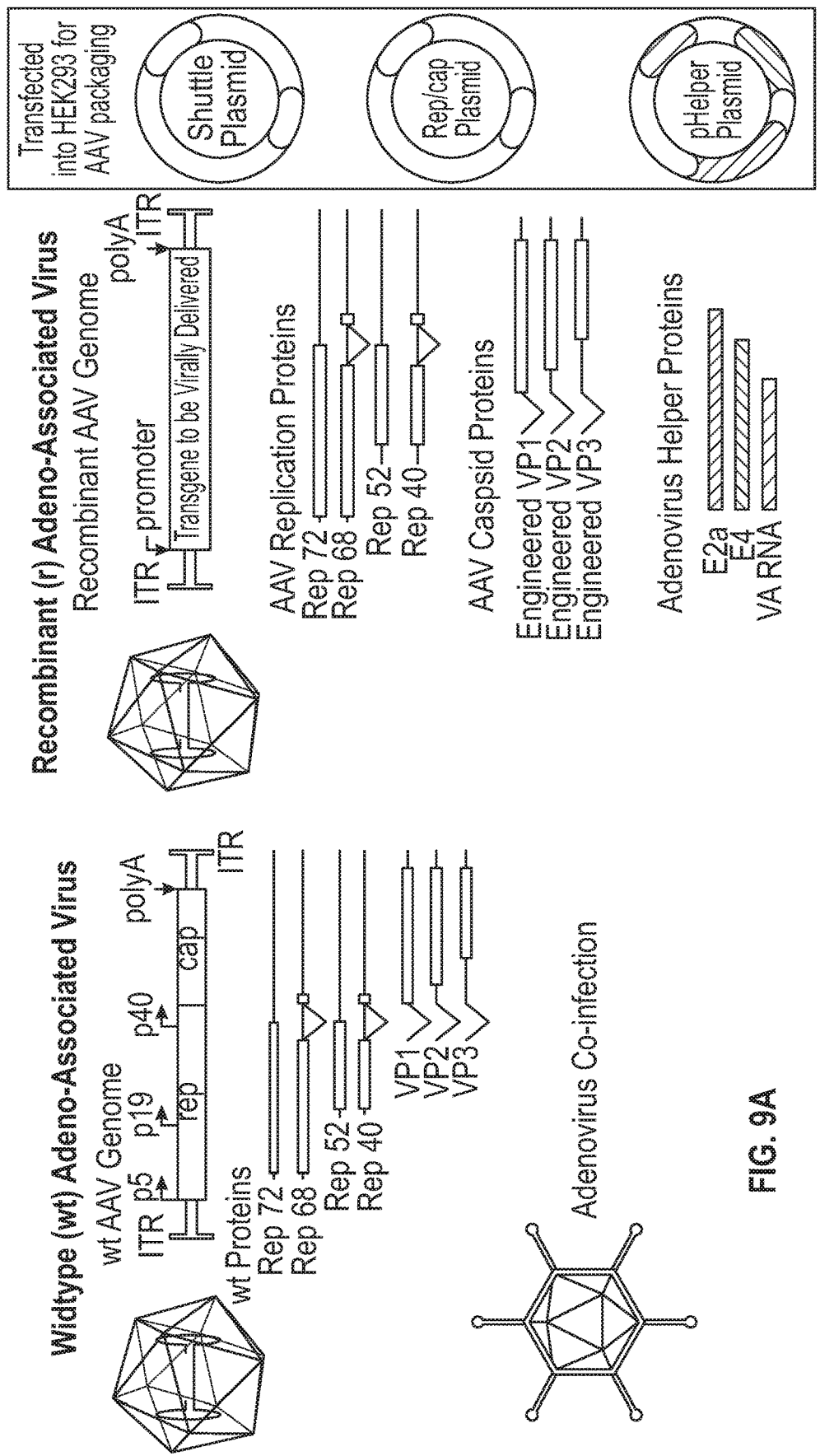
FIGS. 9A-B. A comparison of wildtype and recombinant adeno-associated virus (AAV). Left: Wildtype AAV has a proteinacous capsid that encapsulates a single copy of the ssDNA AAV genome, flanked by two internal terminal repeats (ITRs). The genome has two genes (rep & cap) that are driven from endogenous promoters (e.g., p5, p19, etc.) that encode multiple protein products (e.g., Rep72. Rep68, etc.) whose open reading frames are indicated by thick lines and splicing sites are connected by blue lines. AAV requires helper proteins (in a wildtype setting delivered by an adenovirus (Ad) superinfection) to initiate viral replication. While Rep protein regulates the replication of viral genomes, capsid proteins VP1, VP2, and VP3 assemble in a 1:1:8 ratio to form the viral capsid. Right: Recombinant AAV, able to deliver transgenes (e.g., <4.7 kb), can be produced without the need for helper virus (Ad) by transfection of HEK293 cells with one or more vectors. e.g., three different vectors such as plasmids. For example, a shuttle plasmid that encodes the transgene to be packaged by the rcAAV, a plasmid with genetically modified cap genes that encode engineered capsid protein compatible with forming AAV/ antibody composites in a user-programmable fashion, and a helper plasmid that encodes Ad protein required for AAV replication and packaging.
Figure 10C:
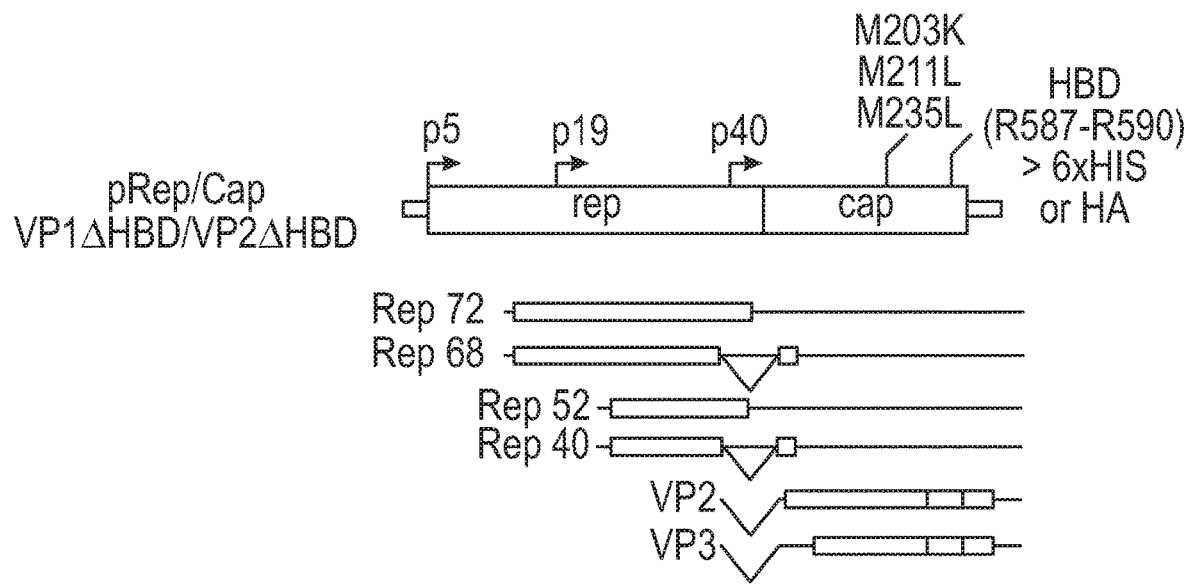
Figure 10D:
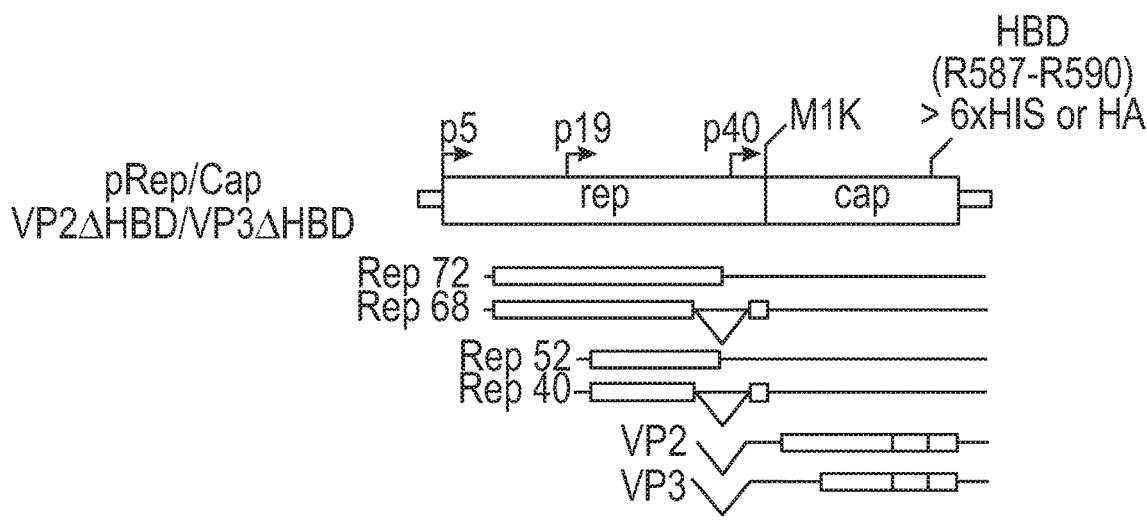
Figure 10F:
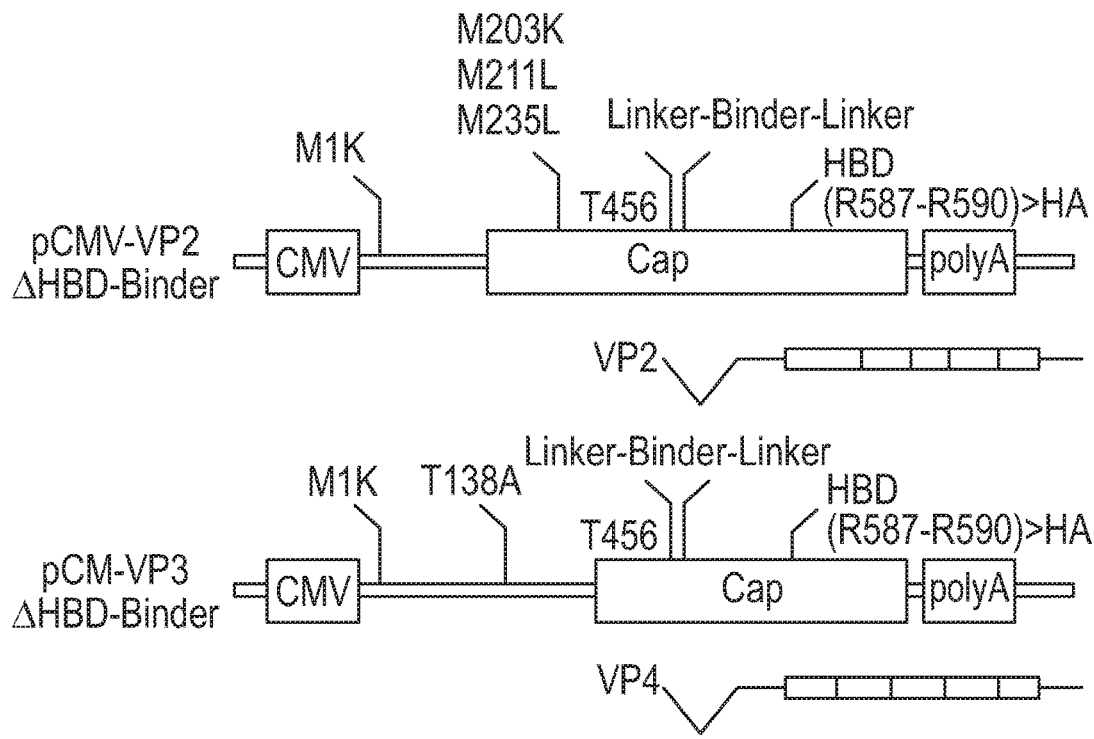
Figure 10G:
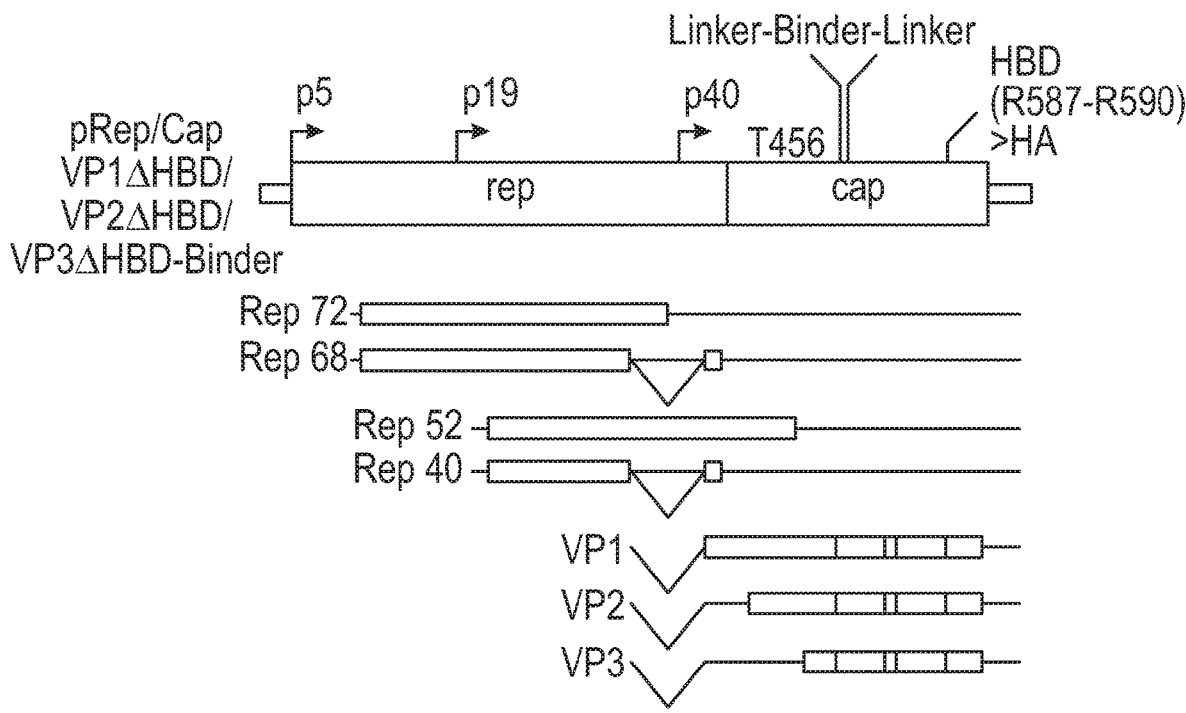

Small proteins called HUH domains robustly form covalent phosphotyrosine bonds with short specific ssDNA sequences (FIG. 2C). This disclosure exploits the multiplexability of these tags, as five HUH proteins have been identified that bind unique DNA sequences (FIG. 2D). Expression vectors for a set of 3 HUH endonuclease carrying a 6×HIS tag and fused to SpyCatcher are constructed in a pTD68 backbone (Uehara et al., 2010). Recombinant HUH protein is produced heterologously in E. coli using standard affinity purification methods.

Antibody Conjugation with ssDNA

Oligos containing the binding sequence of each HUH carry an internal fluorescent base (to monitor binding to HUH and trafficking) in addition to a 3' amino modification. The latter provides for a chemical handle to conjugate commercially available antibodies to the respective oligo via hydrazine/aldehyde conjugation chemistry (Solulink). Fully oligo-conjugated antibody is separated from unconjugated components by filtration.

Formation of Covalently Linked Antibody/AAV Composites

SpyTag-AAV is combined with SpyCatcher-HUH to form HUHAAV in mild conditions previously described to be conducive to formation of the SpyTag-SpyCatcher isopeptide bond (Zakeri et al., 2012). In this system, a widely-used form of irreversible peptide/protein ligation, SpyTag forms a spontaneous amide bond upon binding SpyCatcher at physiological pH and salt concentration. Next, excess oligo-labeled antibody is added to HUH-AAVs in the presence of Manganese and/or Magnesium. Fully assembled composite antibody-HUH-AAV are separated from any unreacted SpyCatcher-HUH or antibody by size exclusion chromatography or dialysis.

Results

The strategy to arm viruses containing therapeutic payloads with user-defined specificity to antigens on three or more different cell-types has many applications to pediatric diseases. For example, this would provide improved and "off-the-shelf" T-CAR immunotherapy that deliver T-CARs to both CD4 and CD8 T-cells and a toxic payload to T-Regs. Genes expressing three different fluorescent proteins were delivered to three different cell-types in blood. The overall strategy involves decorating AAV's with three different HUH-tags, which subsequently form covalent bonds to single-stranded DNA oligos conjugated to antibodies to antigens on the three different cell-types. Recombinant AAV is produced in helper-free mammalian cell culture, and HUH adapters are expressed as recombinant protein in E. coli. Amino-chemistry is used to conjugate ssDNA to antibodies. Adeno-associated virus, a major gene delivery vector for gene therapy, is used as a model virus.

In one embodiment, the approach entails the following:
1) Remove endogenous tropism of AAV and insert SpyTag into surface exposed loops of capsid protein VP and/or VP2; produce three non-infectious recombinant AAVs that package three different fluorescent proteins.
2) Produce and purify three distinct HUH endonuclease domains genetically fused to SpyCatcher as heterologous proteins in E. coli, and covalently link each HUH type to an AAV type.
3) Conjugate ssDNA specific for HUH endonucleases used above to antibodies that recognized surface marker of different cell types found in human peripheral blood.
4) In a single reaction, produce three types of covalently linked mAB/AAV composites.
5) Validate cell-type specific infection of peripheral blood lymphocytes by flow cytometry.

To construct a set of AAVs that display on their capsid surface different ssDNA-binding proteins, which covalently bind to ssDNA-linked antibodies in a sequence-specific fashion, endogenous tropism of AAVs is removed by mutations in the respective glycan-binding loops of capsid proteins (VP1-VP3). In their place, a peptide fragment is introduced (SpyTag) that irreversibly attaches to the viral capsid ssDNA-binding HUH endonuclease domains that fused to SpyTag's cognate binding partner (Spy Catcher) (Zakeri et al., 2012). Antibodies that then form HUH-specific covalent bonds with such modified AAV are produced through established oligo-conjugation chemistry.

To demonstrate multiplexed gene delivery to increasingly complex tissue with minimal cross-talk, viral transduction is tested on cultured lymphocytes. Individual cell types (B cells, CD4+ T cells, CD8+ T cells) are targeted by widely used antibodies (α-CD20, α-CD4, and α-CD8) covalently linked to AAV, which deliver different fluorescent reporters (mTagBFP, GFP, mRuby). Specificity and efficiency of transduction is analyzed by flow-cytometry.

Summary

Many of the strategies employ precursor components that are then combined into mAB/AAV composites. High-titer ($>10^8$ infectious particles/µL) virus in helper-free packaging systems is provided. Since the introduction of a SpyTag into the viral capsid at a defined position is a small modification (13AA), the modified capsid is stable and the helper-fre population has ratio of empty/full capsids comparable to wildtype AAV (50:1-20:1) before further downstream purification. Production of recombinant HUHSpyCatcher fusions is a straightforward heterologous expression and high yields are likely given that HUH endonuclease has been shown to express well with N- and C-terminal fusions. Conjugation of ssDNA to antibodies also has high yield. Even if three HUH domains are displayed in a single AAV, not every domain may react covalently with a ssDNA-conjugated antibody.

Alternative insertion sites, e.g., VP1 position 453-458 or VP2 N-terminus, that accept large, e.g., 30 kDa, additions (Warrington et al., 2004, Boucas et al. 2008), may be employed. Other protocols and commercial conjugation kits, or different conjugation chemistries may be employed.

Example 3

Peripheral blood mononuclear cells (PBMCs) include multiple different hematopoietic cell types including T-cells. B-cells, monocytes, and NK cells. Gene editing of hematopoietic cells is highly relevant to both gene therapy and cancer immunotherapy Thus, PBMCs provide opportunity for testing the efficacy and selectivity of multiplexed gene delivery with antibody/AAV composites in a complex environment ex vivo.

Commercially available PBMCs are cultured in chemically defined, serum-free media (Lonza). A composite AAV that targets CD20 on B-cells and both CD4 and CD8 on T-cells is prepared. Each marker-specific AAV delivers a transgene for a different fluorescent protein. Thus, successful transduction of targeted cell types generate blue B-cells (mTagBFP), green CD4 T-cells (GFP), red CD8 cells (mRuby), and yellow CD4/CD8 T-cells (GFP/mRuby). The three different AAVs are combined (adjusting for virus titer) and incubated with freshly thawed PBMCs at different multiplicities of infection in serum free media. After 1 hour, the PBMCs are washed to remove any remaining AAVs particles and re-suspended in complete media.

Allowing for onset of fluorescent reporter expression, the PBMCs are then assessed by flow cytometry after an additional 4-10 days of incubation. Fluorescent α-CD20, α-CD4, and α-CD8 antibodies are used that have non-overlapping emission spectra with the fluorescent proteins. Using this approach, the efficiency of up-take of AAV particles by the targeted cell type (i.e., % of CD20 cells that are also mTagBFP positive) as well as any off-target effects (i.e. non-CD20 cells that are also mTagBFP positive) is assessed.

Summary

The metric is high-efficiency on-target infection with minimal off-target infection, that is cell-type specific infection of multiple different cell types with mAB/AAV composites. A high, e.g., >90% transduction efficiency is expected, for on-target trials achievable with low multiplicity of infection (MOI<10).

The objective is to develop and bring to the clinic a new class of cell-type specific viral vectors that shifts treatment paradigms for pediatric cancer and other pediatric diseases. In order to reach the patient, cell-type specificity of engineered mAB/AAV composites that target lymphatic tissue surface markers is shown.

A technology capable of delivering a therapeutic product based on surface antigens is timely, as more antigens have been implicated in cancer in recent years. Similar to antibody-drug conjugates (ADCs), the present approach takes advantage of antigen-specific targeting. Unlike ADCs, viruses are stable in the bloodstream (especially if they are engineered to avoid innate serum responses) and are endocytosed readily and predictably. AAV is an ideal vector to use as it has a low immunogenic response and its capsid has been shown to tolerate insertions (Warrington et al., 2004; Wu et al., 2000; Boucas, 2008; Zhang et al., 2002). The small size of AAV is appealing, as it is capable of penetrating solid tissues, a characteristic unique to AAV among other commonly clinically used viral vectors (Enger et al., 2002). The present technology provides for targeting multiple cell types simultaneously, and it would streamline the production of viral vectors required to do so.

Example 4

Note that while the use of one exemplary HUH domain (mMobA) is described below, this method applies to all HUH domains that can be used, e.g., see Lovendahl et al. (2017), which is incorporated by reference herein.

Strategy A; HUH Domain is Genetically Fused to VP1 Only

Plasmid 1 (mMobA-VP1ΔHBD). The cap gene derived from pAAV-DJ (Grimm et al., 2008) was cloned into a mammalian expression vector under CMV promoter control. An alternative splice acceptor TT(UU) was introduced to suppress expression of VP2/3 (Muralidhar et al., 1994), Heparin-binding domains present in VP1 were removed by replacing amino acids R587-R590 with a hexahistidine tag. A DNA fragment encoding the HUH domain (e.g., mMobA) flanked by flexible linkers (e.g., GGGGS; SEQ ID NO:65) was inserted between T456 and 145 in VP1. Alternatively, the HUH may be inserted between Q586 and Q591 in place of the heparin binding domain and the hexahistidine tag.

Strategy B: The HUH Domain is Genetically Fused to all Three Capsid Proteins (VP1/2/3)

Plasmid 2 (mMobA-VP1ΔHBD/VP2ΔHBD/VP3ΔHBD). To insert the HUH domain into all three capsid protein that assemble into a viral particle, the cap gene derived from pAAV-DJ (Grimm et al., 2008) was cloned into a mammalian expression vector under CMV promoter control. Heparin-binding domains present in VP1/VP2/VP3 were removed by replacing amino acids R587-R590 (VP1 numbering) with a hexahistidine tag. A DNA fragment encoding the HUH domain (e.g., mMobA) flanked by flexible linkers (e.g., GGGGS) was inserted between T456 and T457 in VP.

Alternatively, the HUH may be inserted between Q586 and Q591 in place of the heparin binding domain and the hexahistidine tag.

Strategy C; the HUH Domain is Genetically Fused to VP2 Only

Plasmid 3 (mMobA-VP2ΔHBD). A DNA fragment corresponding to VP2 was cloned into a mammalian expression vector under CMV promoter control. The start codon for VP3 was mutated (T138A). A DNA fragment encoding the HUH domain (e.g., mMobA) followed by a flexible linker (e.g., GGGGS) was inserted at the N-terminus of VP2.

Strategies that display the HUH only on one of the viral capsid proteins include the expression of the remaining capsid proteins in trans from their endogenous promoters.

Plasmid 4 (VP2/3ΔHBD-HIS6 or VP2/3ΔHBD-HA). A construct encoding AAV capsid proteins VP2 and VP3 was generated from pAAV-DJ (Grimm et al., 2008) by introducing the point mutation M1K, which knocks out expression of full-length VP1. Heparin-binding domains present in VP2/3 were removed by replacing amino acids R587-R590 with a Human influenza hemagglutinin (HA) tag—amino acids sequence YPYDVPDYA—or a hexahistidine tag. Either can be used in the composite/AAV production described below.

Plasmid 5 [VP1/3ΔHBD-HIS6 or VP1/3ΔHBD-HA]. A construct encoding AAV capsid proteins VP1 and VP3 was generated from pAAV-DJ (Grimm et al., 2008) by introducing the point mutation T138A, which knocks out expression of VP2. Heparin-binding domains present in VP1/3 were removed by replacing amino acids R587-R590 with a Human influenza hemagglutinin (HA) tag—amino acids sequence YPYDVPDYA—or a hexahistidine tag. Either can be used in the composite/AAV production described below.

lysate was treated with 0.1% deoxycholate and benzonase endonuclease (1.25 U/uL lysate, hour, 37° C.) to remove non-encapsidated genome and remaining genome-endoding plasmid. Lysate was then treated with proteinase K (1.6 U/uL, 1 hour, 37° C.) and heated to 95° C. for 10 minutes. Zymo Clean and Concentrator 5 was then used to generate pure DNA for qPCR.

Preparation of Recombinant Nanobody-SNAP pGFPnb-SNAP was transformed into *Escherichia coli* BL21(DE3) cells and grown overnight in LB supplemented with 100 ug/mL ampicillin. 5052 autoinduction media then was inoculated with starter culture and incubated 8 hours at 37° C. The culture was then incubated 24 hours at 25° C. Cells were pelleted and resuspended in lysis buffer (50 mM Tris HCl, 650 mM NaCl) and lysed by sonication on ice. Soluble GFP nanobody-SNAP was bound to Ni-NTA agarose resin at 4° C. for one hour. Resin was packed into a gravity flow column and washed with 10 column volumes of wash buffer (50 mM NaCl, 650 mM TrisHCl, 10 mM imidazole). Protein was eluted (50 mM TrisHCl, 650 mM NaCl, 250 mM imidazole) and dialyzed overnight into storage buffer (1 uM EDTA, 50 mM TrisHCl, 150 mM NaCl, 3 mM $NaN_3$, 10% glycerol). For conjugation to benzylguanine-oligo, nanobody was dialyzed into SNAP buffer (50 mM HEPES, 50 mM NaCl).

Preparation of ssDNA-BG

Lysophilized BG-GLA-NHS (NEB) was resuspended to 4.15 mM in DMSO. 3' amino-labeled mMobA ssDNA (IDT) was resuspended to 2.1 mM in nuclease-free water. ssDNA labeling reactions were prepared with 166 uM BG-GLA-NHS and 168 uM oligo in 0.1 M sodium borate pH 8.5. Reaction was incubated at 37° C. shaking for four hours.

TABLE 3

| | mMob A-VP1Δ HBD | mMobA-VP1ΔHBD/ VP2ΔHBD/ VP3ΔHBD | mMobA-VP2ΔHBD | VP2/3Δ HBD-HIS6 or VP2/3Δ HBD-HA | VP1/3ΔHBD-HIS6 or VP1/3ΔHBD-HA | pITR-CMV-miRFP | pHelper |
|---|---|---|---|---|---|---|---|
| Strategy A | X | | | X | | X | X |
| Strategy B | | X | | | | X | X |
| Strategy C | | | X | | X | X | X |

Helper-free virus production: AAV-DJ was generated using helper-free transfection of an AAV-packing HEK293 cell line (Cell Biolabs Inc.). Cells were plated at 30% confluence 24 hours before transfection in 100 mm cell culture dishes. Immediately before transfection, cell growth media was exchanged for 10 mL of DMEM supplemented with 9% fetal bovine serum. Cells were transfected via polyethaneimine with 15 ug total of plasmid encoding viral capsid proteins (see Table 3), a plasmid encoding the packaged transgene (e.g. pITR-CMV-miRFP), and pHelper, a plasmid that is encoding an adenovirus helper gene required for recombinant AAV packaging (Yakobson et al., 1987). Plasmid of each group was transfected at a 1:1:1 molar ratio. 48 hours after transfection, cells were detached, pelleted (3260rcf, 10 minutes), and flash-frozen in liquid nitrogen. Virus-containing cells were stored at −80° C. until use.

To collect virus, cells were frozen in liquid nitrogen and thawed in a 40° C. water bath four times.

Viral titer was measured via qPCR using genome plasmid as a standard. Briefly, an aliquot of virus-containing cell After incubation, 50 uL TrisHCl pH 8 and 900 uL 0.1×TE were added to quench NHS ester and raise the volume to 1000 uL. Reaction was concentrated to 100 uL using 100 kDa MWCO filter to remove unreacted BG-GLA-NHS.

Reaction of Nanobody-SNAP with ssDNA-BG

Recombinant nanobody-SNAP was reacted with ssDNA-BG in a ratio of 1:2 (protein:DNA) in SNAP buffer (10 mM DTT, 50 mM NaCl, 50 mM HEPES). Reaction was incubated at 37° C. for 30 minutes. To remove unreacted ssDNA, the reaction was batch-bound to Ni-NTA agarose resin. Resin was pelleted at 1000 ref, and washed RB2 (20 mM TrisHCl pH 8.0, 150 mM NaCl, 20 mM imidazole), HW2 (20 mM TrisHCl pH 8.0, 150 mM NaCl, 30 mM imidazole), and HW3 (20 mM TrisHCl pH 8.0, 150 mM NaCl, 40 mM imidazole). Protein was eluted in 500 mM imidazole (His-Elute, 20 mM TrisHCl pH 8.0, 150 mM NaCl, 500 mM imidazole).

Reaction of Nanobody-ssDNA with mMobA-Virus

Ni-NTA resin-purified nanobody-ssDNA, MgCl2 and MnCl2 were added to virus-containing cell lysate for a final reaction concentration of 50 mM MgCl2, 50 mM MnCl2, and 100 pM nanobody-ssDNA. Lysate was incubated shaking at 37° C. for 30 minutes. Reacted lysate was then added directly in infection assays, or further purified as described below.

Filter purification: after 30 minutes incubation, reaction was diluted by half in RB1 (150 mM NaCl, 50 mM TrisHCl pH 8.0) and concentrated using a 100 kDa MWCO filter (Amicon) to remove unreacted nanobody-ssDNA. Lysate was diluted to original volume to restore original titer.

In Vitro Infection Assays

HEK239FT cells cultured in DMEM supplemented with 10% FBS, sodium pyruvate, and antibiotics were transfected with pCAG-GFP-GPI (Kondon et al., 1999) resulting in expression of membrane-anchored GFP at the extracellular side of cell's plasma membrane. After 24 hours –48 hours growth media was removed, cells were washed twice with DMEM, and then composite virus was incubated with cells in DMEM for 1 hour at 37° C., at which point complete growth media was added. Infection was monitored by epifluorescence microscopy using appropriate settings for GFP (target) and miRFP670 (delivered transgene). To quantify expression levels, ROIs were drawn manually around GFP-expressing cells, and mean intensity of each ROI was measured in both GFP and miRFP channel. Negative controls included: HUH-displaying AAV that was incubated with anti-GFP nanobody that lacked the ssDNA modification. AAV with all heparin-binding domain removed. Posite controls included: wildtype AAV-DJ virus, HUH-displaying AAV in which the heparin-binding domains where not removed. Infectiousness of the latter demonstrates that the addition of HUH domains to the virus capsid do not interfere with endocytosis and endosomal escape. See FIG. 6.

Example 5

A specific example of use of the disclosed system is in pediatric cancer therapy where targeted simultaneous viral gene delivery to multiple cell-types would be game-changing is in Adoptive Cell Transfer (ACT) of bioengineered, chimeric antigen receptor T cells (T-CAR), which harnesses the patient's own immune system to fight cancer. In this approach, T-cells from a cancer patient are removed, virally engineered to recognize an antigen specific to the patient's cancer cells, expanded ex vivo, and then re-infused back into the patient where these T-CARs can recognize and kill the cancer cells expressing the targeted antigen (Barrett et al., 2014). Dramatic clinical responses have been observed in pediatric patients with relapsed or refractory blood cancers given CD19-recognizing T-CARs (Kalos et al., 2011; Porter et al., 2011a; Porter et al., 2011b). Two current limitations of the therapy are the laborious requirement of removing T-cells from the patient, and the highly immunosuppressive nature of the tumor microenvironment, in part due to T-regulatory cells, which can limit the toxicity of T-CARs despite recognizing the targeted antigen on the cancer cell. The novel technology in this proposal could overcome both of these challenges.

Ideally, a bio-banked, off-the-shelf toolbox would exist that enables genetic manipulation of specific cell populations in vivo with no off-target effects. For example, delivery of chimeric cancer antigen receptor CD4 and CD8 T-cell subsets has been shown to result in better clinical efficacy than either subset alone (Sommermeyer et al., 2016), and negative regulators of T-regs expressing both CD4 and CD25 (Golubovskaya, 2016; Duell et al., 2017). Viral gene delivery appears to be the best approach; however, many viral vectors have broad tropism to many tissues or are pathogens and require careful modification to become useful for therapy. Thus, there is need to develop safe viral vectors that target user-selectable set of cells without off-target effects. The targeting mechanism of these viral vectors needs to be robust, predictable, and generalizable to arbitrary surface markers. Re-targeting must be achievable through rational engineering, without the need for extensive screening.

Example 6

Genetic Engineering of Viral Capsid Proteins

Note that while here is described the use of one exemplary HUH domain (mMobA), this method applies to all know HUH domains that can be used as described in Lovendahl et al. (2017)

pCMV-Cap-Binder Expression Plasmid Creation

All primers were designed using NEBasechanger or NEBuilder. The CDS of all plasmids were sequenced fully by MCLabs (San Francisco). All preparations of DNA were analytical digested to confirm backbone integrity.

GFP nanobody plasmid was a kind gift of Sivaraj Sivaramakrishnan.

pCMV-cap was created by subcloning the cap open reading frame of AAV-DJ into a pcDNA backbone. The heparin binding domain (R587-R590) was mutated to an HA tag (YPYDVPDY) using NEB Q5 site-directed mutagenesis. To create plasmids individually expressing each VP, the start codons of the other two VPs individually mutated using NEB Q5 kit. M1K knock out expression of VP1. T138A to knock out expression of VP2, and M203K, M211L, and M235L to knock out expression of VP3. We found that it was necessary to mutagenize all three VP3 start codons to fully ablate expression (data not shown). Using these mutations, we created pCMV-VP1, pCMV-VP2, and pCMV-VP3 (collectively referred to as pCMV-VPx).

To create each cap-Bindery construct, pCMV-VPx was amplified starting at T456 and T457 with primers adding a $(G_4S)_2$ flexible linker on either side. Inserts were amplified with primers with a 15-base overlap with the flexible linkers. Both binding scaffolds (nanobodies and GP2) as well as HUH tags can be encoded in all three VPs.

Alternatively, the HUH may be inserted between Q586 and Q591 in place of the heparin binding domain and the hexahistidine tag.

TABLE 4

|  | VP1 | VP2 | VP3 |
| --- | --- | --- | --- |
| mMobA | 398 | 437 |  |
| RepBm | 439 | 440 |  |
| GFP nanobody | 395 | 396 | 397 |
| αInsR Gp2 | 447 | 448 | 449 | pCMV-cap-tag constructs created and plasmid numbers

Helper-Free Virus Production

Viruses were created by UMN Viral Vector Cloning Core (VVCC, Director: Kevin Wickham). HEK293 AAV cells at 60% confluence were transfected with DNA (pCMV-VPx, pRep/Cap, pHelper, pITR-CAG-tdtomato) using PEI. 24 hours after transfection, media was changed and cells were checked for fluorescent protein expression (when applicable) to confirm transfection success. 72 hours after transfection, cells were detached and pelleted (flash-frozen to lyse, virus purified on sucrose gradient, virus titered by qPCR using WPRE primers).

Example Strategy: HUH Domain is Genetically Fused to VP2 Only

Plasmid (pCMV-VP2ΔHBD-Binder). A DNA fragment corresponding to VP2 was cloned into a mammalian expression vector under CMV promoter control. The start codons for VP1 (M1K) and VP3 were mutated (M203K, M211L, M235L). A DNA fragment encoding the HUH domain (e.g. mMobA) followed by a flexible linker (e.g., GGGGS) was inserted at position 456.

Strategies that display the HUH only on one of the viral capsid protein require the expression of the remaining capsid proteins in trans from their endogenous promoters.

Plasmid 5 (pRep/Cap VP/3ΔHBD-HIS6 or pRep/Cap VP/3ΔHBD-HA). A construct encoding AAV capsid proteins VP1 and VP3 was generated from pAAV-DJ (Grimm et al., 2008) by introducing the point mutation T138A, which knocks out expression of VP2. Heparin-binding domains present in VP1/3 were removed by replacing amino acids R587-R590 with a Human influenza hemagglutinin (HA) tag—amino acids sequence YPYDVPDYA—or a hexahistidine tag. Either can be used in the composite/AAV production described below.

Plasmid combination to incorporate a binding scaffold in other capsid proteins are shown in Table 5:

TABLE 5

| | pCMV-VP1ΔHBD-Binder | pRep/Cap VP1ΔHBD/VP2ΔHBD/VP3ΔHBD-Binder | pCMV-VP2ΔHBD-Binder | pRep/Cap VP2/3ΔHBD-HIS6 or VP2/3ΔHBD-HA | pRep/Cap VP1/3ΔHBD-HIS6 or VP1/3ΔHBD-HA | pITR-CAG-tdtomato | pHelper |
|---|---|---|---|---|---|---|---|
| Strategy A | X | | | X | | X | X |
| Strategy B | | X | | | | X | X |
| Strategy C | | | X | | X | X | X | washed with 500 DMEM. Cells were incubated with DMEM and virus at a total volume of 240 uL for one hour at 37° C., after which 1 mL D10 was added on top of DMEM/virus.

Antibody Infection

HEK293-FT cells were plated on growth factor-depleted matrigel in a 24-well plate and reverse transfected with pCAG-GFP-GPI or pATT-DEST. 24 hours after transfection, was replaced with virus and D10 to a volume of 240 uL. 24 hours after initial addition of virus/D10, 500 uL of D10 was added to each well. Cells were imaged in Tyrode buffer (125 mM NaCl, 2 mM KCl, 3 mM CaCl2, 1 mM MgCl, 10 mM HEPES. 30 mM glucose. pH 7.3) 24 hours after infection. 48 hours after infection, cells were washed with DMEM and detached using acutase. Pelleted cells were washed with Tyrode buffer and resuspended in FACS buffer (2% of FBS, 0.1% NaN3, 1×PBS)

Imaging Cells after Infection

Cells were infected as per above but in glass-bottomed plates instead of plastic (still with growth factor-depleted matrigel). 24 hours after infection, media was replaced with Tyrode buffer and cells were treated with NucBlue (Thermo Fisher).

Conjugation of antibodies to ssDNA

Antibodies were conjugated to mMobA oligo with 3' amino label (IDT, 3'AmMo modification) using Innova biosciences Thunderlink Plus kit. Oligo was mixed with antibody to produce a ratio of 3:1 oligo:antibody. Excess oligo was removed after conjugation (per an option kit step). Conjugated antibody was run on an SDS-PAGE gel, and experimental ratio oligo:antibody was calculated using densitometry.

Formation of Antibody-AAV Composites

HUH-AAV was incubated in 1:20 salmon sperm DNA, 0.2 M MgCl2, and 20 pmoles antibody-oligo for 30 minutes at 37° C. Antibody-oligo was applied to cells immediately after composite formation.

Nanobody Infection

HEK293-FT cells were plated on growth factor-depleted matrigel in a 24-well plate and reverse transfected with pCAG-GFP-GPI (Kondoh et al., 1999) or pATT-DEST (Nadler et al., 2016). 24 hours after transfection, medium was removed and cells were washed with 500 DMEM. Cells were incubated with DMEM and virus at a total volume of 240 uL for one hour at 37° C., after which 1 mL D10 was added on top of DMEM/virus.

Gp2 Infection

HEK293-hIRB and HEK293-eGFP, or cells were plated on growth factor-depleted matrigel in a 24-well plate. 24 hours after plating, medium was removed and cells were Flow Cytometry Analysis of Infected Cells For nanobody and Gp2: Events were gated for single cells using FSC, SSC, and FSC-W. 100,000 single cells were used for analysis of each sample. Compensation for fluorescent bleed-through between tdTomato and GFP was calculated from single stain controls collected on each day.

Detection of Indels in Cells Infected with Cas9

1E6 Jurkat cells were seeded into each well of a 24-well plate at a density of 2e5 cells/mL. 1E7 GC/cell of an anti-CD7 conjugated antibody was added to cells with gentle mixing. 24 hours after infection, an additional 300 mL of media was added to cells (to reduce density and continue log phase growth). 72 hours after infection, cells were collected. gDNA was collected using the Zymo Quick-DNA kit. The AAVS1 genomic locus was amplified using TaKaRa Primestar GXL using 30 cycles. PCR product was purified using Zymo Clean and Concentrate 5; purified product from infected and non-infected cells was sent for Sanger sequencing. Sequencing was analyzed using Deskgen TIDE software to calculate the rate of indel formation in infected cells.

Example 7

In some embodiments, the binding protein may be linked to ssDNA via a commercial tag such as the SNAP, CLIP, or Halo tag, or another moiety, that reacts with a small moiety (e.g., a benzylguanine, benzylcytosine, or chloroalkane linker), which can be attached to ssDNA, e.g., via a NHS ester reaction with a $NH_2$-modified ssDNA.

In one embodiment, a four component system may be employed, e.g., an antibody, ssDNA, antibody activating reagent (e.g., lysine-reactive), and ssDNA activating reagent (e.g., $NH_2$-reactive). For antibody-ssDNA conjugation, the ratio of ssDNA to antibody can be controlled in two ways: (1) by varying the ratio of chemical linker to antibody and/or (2) by varying the ratio of activated ssDNA to activated antibody. In one embodiment, a sulfhydryl-reactive antibody conjugation reaction is employed.

In one embodiment, the antibody comprises an anti-Her2 antibody (e.g., to inhibit or treat breast cancer), anti-CD34 antibody (e.g., to target stem cells), anti-CD8 antibody (to target T-cells), or anti-CD19 antibody (to inhibit or treat B-ALL)

In one embodiment, the ssDNA is coupled to DARPins (designed ankyrin repeat proteins), a peptide toxin, scFv, a peptide hormone, or RNA aptamer (and aptamers with different backbone chemistry, e.g. LNA, PNA, etc.).

REFERENCES

Barrett et al., *Annu. Rev. Med.*, 65:333 (2014).
Berger et al., *J. Clin. Invest.*, 118:294 (2008).
Boucas, *J. Gene Med.*, 11(12):1103 (2008).
Chandler et al., *Nat. Rev. Microbiol.*, 11:525 (2013).
Chandler et al., *Nat. Rev. Microbiol.*, 1:525 (2013).
Duell et al., *Leukemia*, 6:2032 (2017).
Enger et al., *Hum. Gene Ther.*, 13:1115 (2002).
Gattinoni et al., *Nat. Med.*, 17:1290 (2011).
Golubovskaya, *Cancers*, 8: (2016), doi:10.3390/cancers8030036.
Grieger et al., *Nat. Protoc.*, 1:1412 (2006).
Grimm et al., *J, Virol.*, 2:5887 (2008).
Guo et al., *J. Virol. Methods*, 813:139 (2012).
Hagen et al., *Sci. Re.*, 4:3759 (2014).
Hedley et al., *Gene Therapy*, 13:88 (2006).
Hinrichs et al., *Proc. Natl. Acad. Sci. U.S.A.*, 106:17469 (2009).
Kalos et al., *Science Translational Medicine*, 3:95ra73 (2011).
Kondoh et al., *FEBS. Lett.*, 458:299 (1999).
Kronenberg et al., *Journal of Virology*, 79:5296 (2005).
Lovendahl et al., *J. Am. Chem. Soc.*, 13:7030 (2017).
Minch et al., *Molecular Therapy*, 21:109 (2012).
Minch et al., *Nat. Commun.*, 6:6246 (2015).
Muralidhar et al., *J. Virol. Am. Soc. Microb.*, 68:170 (1994).
Nadler et al., *Nat. Commun.*, 7:12266 (2016).
Nonnenmacher et al., *Gene Ther.*, 19:649 (2012).
Paulos et al., *Science Translational Medicine*, 2:55ra78 (2010).
Porter et al., *Cancer*, 2:331 (2011b).
Porter et al., *N. Engl. J. Med.*, 365:725 (2011a).
Sievers et al., *Annu. Rev. Med.*, 64:15 (2013).
Sommermeyer et al., *Leukemia*, 30:492 (2016).
Uchara et al., *EMBO J.*, 29:1412 (2010).
Vigneron, *Biomed Res Int.*, 2015:948501 (2015).
Warrington et al., *J. Virol.*, 78:6595 (2004).
Weiden et al., *N. Engl. J. Med.*, 130:1068 (1979).
Wu et al., *Journal of Virology*, 74:8635 (2000).
Yakobson et al., *J. Virol.*, 61:972 (1987).
Yang et al., *Human Gene Therapy*, 9:1929 (1998).
Zakeri et al., *Proc. Natl. Acad. Sci. U.S.A.*, 109:E690 (2012).
Zhang et al., *J. Virol*, 76:12023 (2002).
Zhang, *Genomics Proteomics Bioinformatics*, 11:264 (2013).
Boucas et al., J. Gene Med., 11(12):1103 (2009)
Fenno et al., Nat. Methods, 11(7):763 (2014)
Chan et al., Nat. Neurosci., 20:1172 (2017)

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A helper-free population of infectious recombinant adeno-associated virus (AAV) with altered tropism, comprising: infectious recombinant AAV comprising a modified AAV capsid having an insertion that includes one or more single stranded nucleic acid binding domains and a modified heparin binding domain, and a viral genome, wherein the insertion is bound to a molecule capable of providing the altered tropism which is altered relative to a corresponding AAV without the modification in the viral capsid, wherein the modified heparin binding domain has decreased binding to heparin relative to a corresponding AAV capsid having an unmodified heparin binding domain, wherein the one or more single stranded nucleic acid binding domains are HUH endonuclease domains.

2. The population of claim 1 wherein the insertion in the modified AAV capsid is in the heparin binding domain.

3. The population of claim 1 wherein the one or more HUH endonuclease domains have a sequence having at least 80% amino acid sequence identity to a HUH domain in one or more of SEQ ID Nos. 2-10 and 20-21.

4. The population of claim 1 wherein up to 10 HUH endonuclease domains are in the insertion.

5. The population of claim 1 which has a plurality of distinct recombinant viruses each having different HUH endonuclease domains.

6. The population of claim 1 wherein the viral genome is a recombinant genome having at least one expression cassette for an exogenous gene product.

7. The population of claim 6 wherein the exogenous gene product is a prophylactic or therapeutic gene product or a cytotoxic gene product.

8. The population of claim 1 wherein the insertion in the modified AAV capsid is in VP1 or VP2 of an AAV capsid.

9. The population of claim 1 wherein the insertion in the modified AAV capsid is at one of positions 455, 456, 457, 585, 586, 587, 588, 589, 590, or 591.

10. The population of claim 1 wherein the molecule is an antibody or an antigen binding portion thereof.

11. The population of claim 10 wherein the antibody is an anti-CD3 antibody, anti-CD4 antibody, anti-CD7 antibody, anti-Her2 antibody, anti-CD34 antibody, anti-CD8, anti-CD20 antibody, or anti-CD19 antibody.

12. A system comprising:
a helper-free population of infectious recombinant AAV, comprising: infectious recombinant AAV comprising a modified AAV capsid having an insertion that includes one or more single stranded nucleic acid binding domains and a modified heparin binding domain and a viral genome, wherein the modified heparin binding domain has decreased binding to heparin relative to a corresponding AAV capsid having an unmodified heparin binding domain; and
a substrate for the single stranded nucleic acid binding domain, wherein the one or more single stranded nucleic acid binding domains are HUH endonuclease domains.

13. The system of claim 12 further comprising a targeting molecule.

14. The system of claim 13 wherein the substrate is covalently linked to the targeting molecule.

15. A method of targeting mammalian cells in vivo, comprising:
a) providing a helper-free population of infectious recombinant MV, comprising: recombinant MV comprising a modified MV viral capsid having an insertion that includes one or more single stranded nucleic acid binding domains and a modified heparin binding domain and a viral genome, wherein the modified heparin binding domain has decreased binding to heparin relative to a corresponding MV capsid having an unmodified heparin binding domain;
b) providing a single stranded nucleic acid binding substrate for the one or more single stranded nucleic acid binding domains covalently linked to a targeting molecule;
c) combining the helper-free population of recombinant virus and the substrate covalently linked to the targeting molecule to form a conjugate; and d) administering the conjugate to a mammal, wherein the one or more single stranded nucleic acid binding domains are HUH endonuclease domains.

16. The method of claim 15 wherein the mammalian cells are human cells.

17. The method of claim 15 wherein the targeting molecule is an antibody or an antigen binding portion thereof.

18. The method of claim 17 wherein the antibody is an anti-CD3 antibody, anti-CD4 antibody, anti-CD7 antibody, anti-Her2 antibody, anti-CD34 antibody, anti-CD8, anti-CD20 antibody, or anti-CD19 antibody.

* * * * *

UNITED STATES PATENT AND TRADEMARK OFFICE
CERTIFICATE OF CORRECTION

PATENT NO. : 11,851,671 B2
APPLICATION NO. : 16/758602
DATED : December 26, 2023
INVENTOR(S) : Schmidt et al.

It is certified that error appears in the above-identified patent and that said Letters Patent is hereby corrected as shown below:

On the Title Page

On page 2, in Column 2, under "Other Publications", Line 36, delete "Adenoassociated" and insert --Adeno-associated-- therefor In the Drawings On sheet 2 of 33, Fig. 2B, Line 1, delete "(gc/ul)" and insert --(gc/µl)-- therefor On sheet 33 of 33, Fig. 21D, Method B, Line 2, delete "tota" and insert --total-- therefor In the Specification In Column 1, Line 14, after "which", delete "is"

In Column 1, Line 31, delete "(cytotoxcity)," and insert --(cytotoxicity),-- therefor In Column 2, Line 43, delete "Darpin." and insert --Darpin,-- therefor In Column 2, Line 61, delete "'arming'viral" and insert --'arming' viral-- therefor In Column 4, Line 55, delete "Reporter: GFP;" and insert --Reporter:GFP;-- therefor In Column 6, Line 53, delete "Rep72." and insert --Rep72,-- therefor In Column 6, Line 63, delete "vectors." and insert --vectors,-- therefor In Column 8, Line 26, delete "VP1." and insert --VP1,-- therefor Signed and Sealed this
Tenth Day of December, 2024

Katherine Kelly Vidal
*Director of the United States Patent and Trademark Office*

CERTIFICATE OF CORRECTION (continued)
U.S. Pat. No. 11,851,671 B2

In Column 8, Line 50, delete "VPS" and insert --VP3-- therefor

In Column 8, Line 61, delete "incorporated." and insert --incorporated,-- therefor In Column 9, Line 65, delete "AAV-D J" and insert --AAV-DJ-- therefor In Column 11, Line 9, delete "AAV 2" and insert --AAV2-- therefor In Column 14, Line 30, delete ""polypeptide" and insert --"polypeptide"-- therefor In Column 14, Line 30, delete "protein"" and insert --"protein"-- therefor In Column 15, Line 29, delete "Benjamin." and insert --Benjamin,-- therefor In Column 16, Line 60, delete "*Nature*." and insert --*Nature*,-- therefor In Column 17, Line 10, delete "*Therapy*." and insert --*Therapy*,-- therefor In Column 17, Line 23, delete "(1994):" and insert --(1994);-- therefor In Column 17, Line 23, delete "*Nature*" and insert --*Nature*,-- therefor In Column 17, Line 24, delete "*Biotechnology*." and insert --*Biotechnology*,-- therefor In Column 17, Lines 45-46, delete "immunoglobulin, the" and insert --immunoglobulin. The-- therefor In Column 19, Line 32, delete "therapy." and insert --therapy,-- therefor In Column 20, Line 26, delete "W3" and insert --VP3-- therefor In Column 20, Line 26, delete "(SEQ." and insert --(SEQ-- therefor In Column 20, Line 38, delete "anti body-ssDNA-RepB" and insert --antibody-ssDNA-RepB-- therefor In Column 21, Line 1, delete "VP" and insert --VP1-- therefor In Column 21, Line 1, delete "VP)" and insert --VP1)-- therefor In Column 21, Line 58, delete "Trail" and insert --Tral-- therefor In Column 21, Line 59, delete "(GGGG)$_2$" and insert --(GGGGS)$_2$-- therefor In Column 21, Line 63, delete "g." and insert --(e.g.-- therefor In Column 22, Line 2, before "IL-15,", insert --IL-12,--

CERTIFICATE OF CORRECTION (continued)
U.S. Pat. No. 11,851,671 B2

In Column 22, Line 5, delete "CDG4" and insert --CD64-- therefor

In Column 22, Line 26, delete "modification." and insert --modification,-- therefor In Column 22, Line 32, delete "modification." and insert --modification,-- therefor In Column 22, Line 34, delete "64" and insert --64.-- therefor In Column 23, Line 22, delete "YLEFBNYV." and insert --YLE FXNYV.-- therefor In Column 26, Line 47, delete "metallothionin" and insert --metallothionein-- therefor In Column 31, Line 6, delete "practitioners, the" and insert --practitioners. The-- therefor In Column 33, Line 38, delete "Ipswich." and insert --Ipswich,-- therefor In Column 34, in table 1, Column 1, Lines 6-7, delete "DCV (SEQ NO: 21)" and insert --DCV (SEQ ID NO: 21)-- therefor In Column 34, in table 1, Column 2, Lines 6-7, delete "ID circovirus" and insert --Duck circovirus-- therefor In Column 34, in table 1, Column 3, Line 6, delete "Duck" therefor In Column 35, in table 1-continued, Column 1, Line 7, after "Tra1$^+$ (SEQ ID NO:", insert --5)--

In Column 35, table 1-continued, Line 19, delete "Biol," and insert --Biol.-- therefor In Column 36, Line 38, delete "charge." and insert --charge,-- therefor In Column 37, Line 13, delete "designed." and insert --designed,-- therefor In Column 38, Line 46, delete "VP" and insert --VP1-- therefor In Column 39, Line 21, delete "helper-fre" and insert --helper-free-- therefor In Column 39, Line 41, delete "T-cells." and insert --T-cells,-- therefor In Column 39, Line 44, delete "immunotherapy" and insert --immunotherapy.-- therefor In Column 40, Line 53, delete "145" and insert --T457-- therefor In Column 40, Line 56, delete "B:" and insert --B;-- therefor In Column 40, Line 67, delete "VP." and insert --VP1.-- therefor

CERTIFICATE OF CORRECTION (continued)
U.S. Pat. No. 11,851,671 B2

In Column 41, Line 55, delete "ug" and insert --µg-- therefor

In Column 42, Line 2, delete "U/uL" and insert --U/µL-- therefor

In Column 42, Line 5, delete "U/uL," and insert --U/µL,-- therefor

In Column 42, Line 11, delete "ug/mL" and insert --µg/mL-- therefor

In Column 42, Line 15, delete "Tris HCl," and insert --TrisHCl,-- therefor

In Column 42, Line 22, delete "uM" and insert --µM-- therefor

In Column 42, Line 30, delete "uM" and insert --µM-- therefor

In Column 42, Line 31, delete "uM" and insert --µM-- therefor

In Column 42, Line 48, delete "uL" and insert --µL-- therefor

In Column 42, Line 48, delete "uL" and insert --µL-- therefor

In Column 42, Line 50, delete "uL." and insert --µL.-- therefor

In Column 42, Line 50, delete "uL" and insert --µL-- therefor

In Column 42, Line 66, delete "MgCl2" and insert --MgCl$_2$-- therefor

In Column 42, Line 67, delete "MnCl2" and insert --MnCl$_2$-- therefor

In Column 43, Line 1, delete "MnCl2," and insert --MnCl$_2$,-- therefor

In Column 43, Line 1, delete "MnCl2," and insert --MnCl$_2$,-- therefor

In Column 44, Line 38, delete "cap-Bindery" and insert --cap-Binderv-- therefor

In Column 45, Line 13, delete "VP/3ΔHBD-HIS6" and insert --VP1/3ΔHBD-HIS6-- therefor In Column 45, Line 14, delete "VP/3ΔHBD-HA)." and insert --VP1/3ΔHBD-HA).-- therefor In Column 45, Line 42, delete "3'AmMo" and insert --3' AmMo-- therefor In Column 45, Line 51, delete "MgCl2," and insert --MgCl$_2$,-- therefor In Column 45, Line 62, delete "uL" and insert --µL-- therefor In Column 46, Line 2, delete "uL" and insert --µL-- therefor

CERTIFICATE OF CORRECTION (continued)
U.S. Pat. No. 11,851,671 B2

In Column 46, Line 9, delete "uL." and insert --µL.-- therefor

In Column 46, Line 10, delete "uL" and insert --µL-- therefor

In Column 46, Line 12, delete "CaCl2," and insert --CaCl$_2$,-- therefor

In Column 46, Line 17, delete "NaN3," and insert --NaN$_3$,-- therefor

In the Claims

In Column 92, Line 46, In Claim 15, delete "MV," and insert --AAV,-- therefor

In Column 92, Line 46, In Claim 15, delete "MV" and insert --AAV-- therefor

In Column 92, Line 47, In Claim 15, delete "MV" and insert --AAV-- therefor

In Column 92, Line 52, In Claim 15, delete "MV" and insert --AAV-- therefor